US012569036B2

(12) United States Patent
Lovett

(10) Patent No.: US 12,569,036 B2
(45) Date of Patent: Mar. 10, 2026

(54) LACING CONFIGURATION FOR A BRACE

(71) Applicant: Boa Technology Inc., Denver, CO (US)

(72) Inventor: Kristopher Lovett, Denver, CO (US)

(73) Assignee: Boa Technology Inc., Denver, CO (US)

( * ) Notice: Subject to any disclaimer, the term of this patent is extended or adjusted under 35 U.S.C. 154(b) by 290 days.

(21) Appl. No.: 17/024,493

(22) Filed: Sep. 17, 2020

(65) Prior Publication Data

US 2021/0068503 A1    Mar. 11, 2021

Related U.S. Application Data

(63) Continuation of application No. 16/017,698, filed on Jun. 25, 2018, now Pat. No. 10,791,798, which is a continuation of application No. 15/144,498, filed on May 2, 2016, now Pat. No. 10,004,297.

(60) Provisional application No. 62/242,145, filed on Oct. 15, 2015.

(51) Int. Cl.
| | |
|---|---|
| *A43C 11/16* | (2006.01) |
| *A43C 1/00* | (2006.01) |
| *A43C 1/04* | (2006.01) |
| *A43C 11/20* | (2006.01) |
| *A61F 5/01* | (2006.01) |

(52) U.S. Cl.
CPC .............. *A43C 11/165* (2013.01); *A43C 1/00* (2013.01); *A43C 1/04* (2013.01); *A43C 11/20* (2013.01); *A61F 5/01* (2013.01); *Y10T 24/21* (2015.01)

(58) Field of Classification Search
CPC ......... A43C 11/165; A43C 11/20; A43C 1/00; A43C 1/04; A61F 5/01; Y10T 24/21

USPC .......................................................... 602/62
See application file for complete search history.

(56) References Cited

U.S. PATENT DOCUMENTS

| | | | |
|---|---|---|---|
| 157,972 | A | 12/1874 | Pruett |
| 189,027 | A | 4/1877 | Evans |
| 1,466,078 | A | 8/1923 | Washburn |
| 5,117,567 | A | 6/1992 | Berger |
| 5,177,882 | A | 1/1993 | Berger |
| 5,327,662 | A | 7/1994 | Hellenbeck |

(Continued)

FOREIGN PATENT DOCUMENTS

| | | |
|---|---|---|
| CN | 101193568 A | 6/2008 |
| CN | 201157042 Y | 12/2008 |

(Continued)

*Primary Examiner* — Alireza Nia
*Assistant Examiner* — Michael Milo
(74) *Attorney, Agent, or Firm* — Kilpatrick Townsend & Stockton LLP

(57) ABSTRACT

A lacing system for an article may include a tensioning mechanism, a plurality of guide members, and a lace that is operationally coupled with the tensioning mechanism and that is routed along a lace path of the article via the plurality of guide members. The lace is routed along the lace path so that a first portion of the lace is routed directly from the tensioning mechanism to a top end of the lace path and so that a second portion of the lace is routed directly from the tensioning mechanism to a position that is adjacent a bottom end of the lace path. Tensioning of the lace, via the tensioning mechanism, causes the top end of the lace path and the position adjacent the bottom end of the lace path to be initially tensioned.

19 Claims, 41 Drawing Sheets

(56)                    References Cited

U.S. PATENT DOCUMENTS

| | | | |
|---|---|---|---|
| 5,341,583 A | 8/1994 | Hellenbeck | |
| 5,345,697 A | 9/1994 | Quellais | |
| 5,381,609 A | 1/1995 | Hieblinger | |
| 6,694,643 B1 | 2/2004 | Hsu | |
| 7,591,050 B2 | 9/2009 | Hammerslag | |
| 7,950,112 B2 | 5/2011 | Hammerslag et al. | |
| 8,091,182 B2 | 1/2012 | Hammerslag et al. | |
| 9,339,082 B2 | 5/2016 | Hammerslag et al. | |
| 9,700,101 B2 | 7/2017 | Lovett et al. | |
| 10,004,297 B2 | 6/2018 | Lovett | |
| 2007/0130799 A1 | 6/2007 | Seliger et al. | |
| 2008/0060167 A1* | 3/2008 | Hammerslag | A43C 11/165 |
| | | | 24/714.6 |
| 2008/0066272 A1* | 3/2008 | Hammerslag | A61F 5/01 |
| | | | 602/5 |
| 2008/0172848 A1 | 7/2008 | Chen | |
| 2011/0225843 A1 | 9/2011 | Kerns et al. | |
| 2012/0240428 A1 | 9/2012 | Knoll | |
| 2014/0123449 A1* | 5/2014 | Soderberg | A43C 1/003 |
| | | | 24/712.1 |
| 2014/0135672 A1* | 5/2014 | Joseph | A61F 5/028 |
| | | | 602/19 |
| 2014/0196312 A1 | 7/2014 | Sakaue et al. | |
| 2014/0221889 A1* | 8/2014 | Burns | A61F 5/0102 |
| | | | 602/5 |
| 2014/0290016 A1 | 10/2014 | Lovett et al. | |
| 2015/0059206 A1* | 3/2015 | Lovett | A43C 11/004 |
| | | | 12/142 R |
| 2015/0059208 A1 | 3/2015 | Kerns et al. | |
| 2015/0150705 A1* | 6/2015 | Capra | A61F 5/0102 |
| | | | 602/6 |
| 2016/0081421 A1 | 3/2016 | Fischer et al. | |
| 2017/0105489 A1 | 4/2017 | Lovett | |

FOREIGN PATENT DOCUMENTS

| | | |
|---|---|---|
| CN | 101631480 A | 1/2010 |
| CN | 103462737 A | 12/2013 |
| WO | 2015035257 A2 | 5/2015 |

* cited by examiner

1400

1402

1404

$Z_1$ $Z_2$

1404

1402

1.

2.

2602

2630

2632

2600

2620

LACING CONFIGURATION FOR A BRACE

CROSS-REFERENCE TO RELATED APPLICATIONS

This application is a continuation of U.S. patent application Ser. No. 16/017,698, filed Jun. 25, 2018, entitled "Lace Configurations for Footwear," which is a continuation of U.S. patent application Ser. No. 15/144,498, filed May 2, 2016, entitled "Lace Configurations for Footwear," which claims priority to Provisional U.S. Patent Application No. 62/242,145, filed Oct. 15, 2015, entitled "Lace Configurations for Footwear," the entire disclosures of which are hereby incorporated by reference, for all purposes, as if fully set forth herein.

BACKGROUND

Footwear and other articles that are closed and/or tightened often include a lace, cord, or other tension member. The lace is typically positioned on the footwear or article so that it spans an opening that may be narrowed to close and/or tighten the footwear or article. Once the lace is tensioned to close and/or tighten the footwear or article, the tension member may be secured to prevent loosening or opening of the footwear or article. The lace is typically positioned along a symmetrical path about the opening of the footwear or article.

Shoes are common examples of footwear that employ such lace. Specifically, many shoes include shoe lace that is positioned along a tongue or opening portion of the shoe so that the opposing ends of the shoelace are adjacent the shoe's throat or collar and so that the shoelace is symmetrically laced along the length of the tongue or opening. A middle portion of the shoelace is often disposed at a distal end of the tongue or opening, commonly near the toe box.

BRIEF DESCRIPTION OF THE INVENTION

The embodiments here provide lacing systems for footwear and articles. The lacing systems have unique lace paths that may be employed to minimize negative effects associated with shifting of the lace and/or to provide a more uniform and even closure of the footwear or article. According to one embodiment, a lacing system for tightening footwear is provided. The footwear includes opposing sides and a lace path extending between the opposing sides. The lace path includes a bottom end that is positioned near a toe box of the footwear, a top end that is positioned opposite the bottom end, and a mid-portion that is roughly equidistant from the top end and the bottom end. The lacing system includes a tensioning mechanism and a plurality of guide members that are coupled with the footwear. The lacing system also includes a lace that is operationally coupled with the tensioning mechanism and that is routed about the footwear along the lace path via the plurality of guide members. The lace includes a first portion and a second portion that are each operationally coupled with the tensioning mechanism so that operation of the tensioning mechanism simultaneously tensions both the first portion and the second portion. The lace is routed along the lace path so that the first portion is routed directly from the tensioning mechanism to the top end of the lace path and is routed therefrom toward the mid-portion of the lace path, and so that the second portion is routed directly from the tensioning mechanism to adjacent the mid-portion of the lace path and is routed therefrom toward the bottom end of the lace path.

Tensioning of the first portion and the second portion of the lace immediately tensions the top end and the mid-portion of the lace path and thereby immediately tightens corresponding portions of the footwear. In each of the embodiments, the lace may be a unitary member with the first portion connected to the second portion between the mid-portion and the bottom end of the lace path.

In some embodiments, the lacing system may also include a stop member that limits movement of the first portion and/or the second portion of lace about the lace path. According to one embodiment, the tensioning mechanism may be coupled with the footwear in one of following locations: centrally on a tongue portion of the footwear, on a side of the footwear adjacent an eyestay, or adjacent a sole of the footwear. The first portion and/or the second portion of lace may be routed directly from the tensioning mechanism to the respective positions via tubing. The lace may be routed from the tensioning mechanism and around a heel of the footwear to the top end of the lace path. The tensioning mechanism may be a rotary based device that is manually operable or a motorized device.

According to one embodiment, the plurality of guide members includes at least one guide with an elongated channel. In said embodiment, the plurality of guide members may also include a second guide having a longitudinal length that is shorter than the guide with the elongated channel. The guide with the elongated channel may be positioned laterally outward from the second guide in respect to the lace path so that opposing ends of the second guide are disposed between opposing ends of the guide with the elongated channel.

According to another embodiment, a lacing system for tightening an article is provided. The article includes a lace path having a bottom end and a top end. The lacing system includes a tensioning mechanism and a plurality of guide members that are coupled with the article along the lace path. The lacing system also includes a lace that is operationally coupled with the tensioning mechanism and routed along the lace path via the plurality of guide members. The lace includes a first portion and a second portion that are each operationally coupled with the tensioning mechanism so that operation of the tensioning mechanism simultaneously tensions both the first portion and the second portion. The lace is routed along the lace path so that the first portion is routed directly from the tensioning mechanism to the top end of the lace path and is routed therefrom toward the bottom end of the lace path, and so that the second portion is routed directly from the tensioning mechanism to a position adjacent the bottom end of the lace path. Tensioning of the first portion and the second portion of the lace via the tensioning mechanism immediately tensions the top end and the position adjacent the bottom end of the lace path.

In some embodiments, the position adjacent the bottom end of the lace path is a position that is equidistant from the top end and the bottom end. In such embodiments, the second portion of the lace is routed from the position adjacent the bottom end of the lace path toward the bottom end of the lace path. In other embodiments, the position adjacent the bottom end of the lace path is at the bottom end of the lace path. In such embodiments, the second portion of the lace is routed from the bottom end of the lace path toward the top end of the lace path such that tensioning of the first portion and the second portion of the lace via the tensioning mechanism immediately tensions the top end and the bottom end of the lace path. The lace may be a unitary member with the first and second portions connected, or the first and second portions may be separate portions that each terminate on the article and/or on the tensioning mechanism.

According to another embodiment, a lacing system for tightening an article is provided. The article has a lace path with a bottom end and a top end and the lacing system includes a tensioning mechanism and a lace that is operationally coupled with the tensioning mechanism. The lace is routed along the lace path. The lace includes a first portion and a second portion that are each operationally coupled with the tensioning mechanism so that operation of the tensioning mechanism simultaneously tensions both the first portion and the second portion. The lacing system also includes a first guide member that is attached to the article. The first guide member includes a lumen or channel that is aligned longitudinally along the lace path and that is configured to route the first portion of the lace along the lace path. The lacing system further includes a second guide member that is attached to the article. The second guide member includes a lumen or channel that is aligned longitudinally along the lace path and that is configured to route the second portion of the lace along the lace path. A length of the lumen or channel of the second guide member may be longer than a length of the lumen or channel of the first guide member and the second guide member may be positioned along the lace path, and in respect to the first guide member, so that opposing ends of the lumen or channel of the first guide member are disposed between opposing ends of the lumen or channel of the second guide member. In this manner, the second portion of lace that is routed through the lumen or channel of the second guide member bypasses (i.e., is routed past) the first portion of the lace that is routed through the lumen or channel of the first guide member.

In some embodiments, the second guide member is positioned latterly outward or offset from the first guide member with respect to the lace path. The second guide member and/or the first guide member may be a tubing component. In some instances, the second portion of lace may be positioned through the lumen or channel of the first guide member so that the first portion of lace and second portion of lace are each positioned through the first guide member.

According to another embodiment, a method of coupling a lacing system with an article is provided. The method includes coupling a tensioning mechanism with the article and coupling a plurality of guide members with the article so as to define a lace path having a bottom end and a top end. The method also includes coupling a first portion and a second portion of a lace with the tensioning mechanism so that operation of the tensioning mechanism simultaneously tensions both the first portion and the second portion of the lace. The method further includes routing the lace along the lace path via the plurality of guide members so that the first portion is routed directly from the tensioning mechanism to the top end of the lace path and is routed therefrom toward the bottom end of the lace path, and so that the second portion is routed directly from the tensioning mechanism to a position adjacent the bottom end of the lace path. This lace path is effective such that tensioning of the first portion and the second portion of the lace via the tensioning mechanism immediately tensions the top end and the position adjacent the bottom end of the lace path.

In some embodiments, the article is a shoe and the first portion or the second portion of lace are routed around a heel or collar of the shoe. In embodiments wherein the article is a shoe, the tensioning mechanism may be positioned on the heel of the shoe.

BRIEF DESCRIPTION OF THE DRAWINGS

The present invention is described in conjunction with the appended figures.

Figure 1:
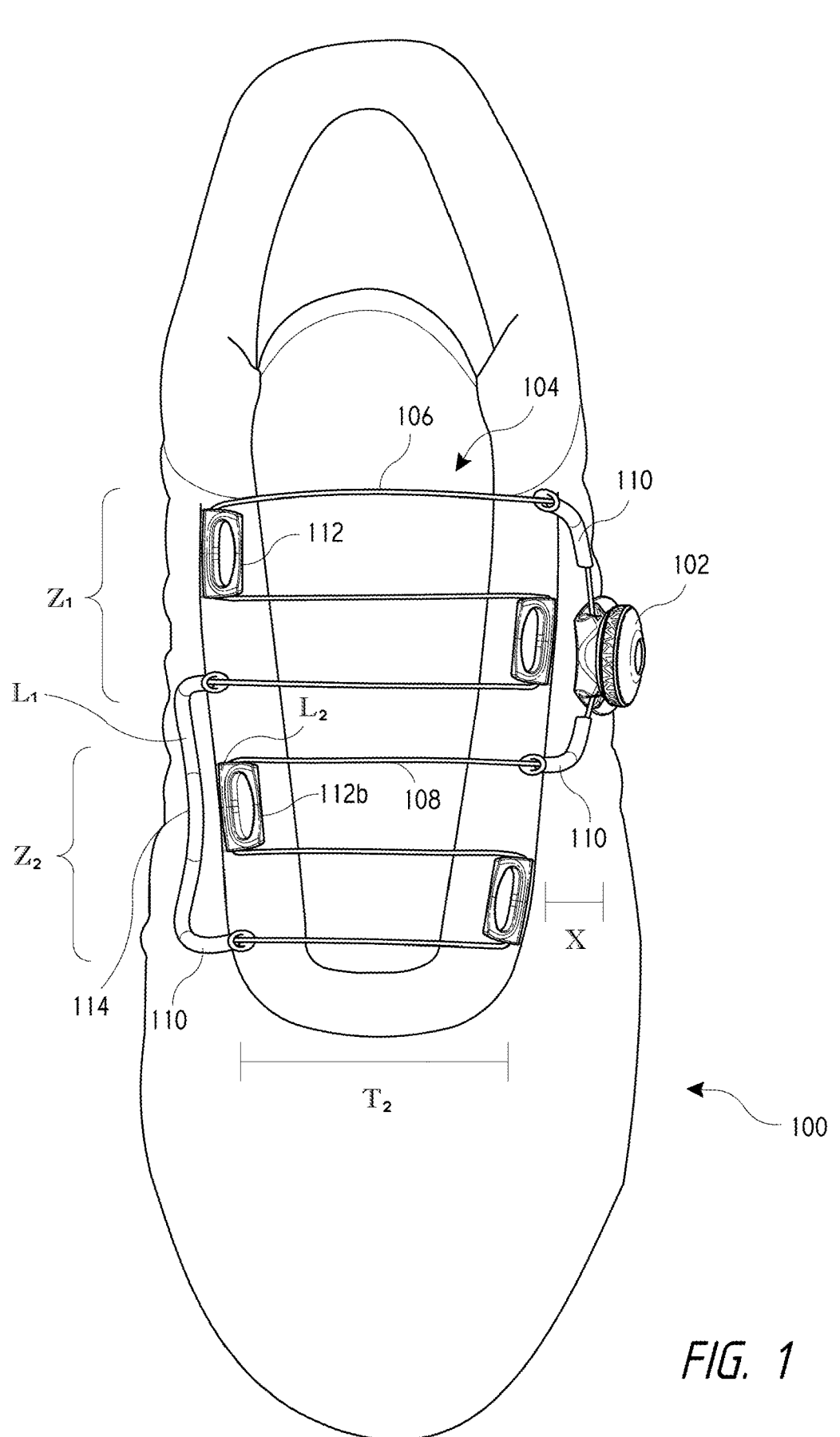
FIG. 1 illustrates an embodiment of a lace path of a shoe that limits dynamic lace shifting of the lace and/or provides a more uniform tightening.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

The embodiments described herein provide closure devices and lacing configurations that improve the fit of footwear about a user's foot. Specifically, the lacing configurations improve the closure of the footwear about the foot and also improve the tightness or fit of the footwear during usage. The lacing configurations may be especially useful for lacing systems that employ lace and/or guide materials that result in relative low friction, which have a tendency to shift or move as the footwear is worn. For example, the lace may easily slide within guides that are positioned about the footwear due to reduced friction between the lace and guides as compared to conventional lacing systems. The low friction may likewise result from small lace diameters (e.g., 0.8-1.2 mm and the like), and/or due to the use of lace materials have increased bend/flexibility.

The dynamic shifting of the lace may be caused due to increased pressure within one or more regions of the shoe (e.g., near the heel or toe) in response to the shoe bending and flexing due to the user's movement. For example, at the user walks, runs, jumps, turns, etc., the user's foot and/or leg may press against the upper portion of the shoe, which causes the upper portion to bend and flex. Bending and flexing of the shoe causes an increases in tension in the lace positioned within or adjacent the upper portion of the shoe, which pulls on the distal portions of the lace (e.g., near the toe) and causes the lace to slide or shift within the footwear's guides. The result is a widening or enlarging of the upper portion of the shoe and a contraction or restriction of the distal portion of the shoe (e.g., toe region) that is removed or remote from the upper shoe portion.

In some embodiments it may be desired to prevent dynamic shifting of the lace to prevent repeated widening/enlarging and constriction/contraction of portions of the footwear in order to increase the support that is offered by the footwear and/or increase the comfort in wearing the footwear. For example, repeated widening and constriction of portions of the footwear may irritate a user and/or otherwise be uncomfortable. In other instances, widening of the footwear in response to user movements, such as widening of the upper tongue portion in response to running or jumping, may reduce the support provided by the footwear.

In other embodiments, the lacing configurations described herein may increase the uniformity with which the footwear is tightened and/or closed about the foot. For example, the tension in the lace is typically greatest adjacent a mechanism that is used to tighten the lace and is typically reduced the farther the lace extends or travels from the tightening mechanism due to frictional losses and/or other tension losses. As such, the portions or areas of the footwear that are adjacent the tightening mechanism are often tightened slightly more than the portions or areas of the footwear that are removed or remote from the tightening mechanism. As the user wears the footwear, the lace tension may equalize or become more uniform due to shifting of the lace about the footwear and/or guides. This may result in the portions or areas of the footwear that are adjacent the tightening mechanism loosening slightly and the portions or areas of the footwear that are removed or remote from the tightening mechanism tightening slightly. Because of this loosening/tightening of areas of the footwear, the user may be required to readjust the lace tension in the footwear (i.e., tighten or loosen the lace) in order to achieve a initial and desired fit or feel of the footwear about the foot.

The embodiments described herein provide a more uniform tightening and/or closure of the footwear about the foot. In addition to the above described benefits, additional benefits of the lacing configurations described herein include: components or configurations that limit and/or prevent dynamic lace shifting, configurations that enable differential tightness or pressure to be applied to different portions of the footwear, and the like. Having described several aspects and features of the embodiments above, additional details of the embodiments will be realized with reference to the description of the several drawings provided herein.

Many of the embodiment described and illustrated herein are directed to a lacing system for tightening footwear is described herein. The footwear includes opposing sides and a lace path extending between the opposing sides. The lace path includes a bottom end that is positioned near a toe box of the footwear, a top end that is positioned opposite the bottom end, and a mid-portion that is roughly equidistant from the top end and the bottom end. The lacing system includes a tensioning mechanism and a plurality of guide members that are coupled with the footwear. The lacing system also includes a lace that is operationally coupled with the tensioning mechanism and that is routed about the footwear along the lace path via the plurality of guide members. The lace includes a first portion and a second portion that are each operationally coupled with the tensioning mechanism so that operation of the tensioning mechanism simultaneously tensions both the first portion and the second portion. The lace is routed along the lace path so that the first portion is routed directly from the tensioning mechanism to the top end of the lace path and is routed therefrom toward the mid-portion of the lace path, and so that the second portion is routed directly from the tensioning mechanism to adjacent the mid-portion of the lace path and is routed therefrom toward the bottom end of the lace path. Tensioning of the first portion and the second portion of the lace immediately tensions the top end and the mid-portion of the lace path and thereby immediately tightens corresponding portions of the footwear. In each of the embodiments, the lace may be a unitary member with the first portion connected to the second portion between the mid-portion and the bottom end of the lace path.

It should be realized that the embodiments are not limited to footwear applications. Rather, the lacing systems described herein may be used for tightening virtually any article that includes a lace path having a bottom end and a top end. For example, the lacing system may include a tensioning mechanism and a plurality of guide members that are coupled with the article along the lace path. The lacing system may also include a lace that is operationally coupled with the tensioning mechanism and routed along the lace path via the plurality of guide members. The lace may include a first portion and a second portion that are each operationally coupled with the tensioning mechanism so that operation of the tensioning mechanism simultaneously tensions both the first portion and the second portion. The lace may be routed along the lace path so that the first portion is routed directly from the tensioning mechanism to the top end of the lace path and is routed therefrom toward the bottom end of the lace path and so that the second portion is routed directly from the tensioning mechanism to a position adjacent the bottom end of the lace path. Tensioning of the first portion and the second portion of the lace via the tensioning mechanism may immediately tensions the top end and the position adjacent the bottom end of the lace path.

The unique lace paths described herein may be achieved via one or more guides that route the lace. For instance, according to one embodiment, a lacing system for tightening an article may include a tensioning mechanism and a lace that is operationally coupled with the tensioning mechanism and that is routed along the lace path. The lace may include a first portion and a second portion that are each operationally coupled with the tensioning mechanism so that operation of the tensioning mechanism simultaneously tensions both the first portion and the second portion. The lacing system may also include a first guide member that is attached to the article. The first guide member may have a lumen or channel that is aligned longitudinally along the lace path and that is configured to route the first portion of the lace along the lace path. The lacing system may further include a second guide member that is attached to the article. The second guide member may have a lumen or channel that is aligned longitudinally along the lace path and that is configured to route the second portion of the lace along the lace path. A length of the lumen or channel of the second guide member may be longer than a length of the lumen or channel of the first guide member and the second guide member may be positioned along the lace path, and in respect to the first guide member, such that opposing ends of the lumen or channel of the first guide member are disposed between opposing ends of the lumen or channel of the second guide member. In this manner, the second portion of lace that is routed through the lumen or channel of the second guide member bypasses (i.e., is routed past) the first portion of the lace that is routed through the lumen or channel of the first guide member.

Figure 15A:
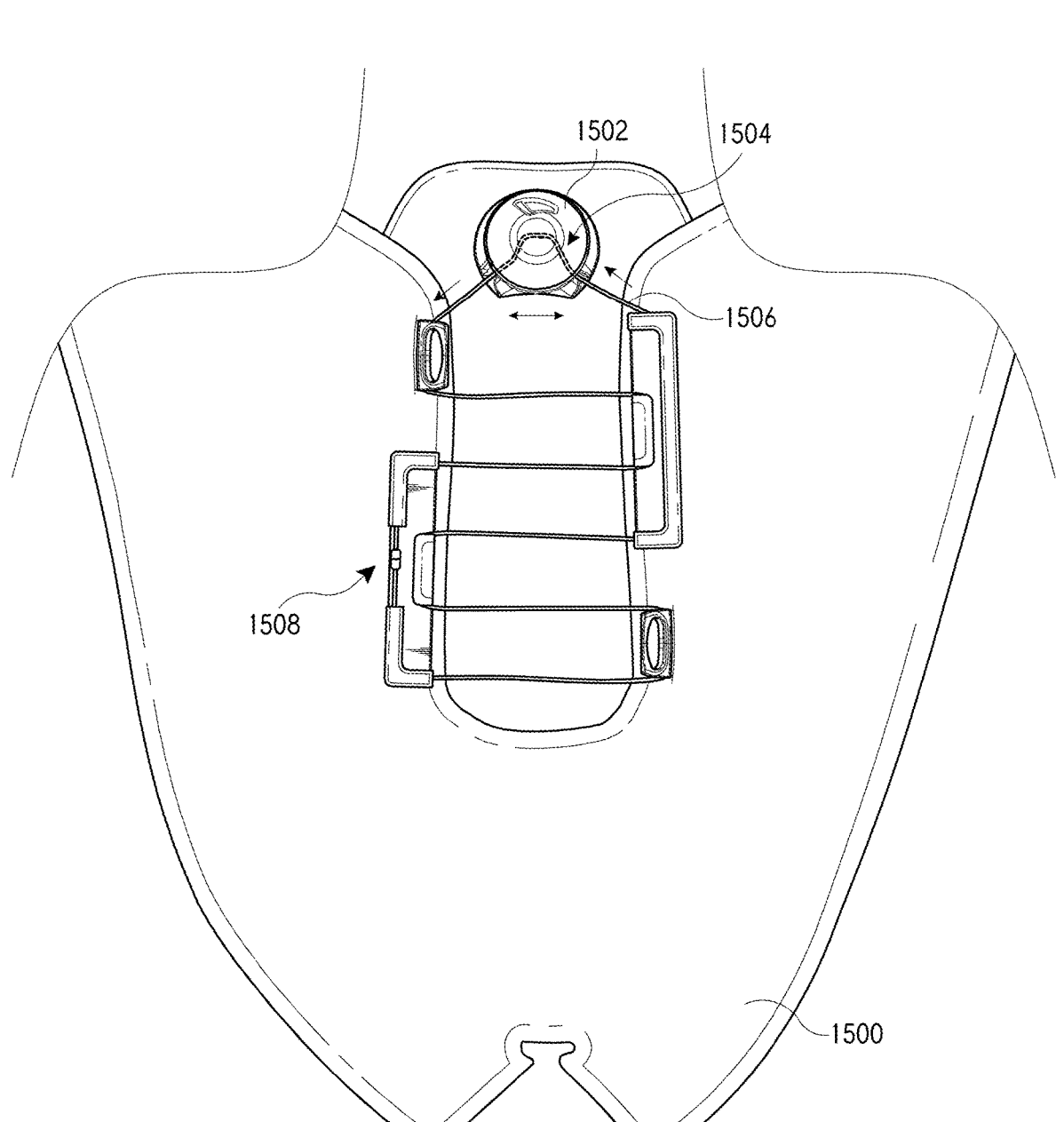
FIG. 15A illustrates a lacing system that includes a tensioning mechanism having a lumen through which a lace may be inserted.

Referring now to FIG. 1, illustrated is an embodiment of a shoe 100 that limits dynamic lace shifting and/or provides a more uniform tightening. This is achieved by positioning the lace so that it initially and simultaneously tensions both an upper and mid or lower portion of the shoe 100. The shoe 100 includes a tightening mechanism 102, such as a reel based device (hereinafter reel assembly 100). Reel assembly 100 includes a knob (not numbered) that may be grasped and rotated by a user to tighten and/or loosen a lace 104. The reel assembly 100 may include a spool (not shown) having an interior channel or post about which the lace 104 is wound. Opposing ends of the lace 104 are coupled with the reel assembly's spool so that operation of the tightening mechanism simultaneously tensions the opposing ends of the lace. Some conventional systems include a single lace end that is coupled with the reel assembly's spool so that operation of the tightening mechanism tensions only a single end of the lace. As shown in FIG. 15A, in some embodiments the lace 1506 may pass through a lumen 1504 of the spool 1502 so that the opposing lace ends are attached together and not directly attached to the spool 1502. In such embodiments, the lace 1506 may be shifted (i.e., shown by the arrows) through or within the spool's lumen 1504, which could allow the length of the lace 1506 in an upper and/or lower portion of the shoe 1500 to be adjusted, thereby enabling differential tightening of the shoe 1500 as described herein below. The opposing ends of the lace 1506 may be coupled together along the lace path, or within the spool 1502, via an attachment mechanism 1508.

Figure 15B:
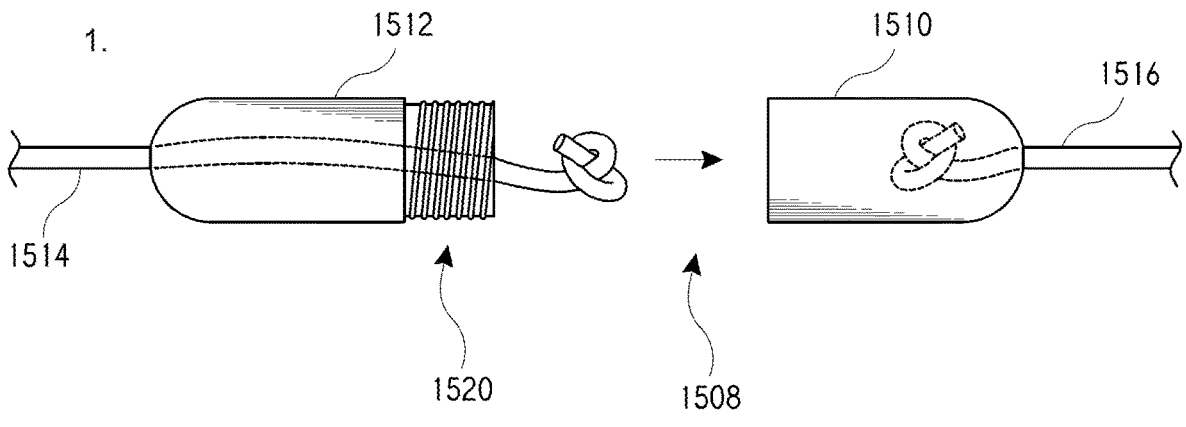
FIGS. 15B-C illustrate embodiments of attachment mechanisms that may be used to attach or couple opposing ends of a lace.
Figure 15B:
Figure 15C:
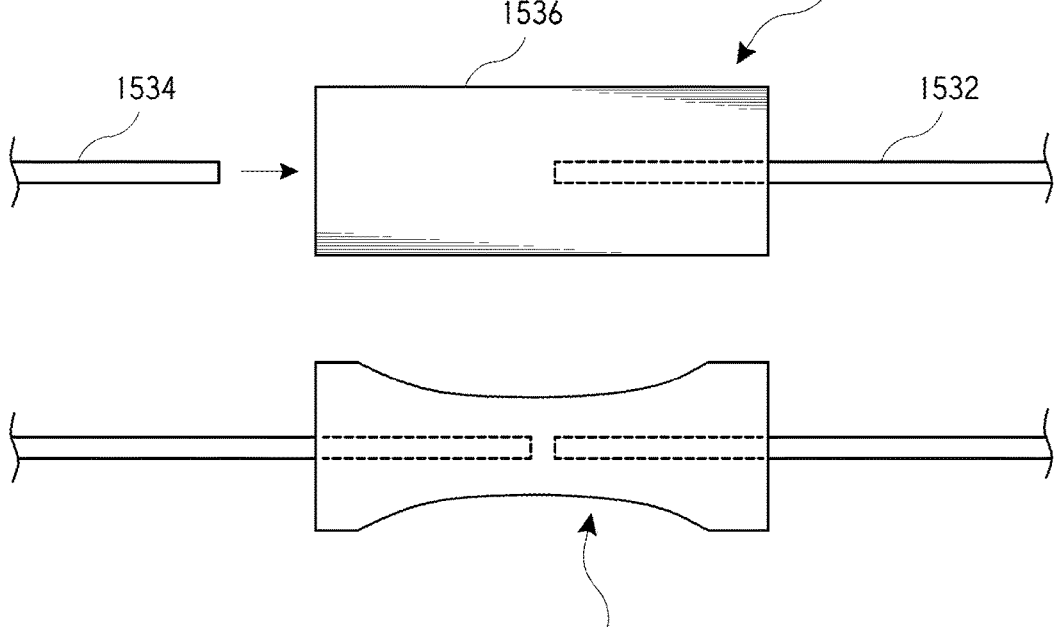

FIGS. 15B and 15C illustrate embodiments of attachment mechanisms 1508 that may be used to attach or couple opposing ends of lace 1506. In FIG. 15B, a first lace end 1516 may be coupled with one end 1510 of the attachment mechanism 1508 while a second lace end 1514 is coupled with another end 1512 of the attachment mechanism 1508. The two ends, 1510 and 1512, of the attachment mechanism 1508 may then be coupled together via threading 1520 or some other mechanism. In FIG. 15C, a first lace end 1532 may be inserted within one end of a ferrule 1536 and a second lace end 1534 may be inserted within an opposite end of the ferrule 1536. The ferrule 1536 may then be crimped together 1538 to lock the lace ends, 1532 and 1534, within the ferrule 1536.

Referring again to FIG. 1, the reel assembly 102 is positioned on the side of the shoe 100 and may be removed or remote from the shoe's eyestay by a distance X. In other embodiments, the reel assembly 102 may be directly adjacent or in contact with an edge of the eyestay. In yet other embodiments, the reel assembly 102 may be "remote" mounted within the outsole or midsole of the shoe 100. Although the reel assembly 102 is illustrated as being positioned on the medial side of the shoe 100, in other embodiments the reel assembly 102 could be positioned on the lateral side of the shoe 100. Other tightening mechanism may include pull cords having a portion or component that may be grasped and pulled by a user. Still other components may be used to tighten the lace 104. Exemplary reel based closure devices are further described in U.S. application Ser. No. 14/297,047, filed Jun. 5, 2014, entitled "Integrated Closure Device Components and Methods"; exemplary pull cord based devices are further described in U.S. application Ser. No. 14/166,799, filed Jan. 28, 2014, entitled "Lace Fixation Assembly and System," the entire disclosures of which are incorporated by reference herein.

The lace 104 is positioned about a tongue portion of the shoe 100 along a lace path that traverses from an upper portion of the shoe 100 to a lower portion of the shoe 100. The lace 104 is guided along the lace path via a plurality of first guides 112 and second guides 110. The first guides 112 include channels or lumens about which the lace 104 slides. In some embodiments, the second guides 110 are tubing through which the lace 104 is disposed. The lace 104 is positioned about the tongue portion of the shoe 100 so that the lace crossings are roughly parallel to one another and roughly orthogonal of the shoe's eyestay. This configuration results a greater degree of lace tension being used to pull the opposing eyestays of the shoe closed since the lace tension is directed in the direction of closure of the tongue portion.

As described above, the lace 104 is able to dynamically shift relative to the shoe 100 by sliding within the first and/or second guides, 112 and 110. The lace 104 may have a small diameter that reduces friction between the lace and guides. The guides and/or lace may also be made of a relatively low friction material to reduce wear between these components.

The lace 104 is positioned about the tongue portion of the shoe so as to form a first or upper tightening zone $Z_1$ and a second or lower tightening zone $Z_2$. The first or upper tightening zone $Z_1$ is formed from an upper lace portion 106 that exits the reel assembly 102 via tubing 110 and traverses multiple times, via guides 112, across an upper portion of the shoe 100 between the shoe's opposing eyestays. FIG. 1 specifically illustrates the upper lace portion 106 traversing three times across the upper portion of the shoe 100, although the upper lace portion 106 may traverse more or fewer times as desired. After the upper lace portion 106 traverses across the upper portion of the shoe 100 the third time (or any other number as desired), the upper lace portion 106 is routed to a distal end of the shoe 100 via tubing 110. The second or lower tightening zone $Z_2$ is formed from a lower lace portion 108 that exits the reel assembly 102 via tubing 110 and traverses multiple times, via guides 112, across a lower portion of the shoe 100 between the shoe's opposing eyestays. As with the upper zone $Z_1$, FIG. 1 illustrates the lower lace portion 108 traversing three times across the lower portion of the shoe 100. The lower lace portion 108 converges with the upper lace portion 106 at the distal end of the shoe 100.

As illustrated in FIG. 1, the upper lace portion 106 traverses along the upper portion of the shoe's lace path immediately after exiting the tightening mechanism 102 while the lower lace portion 108 traverses about midway or lower along the shoe's lace path immediately after exiting the tightening mechanism 104. This lacing configuration is different than conventional lacing systems where both portions of the lace immediately exiting a tightening mechanism traverse across and tighten the upper portion of the shoe first. The lace configuration of FIG. 1 (i.e., one lace portion that traverse along the upper portion of the shoe and one lace portion that traverse along roughly the middle or lower portion of the shoe) reduces dynamic shifting of the lace and enables a relatively uniform closure and/or tightening of the shoe about a user's foot. This effect is achieved, in part, because the lace immediately exiting the tightening mechanism 102 (i.e., the portion of lace having the greatest tension) is immediately routed to or along both the upper portion and along roughly the middle or lower portion of the shoe. Since the lace tension is greatest in both the upper and middle portions of the shoe 100 and since the upper lace zone $Z_1$ and lower lace zone $Z_2$ each include three lace crossings, the tension in each lace zone, $Z_1$ and $Z_2$, and/or the frictional loss experienced in the upper and lower zones is roughly uniform, which results in a more uniform tensioning or tightening of the upper and lower zones, $Z_1$ and $Z_2$. In conventional systems, since both portions of the lace immediately exiting the tightening mechanism traverse and tighten the upper portion of the shoe, the frictional lace tension loss experienced at the distal end of the shoe is increased, which may result in a non-uniform tightening of the upper and lower portions of the shoe, such as tightening of the upper portion first and subsequent tightening of the lower portion.

The lacing configuration of FIG. 1 also reduces dynamic shifting of the lace due to the lace tension being greatest along both the upper portion and along roughly the middle or lower portion of the shoe. For example, as the user's foot shifts within the shoe 100 and pushes against upper and/or lower portions of the shoe 100, the positioning of the upper lace portion 106 and lower lace portions 108 counteracts and limits a dramatic increase in lace tension in the upper and lower zones, $Z_1$ and $Z_2$, which limits dynamic shifting of the lace. Because dynamic shifting of the lace is reduced, the fit of the shoe 100 about the user's foot is stabilized.

One of the effects of the lace configuration of FIG. 1 is that the lowest tensioned portion of the lace is positioned on the side of the shoe 100 rather than at the distal end of the shoe (e.g., the toe portion of the shoe). For example, as shown in FIG. 1, lace portion 114 is the portion of lace 104 that experiences the lowest lace tension due to frictional losses from the guides 112. Lace portion 114 is positioned on the lateral side of the shoe between, and at a distal end of, the upper zone $Z_1$ and lower zone $Z_2$. In conventional systems, the lace that corresponds to lace portion 114 is typically positioned roughly orthogonal to the shoe's eyestay at a distal of the lace path, such as adjacent or near the shoe's toe box. Since lace portion 114 is positioned on the side of the shoe 100 rather than at the distal end of the lace path (e.g., near the toe box), the tension in the upper and lower zones, $Z_1$ and $Z_2$, is relatively more uniform. In some embodiments, a pull tab (See FIGS. 22B, 30, and 34) may be coupled with lace 106 and 108 adjacent the tubing 110. The pull tab may be grasped and pulled by a user to facilitate in pulling the lace 104 from the reel assembly 102. The pull tab may aid in more uniform removal of the lace 104 from the spool and reel assembly 102.

Another aspect of the non-symmetrical lace configurations described herein is that the shoe or article includes at least one lace guide that is positioned laterally offset or outward of another lace guide and that includes a longitudinal path that is greater than the other lace guide. For example, FIG. 1 illustrates lace portion 114 (i.e., the guide that directs the lace) positioned laterally outward of a first guide 112b. In some embodiments, the first guides of the shoe 100 (i.e., the combination of first guides 112 and 112b) may define a lateral tensioning zone $T_z$, or a zone in which a tension force is exerted to pull an opening (e.g., a tongue portion) of the shoe 100 closed. The lace portion 114 may be positioned laterally outward of the tensioning zone $T_z$ so as to avoid interfering with tensioning of the shoe 100.

FIG. 1 also illustrates that a longitudinal length $L_1$ of the lace portion 114 is greater than a longitudinal length $L_2$ of the first guide 112b such that opposing ends of the first guide 112b are disposed within or between the opposing ends of the lace portion 114. As illustrated in various embodiments herein, the longitudinal length of the lace guide that corresponds to lace portion 114 may be greater than multiple guides (i.e., 2 or more guides) depending on how far the lace is routed along the side of the lace path. In addition, in the other illustrated embodiments, the lace guide corresponding to lace portion 114 may be made of a pair of webbing guides, or any other type of guide that is configured to route the lace. The lace that is routed through the lace portion 114 may be substantially parallel to the lace that is routed through the first guide 112b.

Figure 2:
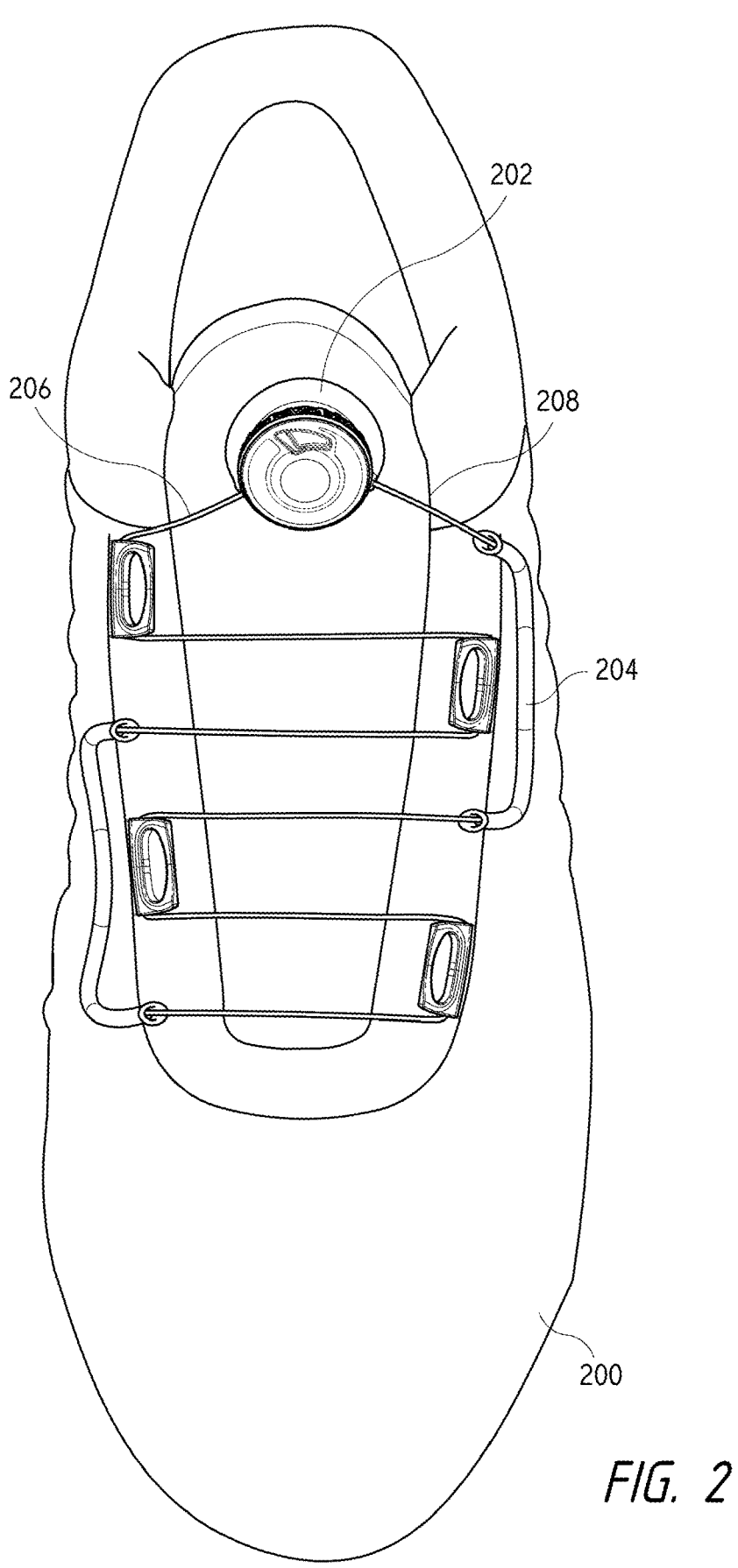
FIGS. 2-3 illustrate other embodiments of a lace path of a shoe that limits dynamic lace shifting of the lace and/or provides a more uniform tightening.

FIG. 2 illustrates a shoe 200 having a lacing system configuration that is similar to that illustrated in FIG. 1. The main difference between FIG. 1 and FIG. 2 is that the tightening mechanism 202 of FIG. 2 is positioned on the shoe's tongue rather than on the side of the shoe. Positioning the tightening mechanism 202 on the shoe's tongue may result in a more uniform ejection of the lace from the tightening mechanism's interior. For example, referring briefly to FIG. 1, when the tightening mechanism is positioned on the side of the shoe, opening the shoe's tongue can result in a greater length of the upper lace portion (i.e., 106) being ejected or pulled from the tightening mechanism than the lower lace portion (i.e., 108). A greater length of the upper lace portion is ejected due to the tongue being coupled with the shoe in a hinge type fashion and due to the tongue being opened in a pivot like manner, which results in greater opening of the upper portion than the lower portion. Since the upper and lower lace portions, 106 and 108, are both connected to the tightening mechanisms' spool, an equal length of the upper and lower lace portions is unwound from the spool and any non-ejected length of the lower lace portion remains disposed within the interior of the tightening mechanism. The non-ejected length of the lower lace portion may tangle or bind within the tightening mechanism's interior, or cause other minor lace tensioning issues. The configuration of FIG. 2 reduces lace ejection issues since the upper lace portion 206 and lower lace portion 208 are ejected in a more uniform manner.

As with the lacing configuration of FIG. 1, the upper lace portion 206 initially tensions and/or tighten the upper portion of the shoe 200 while the lower lace portion 208 initially tensions a mid or lower portion of the shoe 200. The lower lace portion 208 is immediately routed to the mid or lower portion of the shoe 200 via tubing 204 or any other type of guide.

Figure 3:
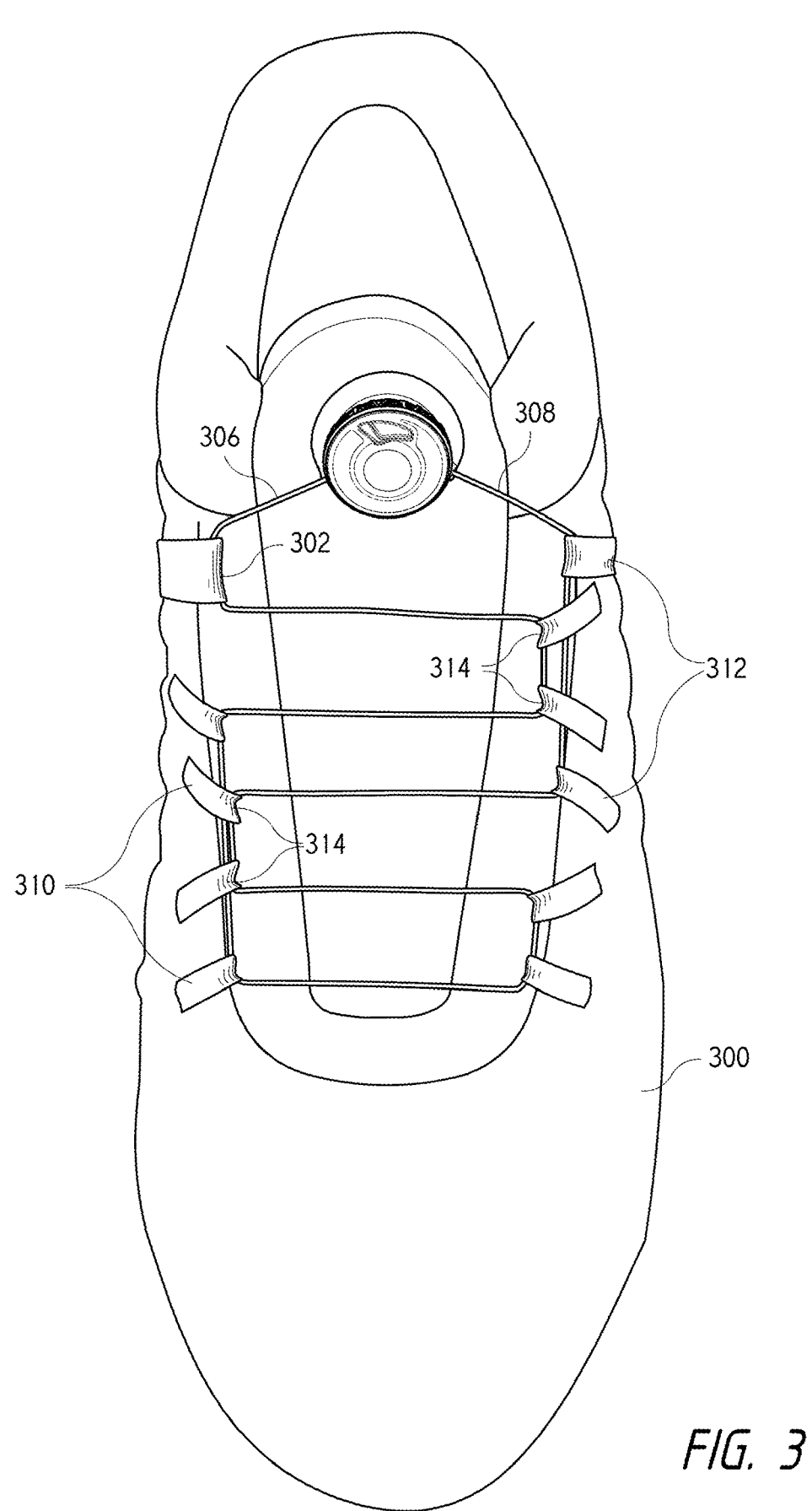

FIG. 3 is similar to the embodiment of FIG. 2, except that the upper lace portion 306 and/or lower lace portion 308 are guided about the shoe 300 via webbing guides 302 rather than plastic guides. The webbing guides 302 are typically constructed from a fabric or softer material than the plastic guides, which are typically constructed of more rigid materials that may create pressure points. After traversing the upper portion of the shoe 300 one or more times, the upper lace portion 306 is guided to the distal end of the shoe 300 via webbing guides 310, which function cooperatively in guiding the lace. Similarly, the lower lace portion 308 is immediately guided to the mid or lower portion of the shoe 300 via webbing guides 312 that function cooperatively in guiding the lace. An intermediate guide 314 that is positioned between the webbing guides 310 and/or 312 may function as lace tender or guide that limits contact between the lace and the shoe 300. As illustrated in FIG. 3, the webbing guides may function in pairs or in isolation to guide the lace about the lace path. When webbing guides are used in isolation, the webbing guides may be configured to conform as the lace is tensioned within the webbing guide. For example, opposing ends of the webbing guide may curve or deflect outward under tension. In addition, any or all of the guides illustrated in the embodiments may be visible on or near the eyestay edge of the shoe, or may be hidden under the eyestay edge.

Figure 4:
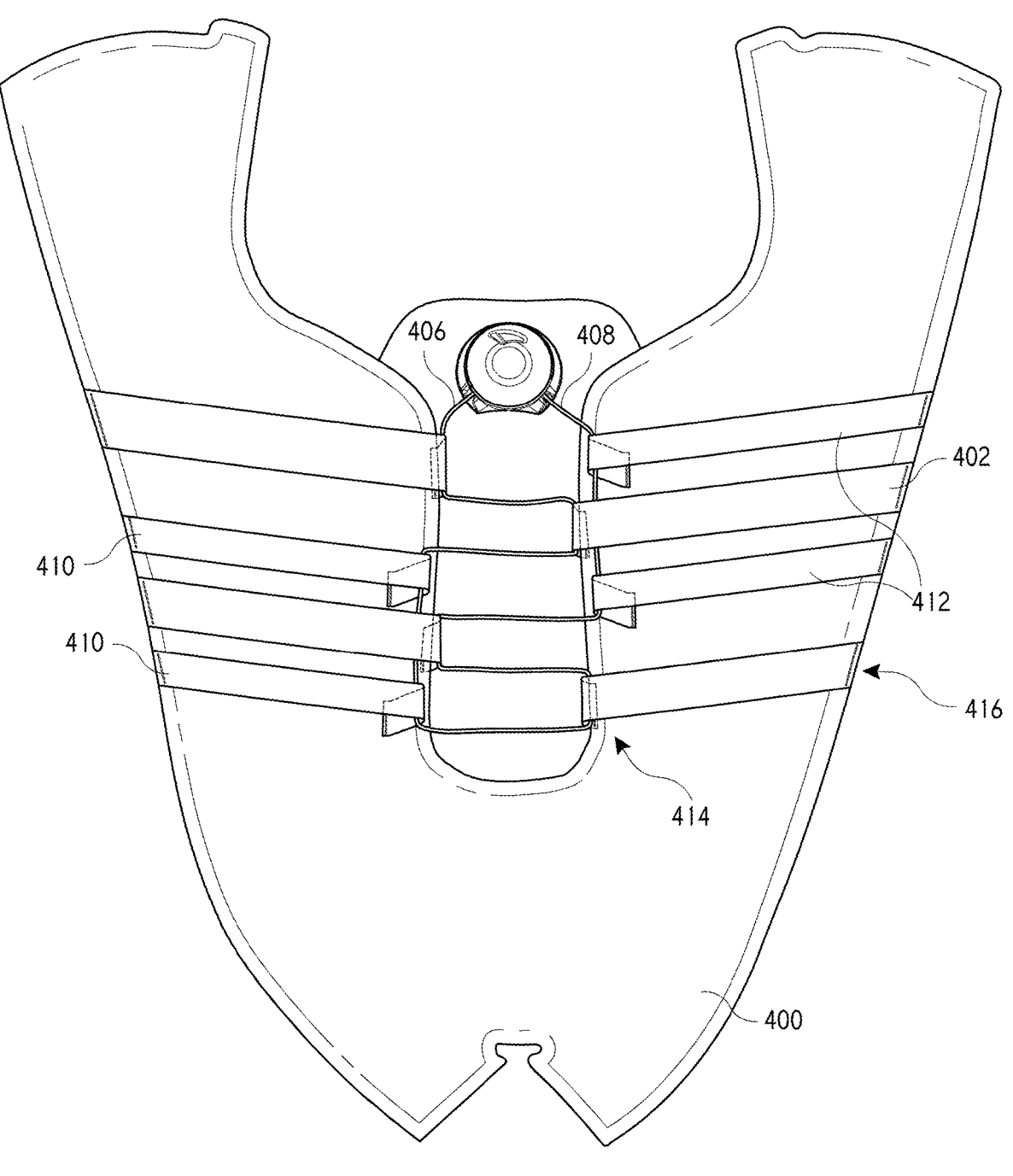
FIG. 4 illustrates another embodiment of a lace path, wherein the lace path is defined via straps that function as guides for the lace.

FIG. 4 is similar to the embodiment of FIG. 3, except that webbing straps 402 are used to guide the upper lace portion 406 and lower lace portion 408 rather than or in addition to the webbing guides. The webbing straps 402 are typically constructed from fabric or other relatively soft materials. A pair of webbing straps 410 may cooperatively route the upper lace portion 406 from the upper zone to the distal end of the shoe 400 while a pair of webbing straps 412 cooperatively route the lower lace portion 408 from the tightening mechanism to the mid or lower portion of the shoe 400. In some embodiments, a first end 414 of one or more webbing straps 402 may be attached to the shoe 400 at or near the shoe's eyestay while a second end 416 of the one or more webbing straps 402 is attached to the shoe 400 at or near an interface between the shoe's upper and the sole. The result may be that tension in the lace is transferred to the webbing strap 402, which pulls the shoe's opposing eyestay toward one another while simultaneously pulling the shoe's upper inward and against the user's foot. Additional details of attaching lacing guides near both the shoe's eyestay and sole are provided in U.S. application Ser. No. 14/877,755, filed Oct. 7, 2015, entitled "Devices, Methods, and Systems for Remote Control of a Motorized Closure System", the entire disclosure of which is incorporated by reference herein.

Figure 5:
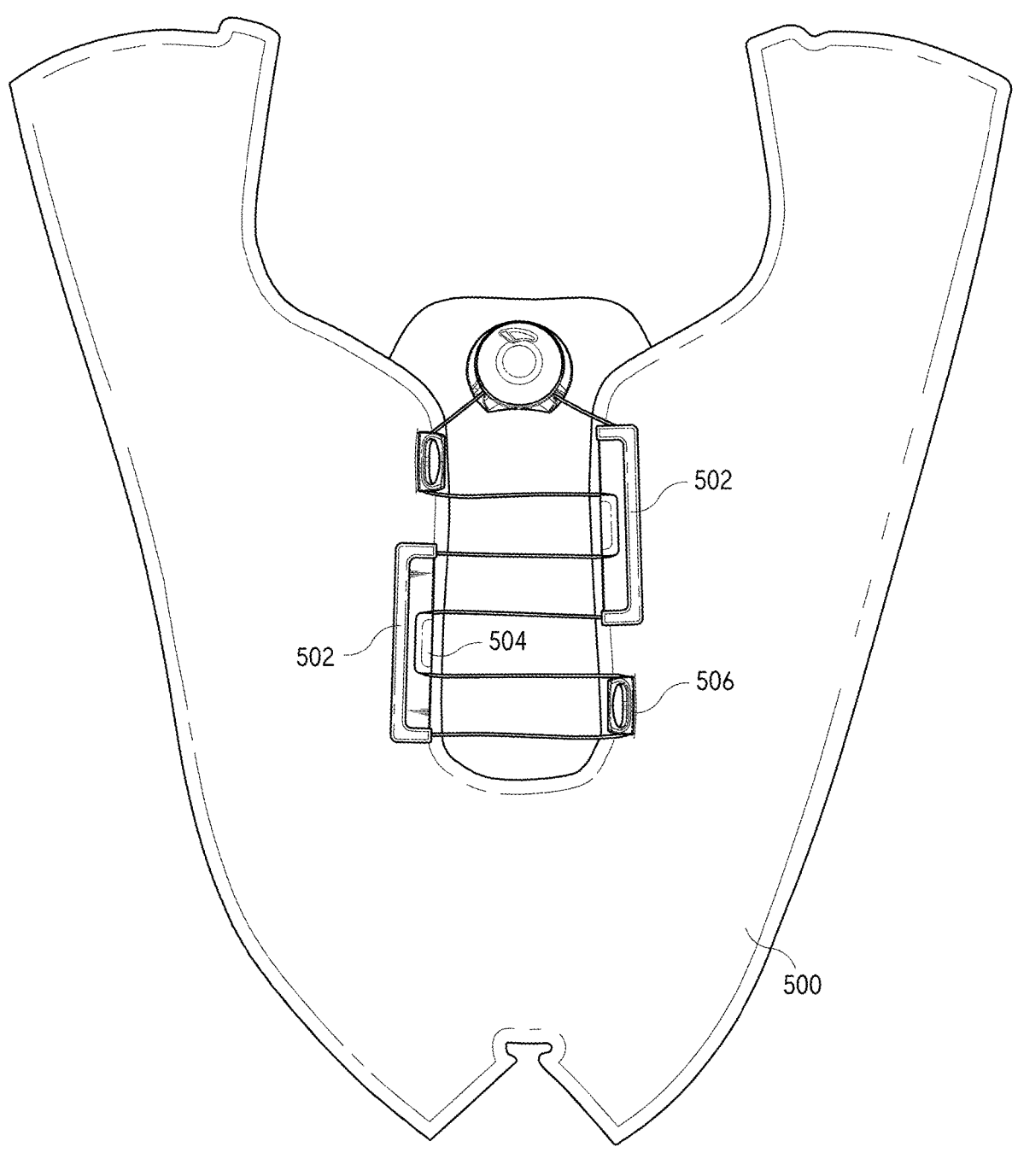
FIGS. 5-6 illustrate other embodiments of a lace path of a shoe that limits dynamic lace shifting of the lace and/or provides a more uniform tightening.

FIG. 5 is similar to the other embodiments described above, except that the shoe 500 includes a plurality of relatively rigid guides to guide the upper and lower lace portions about the shoe. Specifically, the shoe 500 includes an elongate guide 502 having an elongated mid portion to route the upper lace portion between the upper zone and distal end of the shoe 500 and/or to route the lower lace portion immediately from the tightening mechanism to the mid or lower portion of the shoe 500. The shoe 500 also includes a first and/or second relatively short guide 504 and/or 506 that route the respective lace portion in the upper and/or lower zones. In some embodiments, the elongate guide 502 and/or first/second short guides (504 and/or 506)

may have an open channel or back portion that allows the lace to be placed within the guide and/or removed therefrom as desired.

Figure 6:
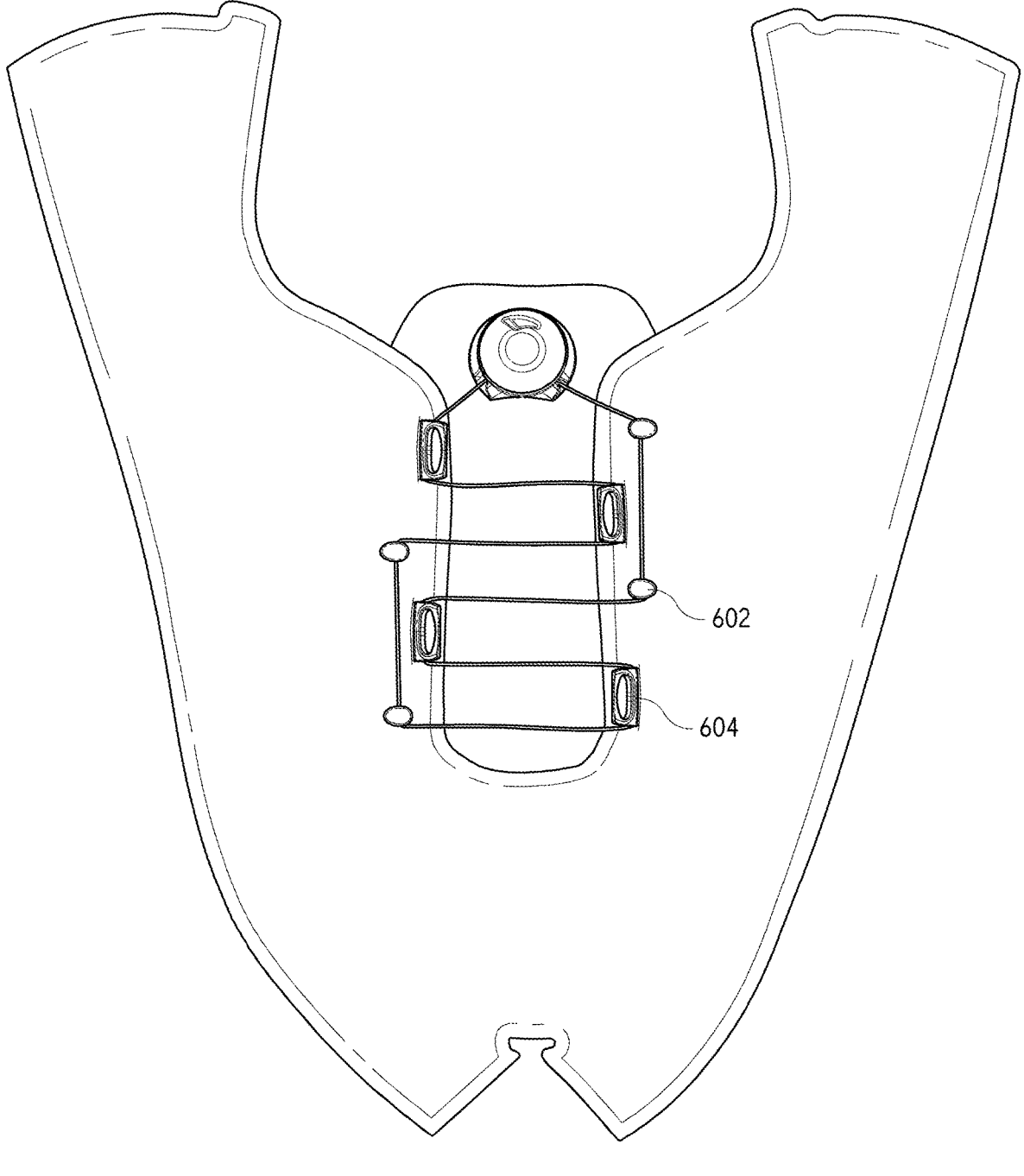

FIG. 6 is similar to FIG. 5, except that the elongate guides 502 are replaced with guide posts 602 around and about which the lace is positioned. The guide posts 602 include a pair of posts that function cooperatively to route the upper lace portion between the upper zone and the distal end of the shoe 600 and/or to route the lower lace portion from the tightening mechanism to the mid or lower portion of the shoe 600. The shoe 600 may also include one or more shorter guides 604 that route the lace within the upper and/or lower zones. It should be realized that a shoe may include any combination of the guides illustrated in FIGS. 3-6 as desired.

Figure 7:
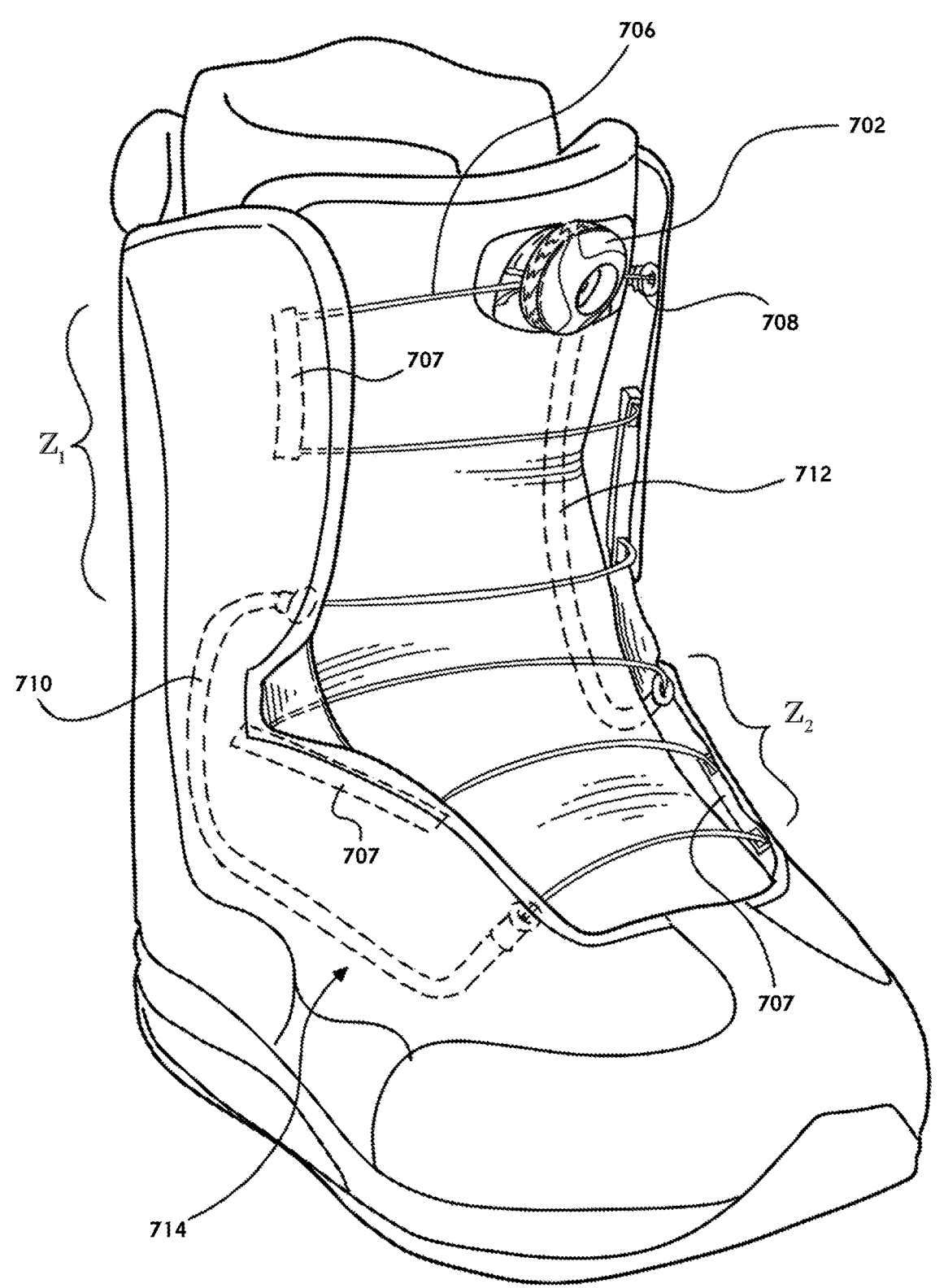
FIGS. 7-8 illustrate the lacing configurations described herein applied to a boot or high-top shoe.
Figure 8:
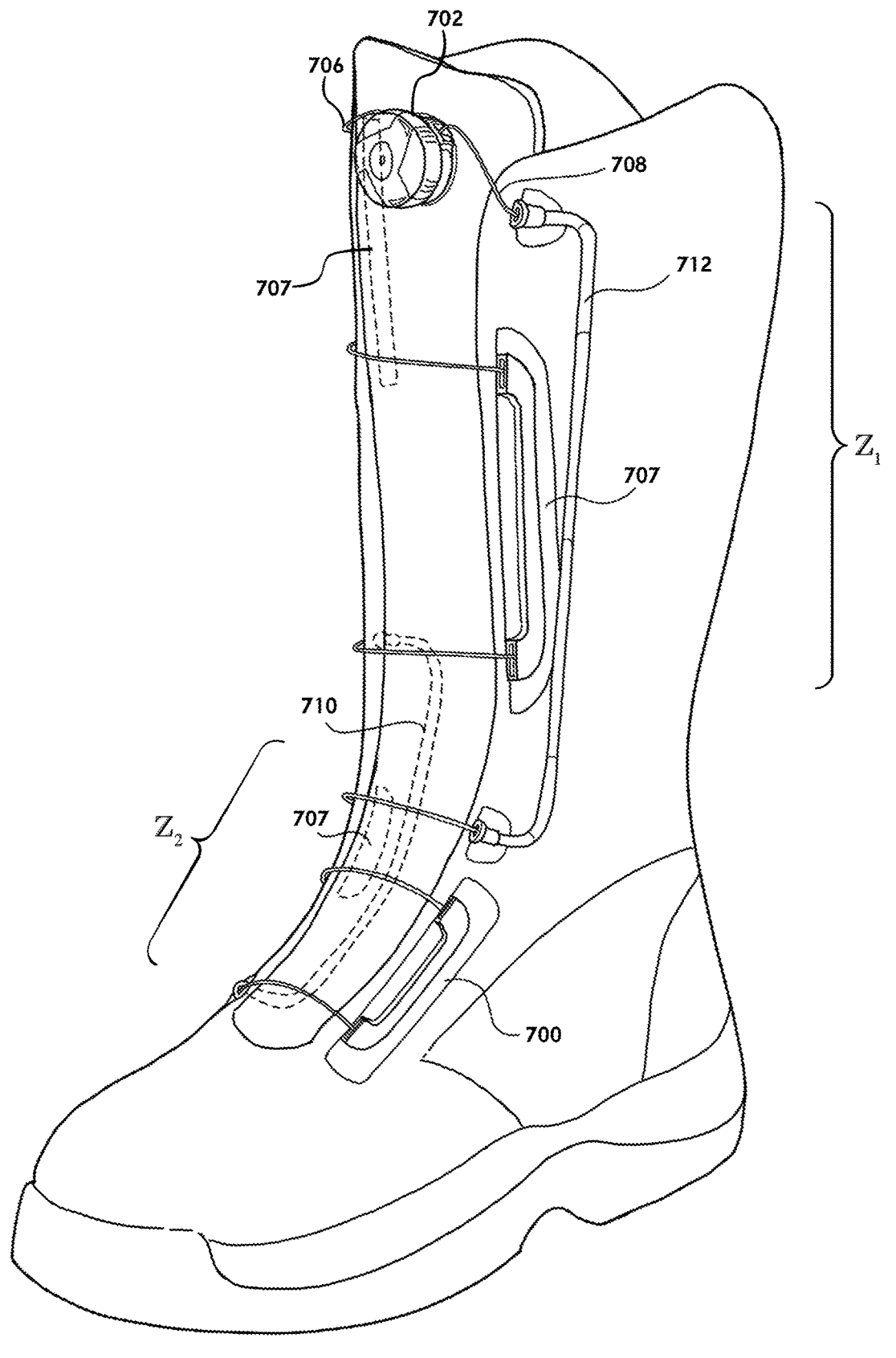

FIGS. 7 and 8 illustrate the lacing configuration described above as applied to a boot, such as a snowboard boot (FIG. 7) or work boot (FIG. 8). The boots include a tightening mechanism 702 that is operable to tension an upper lace portion 706 and a lower lace portion 708. The upper lace portion 706 affects tensioning in an upper zone $Z_1$ while the lower lace portion 708 affects tensioning in a lower zone $Z_2$ as previously described. A first elongate guide 710 (e.g., tubing) is positioned about the boot to route the upper lace portion 706 between the upper zone $Z_1$ and the distal end of the boot or lace path. A second elongate guide 712 is configured to route the lower lace portion 708 immediately from the tightening mechanism 702 to the mid or lower portion of the boot or lace path. A plurality of additional guides 707 are positioned about the boot to guide the upper and lower lace portions in the upper and lower zones, $Z_1$ and $Z_2$. The guides 707 may have relatively elongate or short configurations as desired. In some embodiments, all or some of the guides (i.e., 707, 710, and 712) are disposed under an outer layer of the boot and/or between layers of the boot, so that the guides are hidden from view. The lacing configurations of FIGS. 7 and 8 result in the portion of lace 714 having the lowest lace tension being positioned on the medial or lateral side of the boot.

Figure 9A:
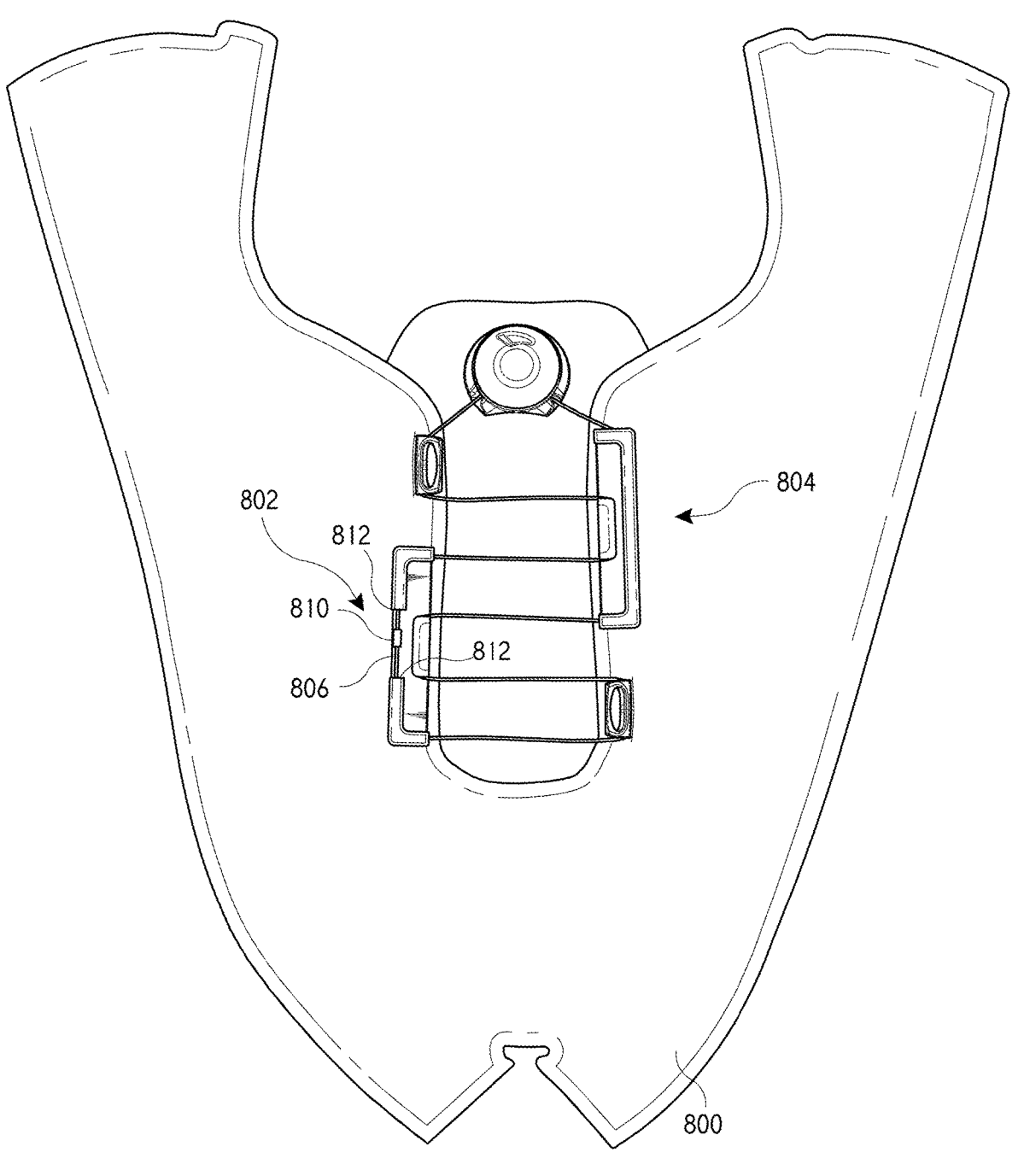
FIGS. 9A-10 illustrate a guide that includes a stop component that further minimizes or prevents shifting of the lace.
Figure 9B:
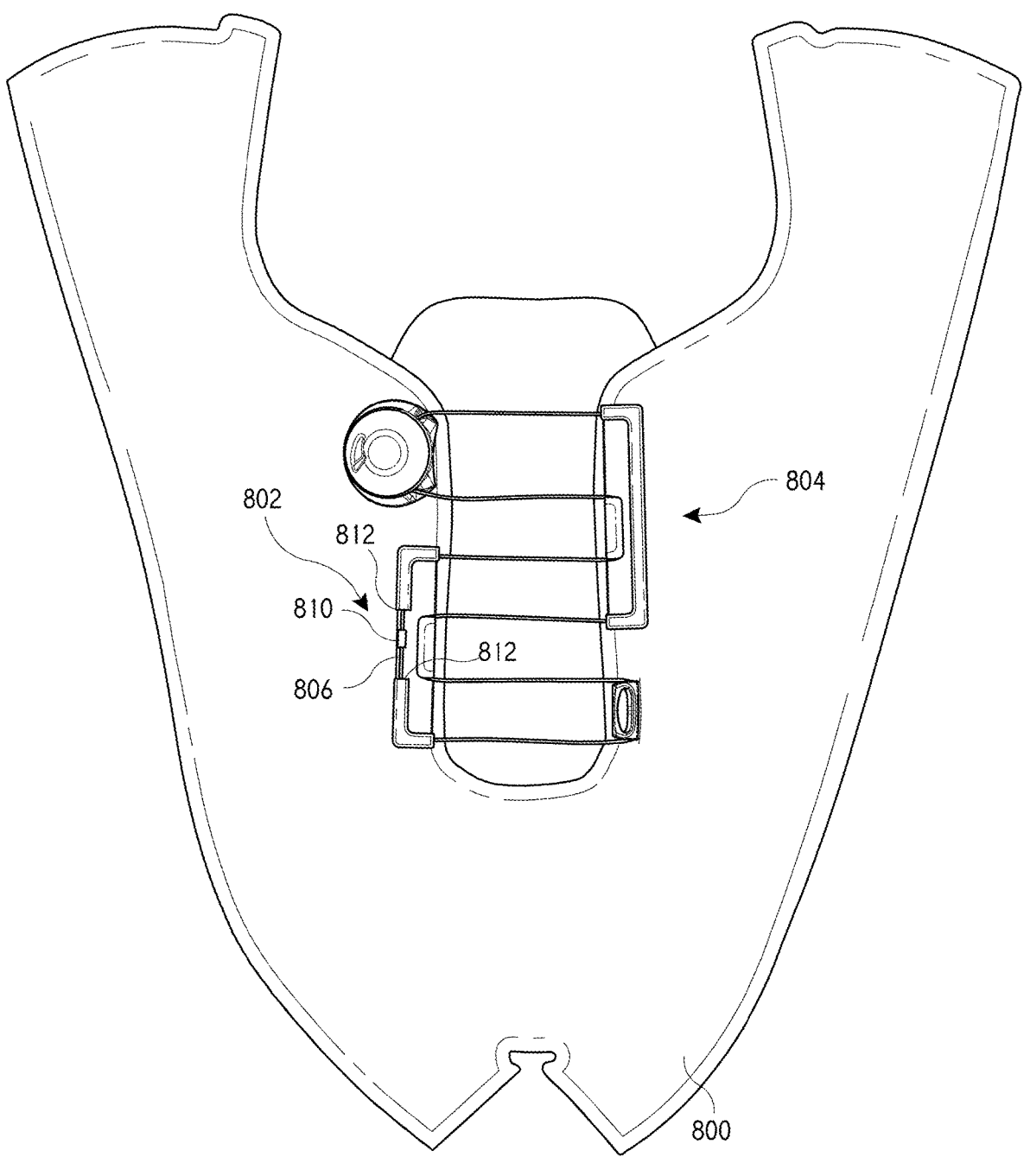
Figure 10:
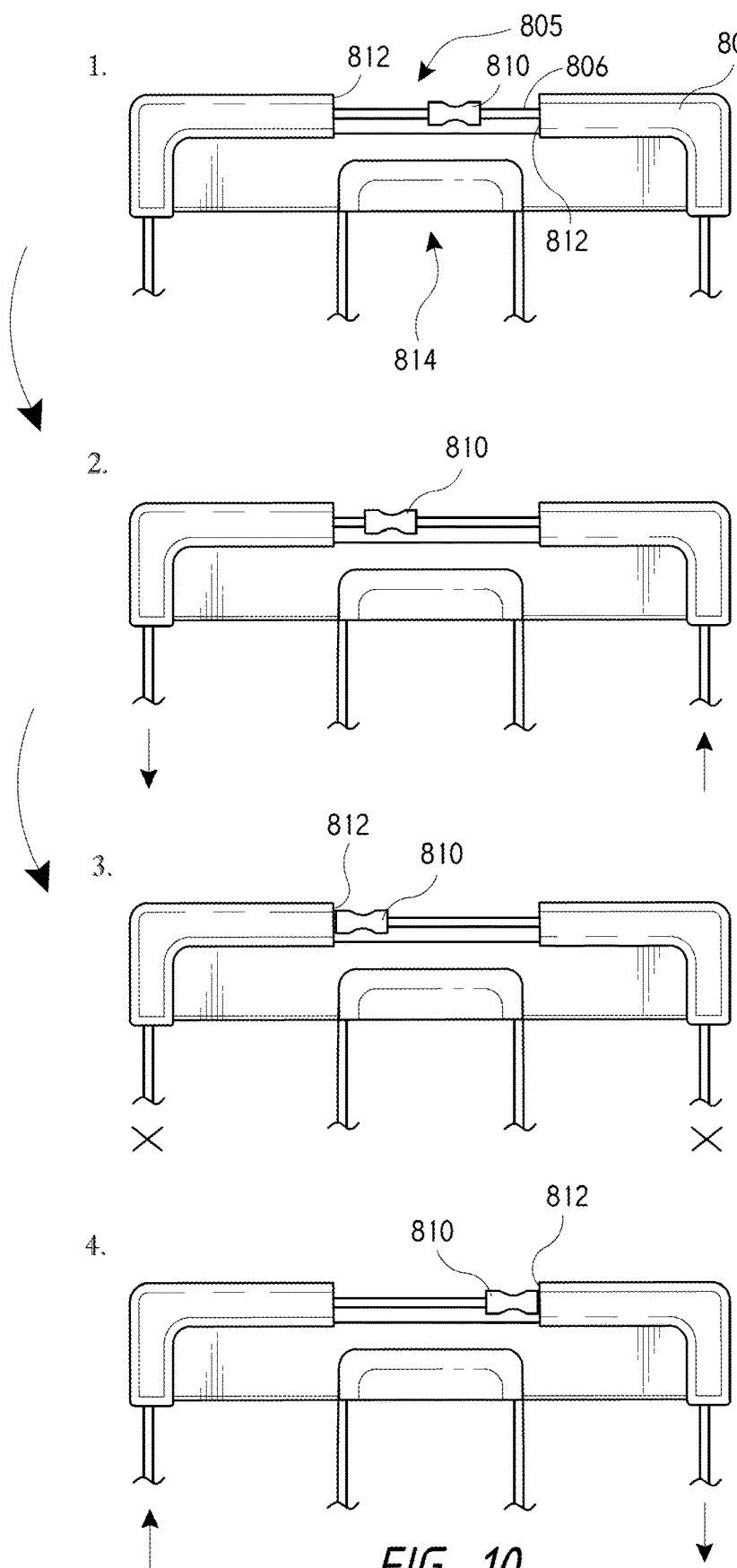

FIGS. 9A, 9B, and 10 illustrate a guide that includes a stop component that further minimizes or prevents shifting of the lace. Specifically, an elongate guide 802 that is used to route the upper lace portion 806 from the upper zone to the distal end of the shoe 800 includes a mid-section 805 where the lace is exposed. A stop component 810 is coupled with the lace in the mid-section 805 of guide 802. The stop component 810 minimizes or prevents shifting of the lace by contacting opposing inner edges (e.g., edge 812) of the mid-section 805 of guide 802 as illustrated in FIG. 10. Minimizing or preventing shifting of the lace stabilizes the fit of the shoe 900 about a user's foot. In some embodiments, the guide 802 may include an inner guide portion 814 that guides the lace within the lower zone. The elongate guide 804 that routes the lower lace portion from the tightening mechanism to the mid or lower portion of the shoe 800 may similarly include a stop component and/or inner guide portion as well if desired.

FIG. 9A illustrates the tensioning mechanism positioned centrally on the shoe's tongue while FIG. 9B illustrates the tensioning mechanism positioned on the shoe's eyestay. In some instances it may be preferred to position the tensioning mechanism on the eyestay rather than on the tongue to minimize shifting of the tongue about the shoe. For example, in some instances, when the tensioning mechanism is positioned on the tongue, engagement of the stop component 810 with an inner edge 812 of the guide's mid-section 805 may cause the tensioning mechanism to pull the shoe's tongue toward one side of the shoe thereby causing the tongue to shift within the shoe. Positioning of the tensioning mechanism on the eyestay eliminates or minimizes shifting of the shoe's tongue since the tensioning mechanism is not directly coupled with the tongue.

Figure 11:
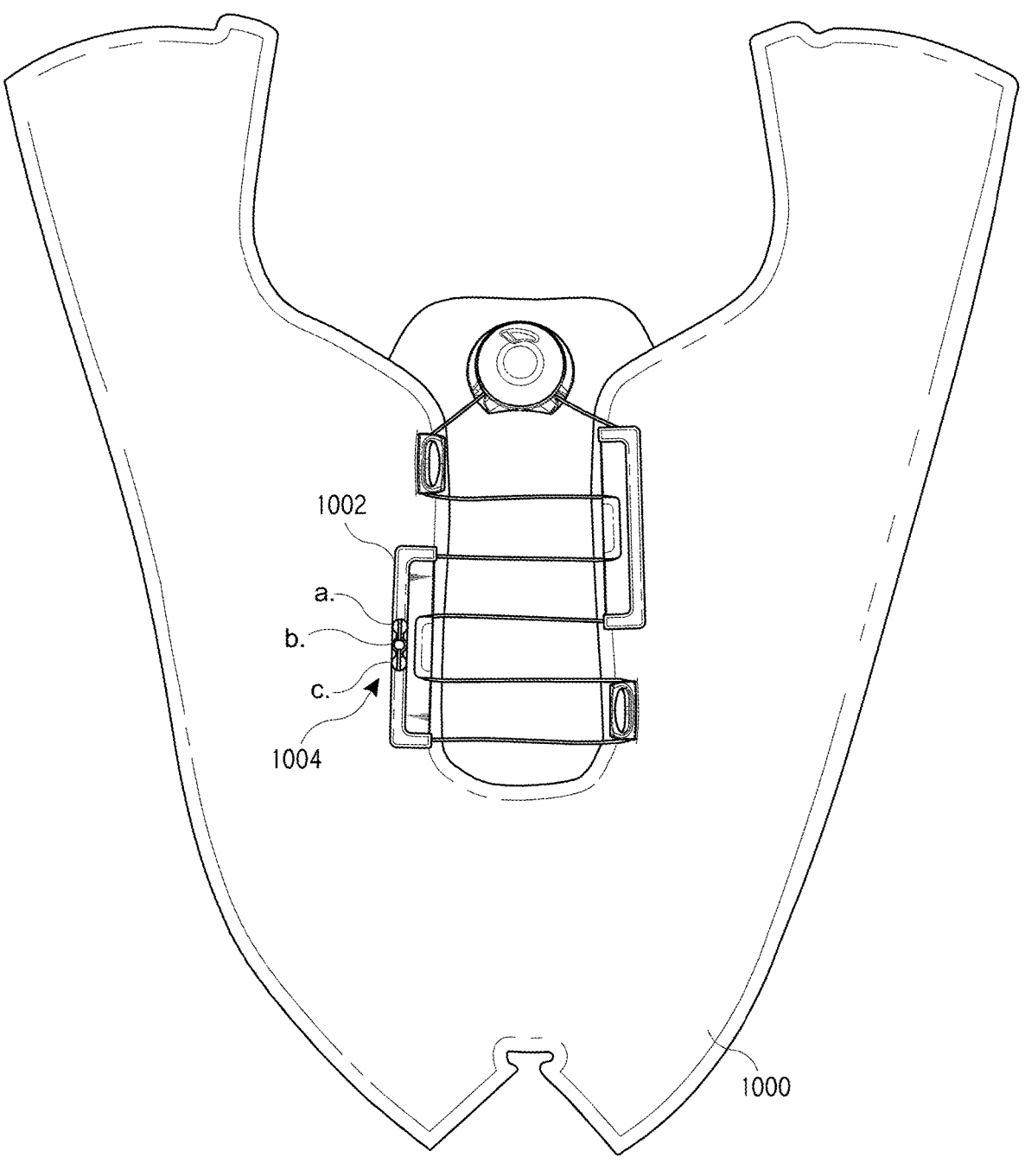
FIGS. 11-13 illustrate a guide that includes a component that prevents shifting of the lace and allows differential tension to be applied to the upper and lower zones.
Figure 12:
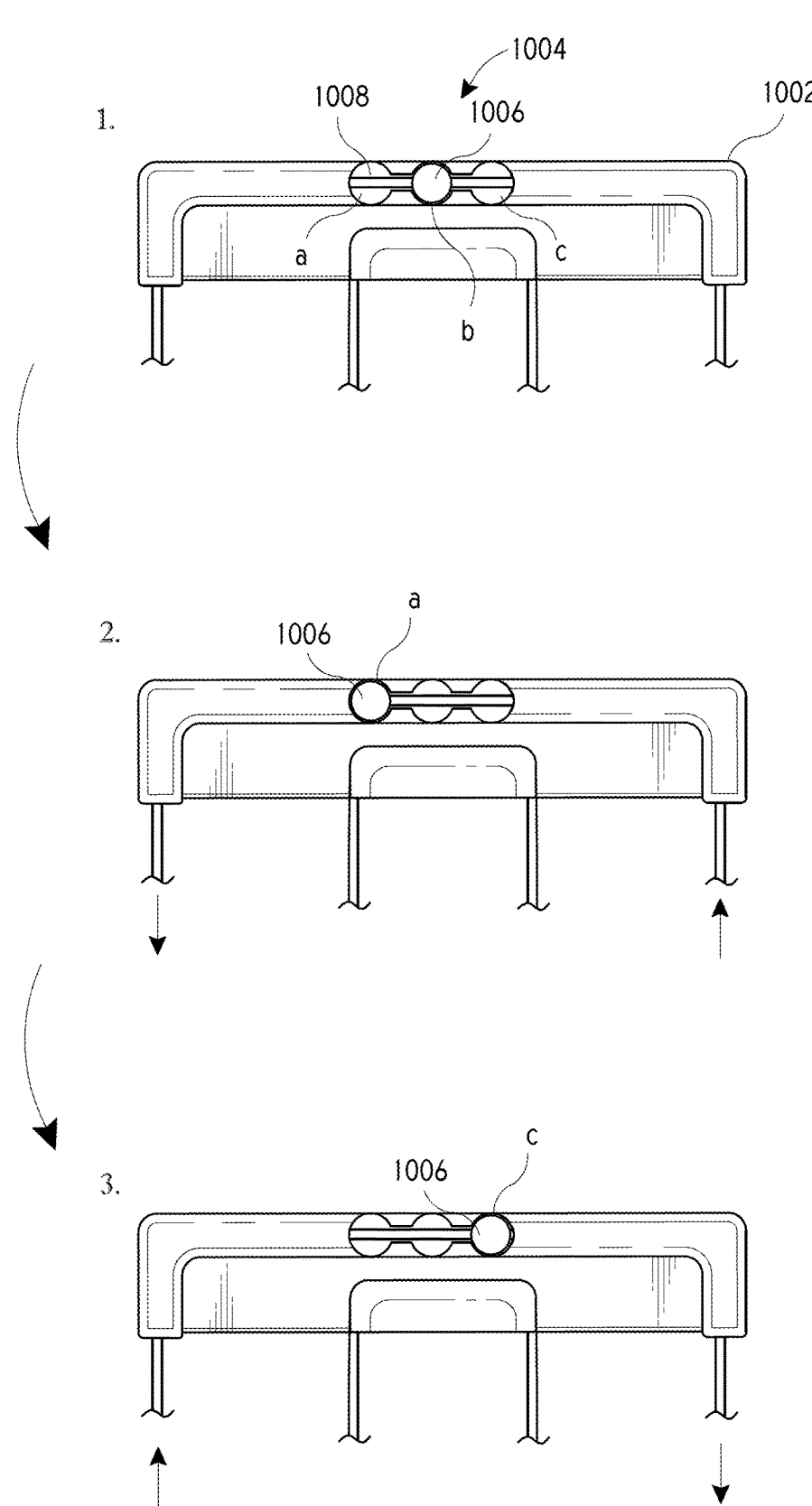
Figure 13:
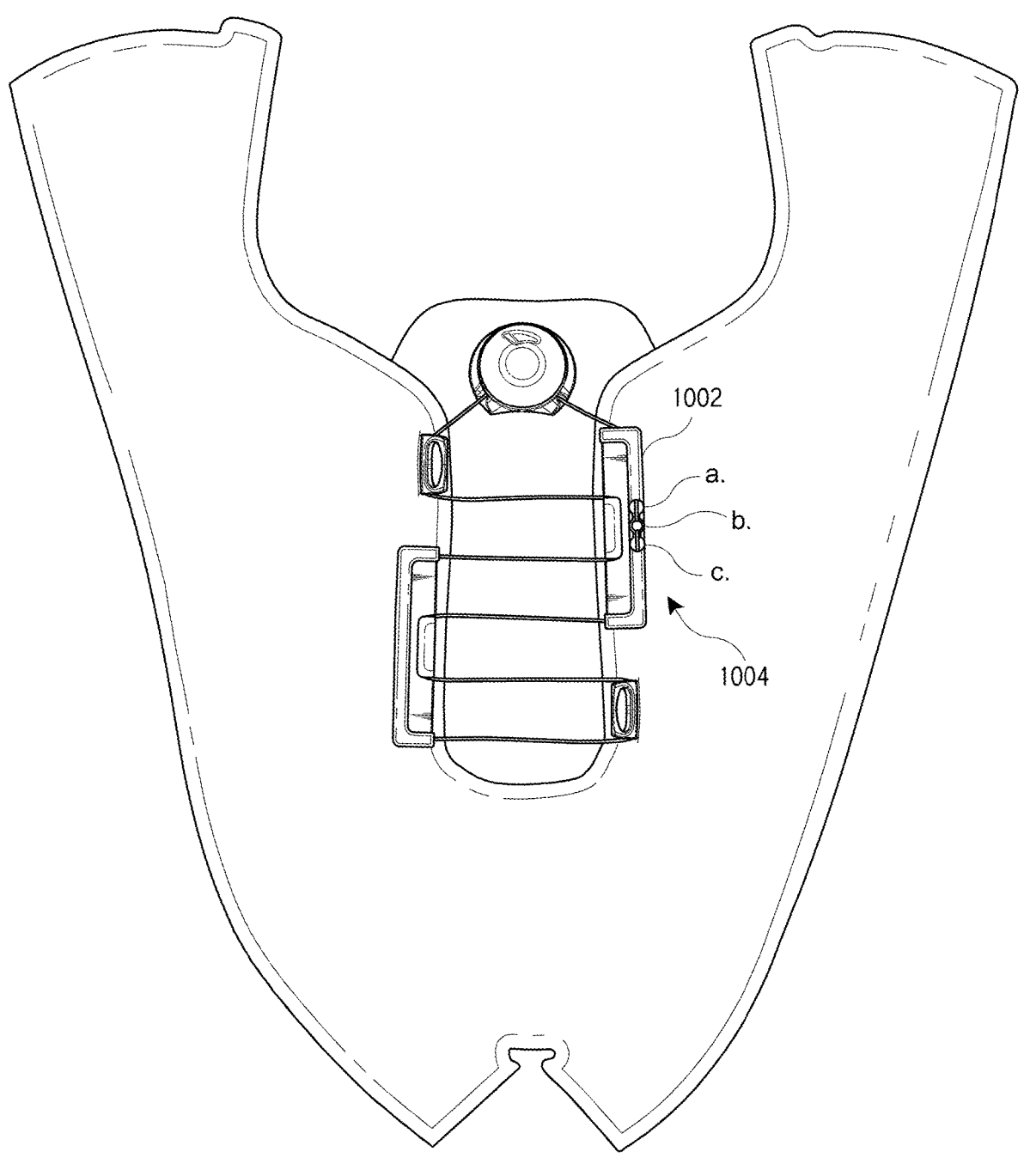

FIGS. 11-13 illustrate a guide that includes a component that prevents shifting of the lace and allows differential tension to be applied to the upper and lower zones. Specifically, an elongate guide 1002 that is used to route the upper lace portion 1008 from the upper zone to the distal end of the shoe 1000 includes a differential tensioning mechanism 1004. The tensioning mechanism 1004 includes a tensioning component 1006 that is positionable within one of a plurality of tensioning positions of guide 1002 (i.e., illustrated positions a, b, and c). In some embodiments, the tensioning component 1006 is a cylindrical or spherical member that may be moved and positioned within a cylindrical or spherical aperture. The tensioning component 1006 may be moved between positions a, b, and c by pushing the tensioning component 1006 downward or pulling the tensioning component 1006 upward and out of a cylindrical or spherical aperture and repositioning the tensioning component 1006 in a desired cylindrical or spherical aperture as illustrated in FIG. 12 (e.g., within aperture a, b, or c).

Contact between the tensioning component 1006 and a respective cylindrical or spherical aperture prevents shifting of the lace relative to the guide 1002 and shoe 1000. Positioning the tensioning component 1006 in a respective cylindrical or spherical aperture also lengths or shortens the lace in the upper and lower by some degree, which results in differential tensioning or tightening of the upper and lower zones upon operation of the tightening mechanism. For example, positioning the tensioning component 1006 in position "a" may shorten the length of lace in the upper zone in comparison with the lower zone and thereby effect increased tightening of the upper zone. In contrast, positioning the tensioning component 1006 in position "c" may shorten the length of lace in the lower zone in comparison with the upper zone and thereby effect increased tightening of the lower zone. Further, positioning the tensioning component 1006 in position "b" may roughly equalize the length of lace in the upper and lower zones thereby effecting roughly uniform tightening of the upper and lower zones. In this manner, a user may effect differential tightening of the shoe's upper and lower zones as desired. The elongate guide 1002 and tensioning mechanism 1004 may be positioned near a distal end of the shoe (i.e., near the shoe's toe region) as shown in FIG. 11 and/or may be positioned near a proximal end of the shoe (i.e., near the shoe's tongue or collar) as shown in FIG. 13. Although positioning the tensioning component 1006 in one of the respective positions is described as increasing or decreasing the length in the respective zones, it should be realized that repositioning of the tensioning component 1006 in the respective zones effectively results in a different tension within the respective zones due to shifting of the lace. Operation of the tensioning mechanism results in further differential tensioning of the respective zones.

Figure 14A:
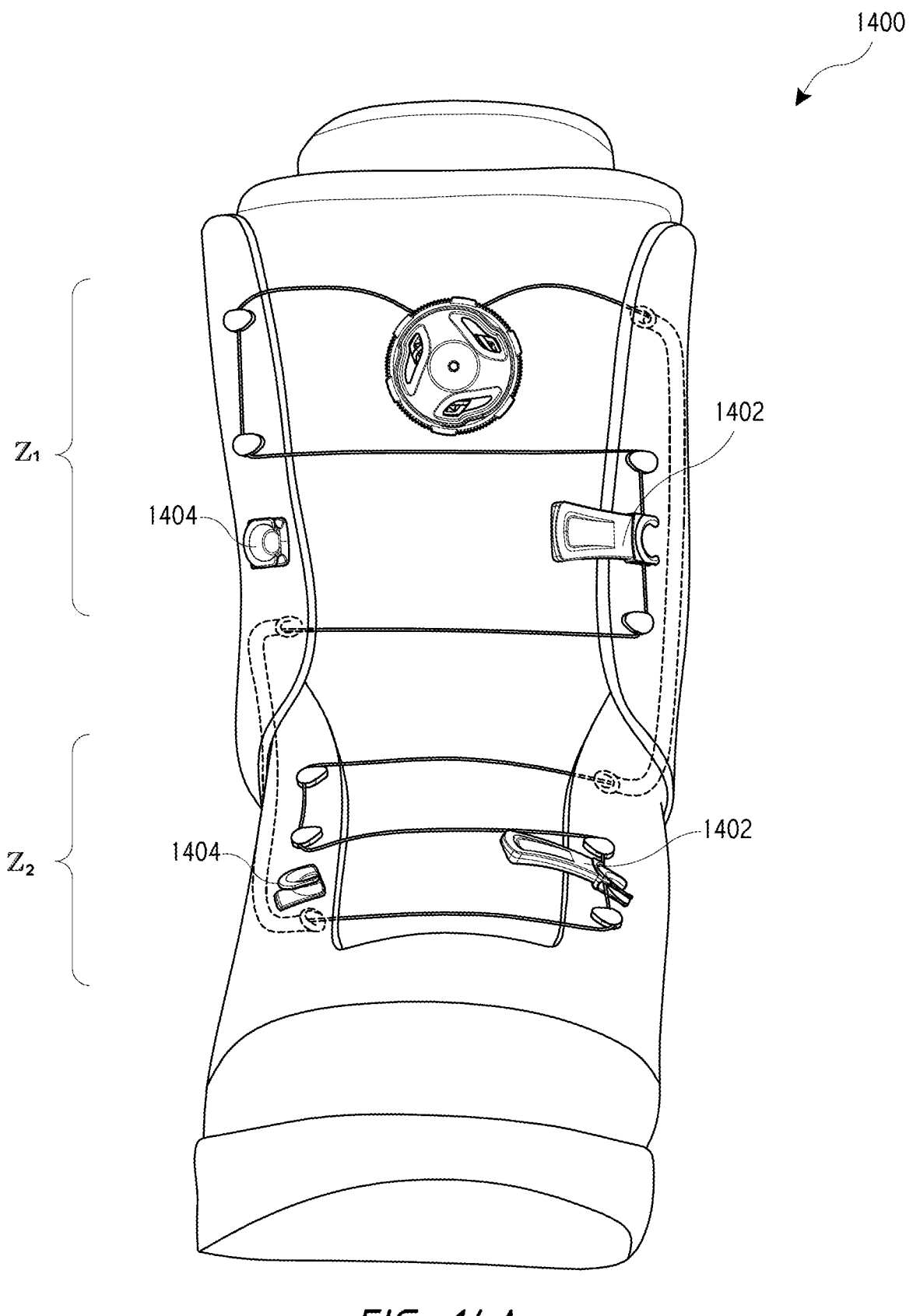
FIGS. 14A-B illustrate a lacing configuration applied to a boot that includes an additional component that may be used to increase the lace tension in one or more tensioning zones.
Figure 14B:
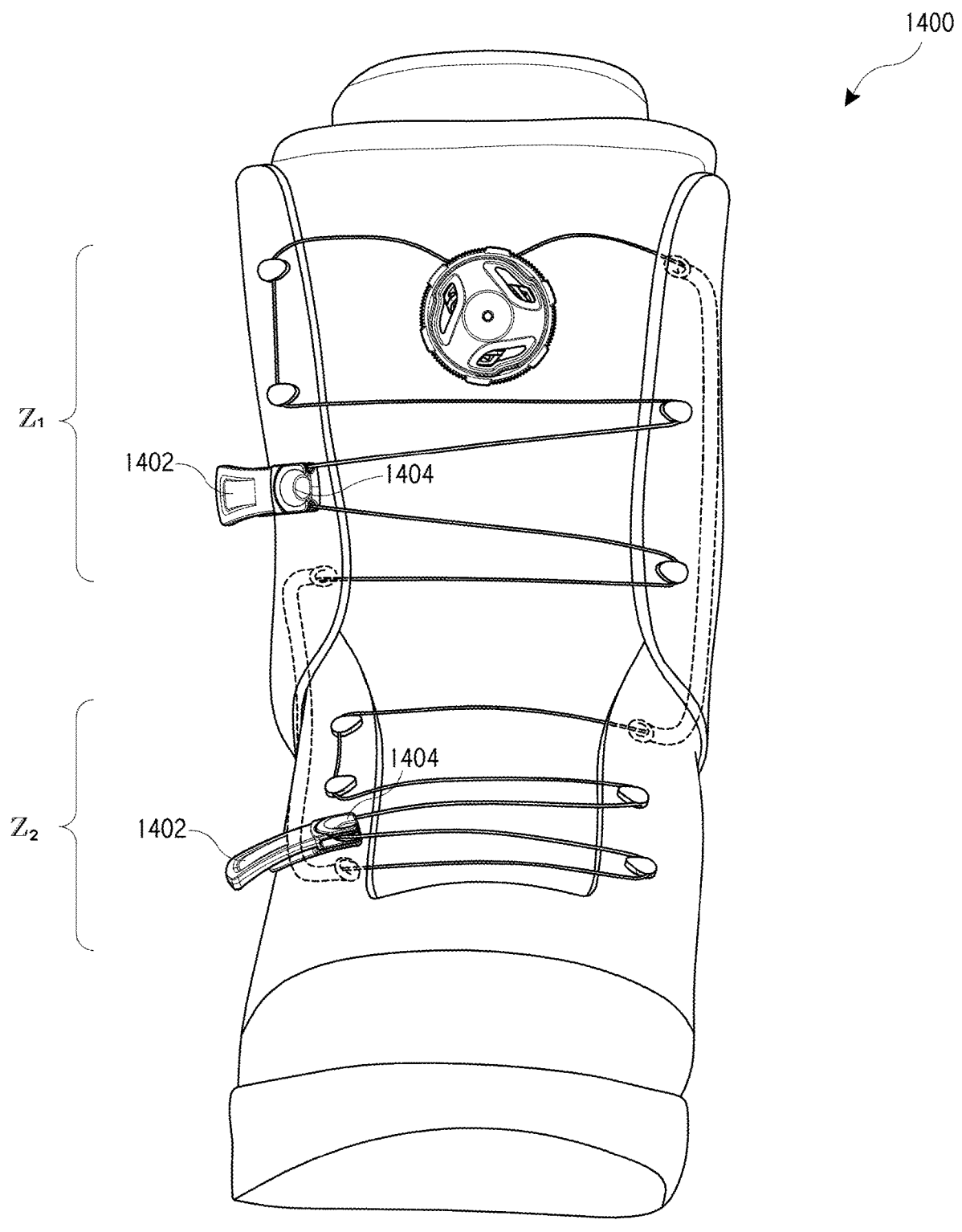

FIGS. 14A-B illustrate a lacing configuration described above applied to a boot 1400 (see FIG. 7). Specifically, as described herein above, the boot 1400 includes a tightening mechanism, an upper tightening zone $Z_1$, a lower tightening zone $Z_2$, a plurality of elongate guides that routes lace between the upper and lower zones, and a plurality of additional guides positioned within the upper and lower zones. The upper zone $Z_1$ and/or lower zone $Z_2$ of the boot 1400 further includes an additional guide 1404 that is releasably couplable with a guide component 1402 to increase or decrease tightness in the upper zone $Z_1$ and/or lower zone $Z_2$ as desired. For example, as shown in FIG. 14A, the guide component 1402 may be uncoupled from the additional guide 1404 to achieve a nominal or base tightness in the upper and/or lower zones, $Z_1$ and $Z_2$. If additional tightness is desired in the upper and/or lower zones, the guide component 1402 may be pulled laterally across the opening of the boot 1400 (or across the lace path of the boot 1400) and coupled with the corresponding additional guide 1404 as shown in FIG. 14B. Coupling of the guide component 1402 with the additional guide 1404 as shown in FIG. 14B results in additional lace crossings in the upper and/or lower zones, which increases the tightness in the corresponding zone and/or tension in the lace. Accordingly, the tightness in the upper and/or lower zones may be controlled and/or varied as desired.

Figure 16:
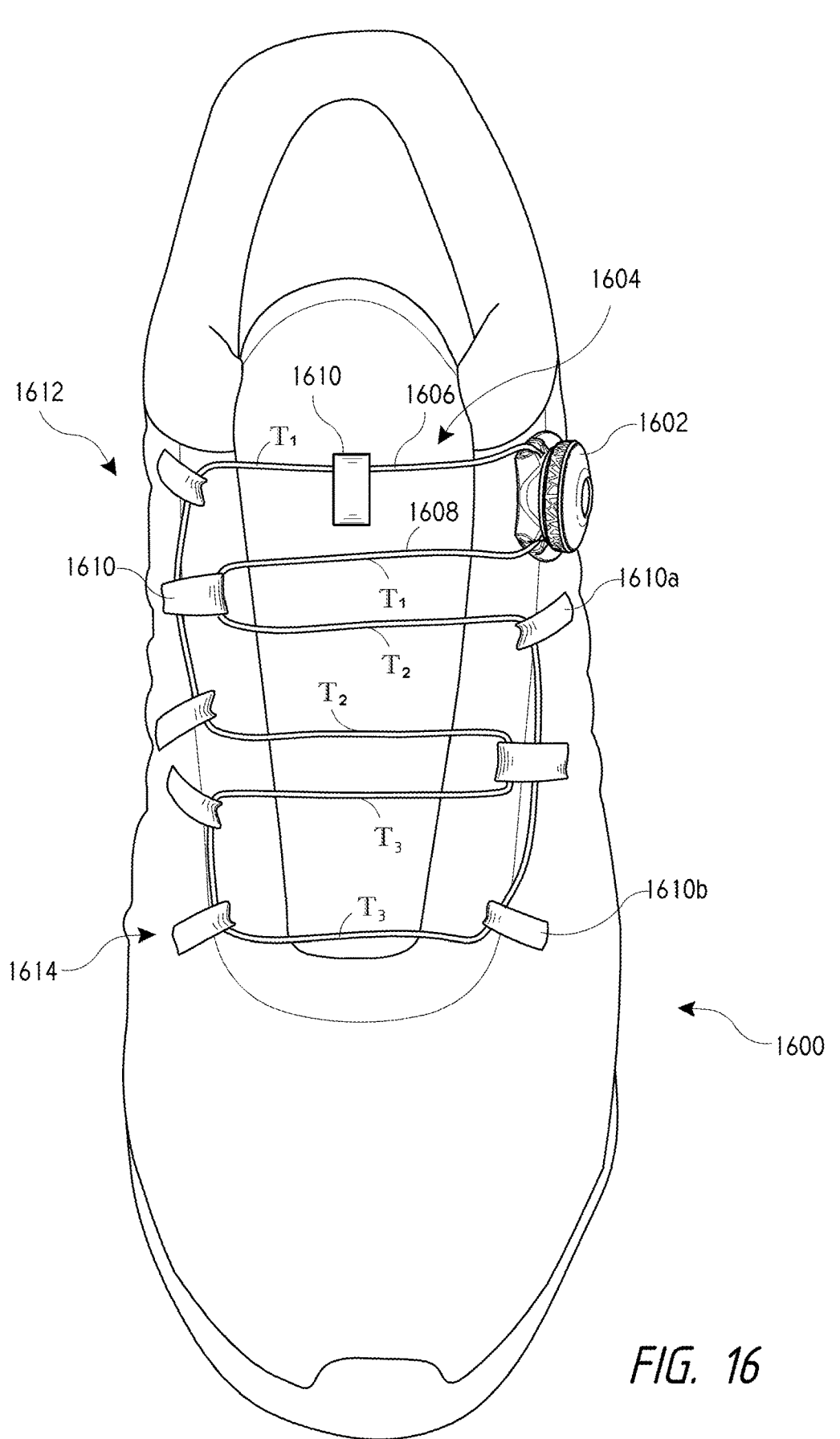
FIG. 16 illustrates another embodiment of a shoe having a lace path that may limit dynamic lace shifting and/or provides a more uniform tightening of the shoe.

Referring now to FIG. 16 illustrated is another embodiment of a shoe 1600 having a lace path that may limit dynamic lace shifting and/or provides a more uniform tightening of the shoe 1600. The shoe 1600 includes a tightening mechanism 1602 that may be grasped and rotated by a user to tighten and/or loosen a lace 1604. Some conventional systems include a single lace end that is coupled with the reel assembly's spool so that operation of the tightening mechanism tensions only a single end of the lace. The reel assembly 1602 is positioned on the side of the shoe 1600 adjacent the shoe's eyestay.

The lace 1604 is positioned so as to traverse along a lace path across the tongue portion of the shoe 1600 between a top or proximal portion or end 1612 of the lace path (i.e., near the shoe's tongue or collar) and a bottom or distal portion or end 1614 of the lace path (i.e., near the shoe's toe box). The lace 1604 is guided along the lace path via a plurality of guides 1610 that may function independently or as a pair (i.e., guides 1610a & 1610b) as shown to guide the lace 1604 along the lace path. The lace 1604 is positioned about the tongue portion of the shoe 1600 so that the lace crossings are roughly parallel and roughly orthogonal of the shoe's eyestay. This configuration results a greater degree of lace tension being used to pull the opposing eyestays of the shoe closed.

An upper or first lace portion 1606 exits the reel assembly 1602 and immediately traverses across the shoe's tongue before being routed, via a pair of guides, to a mid-portion of the shoe, which may equidistant between the proximal end 1612 and distal end 1614, or may be positioned closer to the distal end 1614. The first lace portion 1606 then traverses the shoe's tongue one or more times (illustrated traversing twice) before joining a second lace portion 1608. As illustrated, the second lace portion 1608 exits the reel assembly 1602 and immediately traverses across the shoe's tongue below the first lace portion 1606 before being routed, via a pair of guides 1610a & 1610b, to the bottom end 1614 of the lace path. The second lace portion 1608 then traverses across the shoe's tongue at the bottom end 1614 of the lace path before joining with the first lace portion 1606.

The result of the lace configuration illustrated in FIG. 16 is a cascading lace tension across the shoe's tongue. For example, since the first and second lace portions, 1606 and 1608, immediately traverse across the proximal end 1612 of the lace path, the result is a primary tensioning $T_1$ of the proximal end of the lace path and shoe 1600. The first and second lace portions, 1606 and 1608, then are routed to and traverse the mid-portion of the lace path, which result in a secondary tensioning $T_2$ of the mid-portion of the lace path and shoe 1600. The first and second lace portions, 1606 and

1608, then are routed to and traverse the bottom end 1614 of the lace path, which results in tertiary tensioning $T_3$ of the bottom end of the lace path and shoe 1600.

Given that frictional engagement of the lace 1604 and guides 1610 will result in some loss of tension in the lace 1604, the secondary tension $T_2$ is likely slightly less than the primary tension $T_1$ and the tertiary tension $T_3$ is likely slightly less than the secondary tension $T_2$. Similarly, the primary tension zone (i.e., the zone associated with tension $T_1$) will tension before the secondary tension zone (i.e., the zone associated with tension $T_2$) and the secondary tension zone will tension before the tertiary tension zone (i.e., the zone associated with tension $T_3$). The result is a cascading tensioning and tightness of the shoe 1600 along the lace path between the proximal end 1612 and the distal end 1614. Although FIG. 16 illustrates the shoe 1600 having three zones that tension in a cascading manner, it should be realized that more or fewer zones that tension the shoe 1600 in a cascading manner may be created along the lace path.

Figure 17:
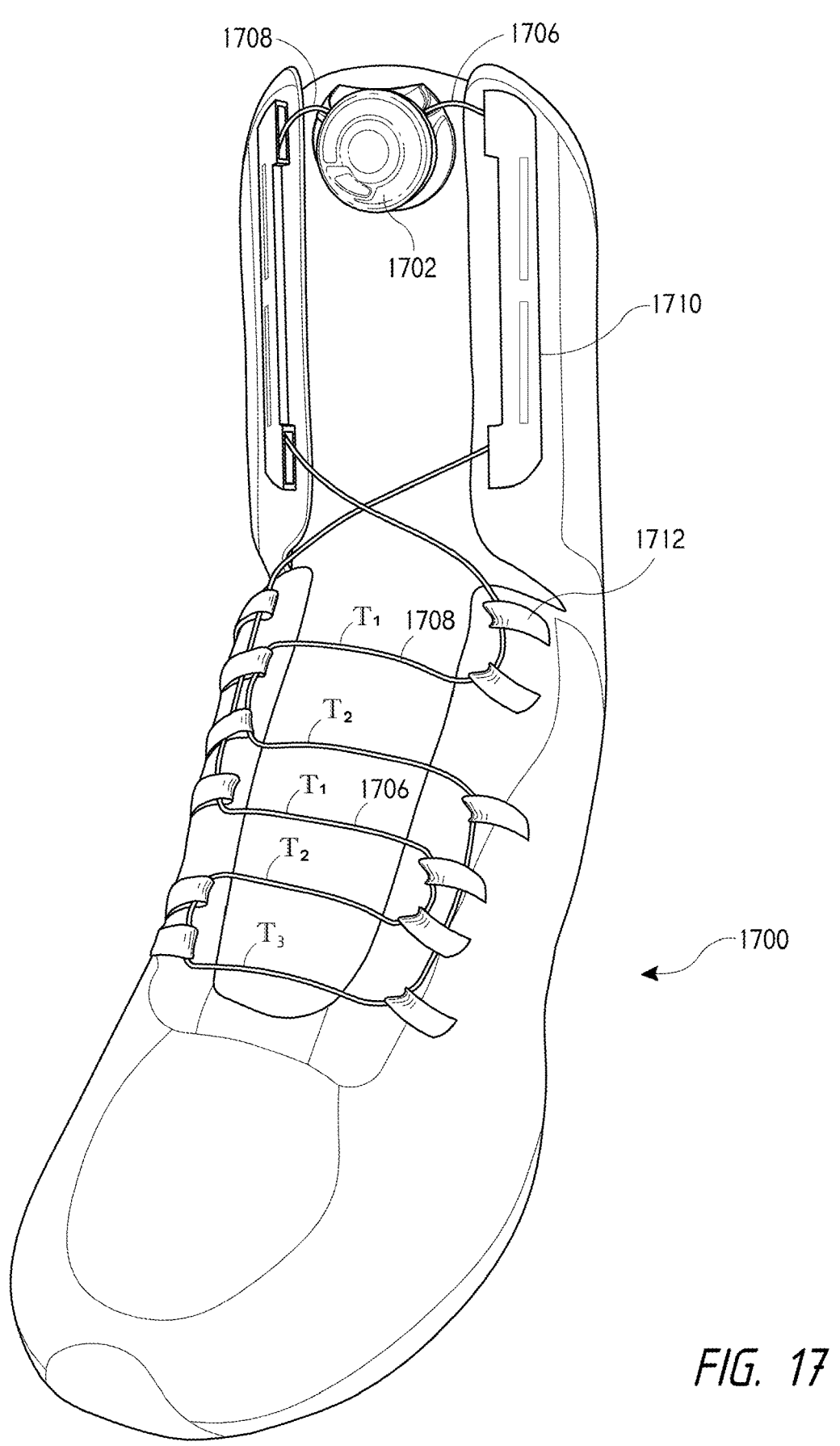
FIG. 17 illustrates an embodiment of a high-top shoe or boot.

FIG. 17 illustrates an embodiment of a high-top shoe or boot 1700. A first lace portion 1706 is routed from a tensioning mechanism 1702 to a mid-point of a lace path of the shoe 1700. A second lace portion 1708 is routed from the tensioning mechanism 1702 to an upper portion of the lace path. The first and second lace portions, 1706 and 1708, then traverse downward along the lace path from the respective positions and connect on a side of the shoe 1700. The lace portions, 1706 and 1708, are guided along the lace path via one or more webbing guides 1712 and/or component guides 1710 that may be made of a more rigid type material, such as plastic. The component guides 1710 and/or webbing guide pairs 1712 may include an elongated portion that routes the lace along a substantial portion of the shoe 1700.

The lace path of shoe 1700 results in an initial tensioning $T_1$ of the top and mid-portion of the lace path. A secondary tensioning $T_2$ occurs in a lace crossing immediately below the top and mid-portion of the lace path, and a tertiary tensioning $T_3$ occurs at the bottom portion of the lace path.

Figure 18:
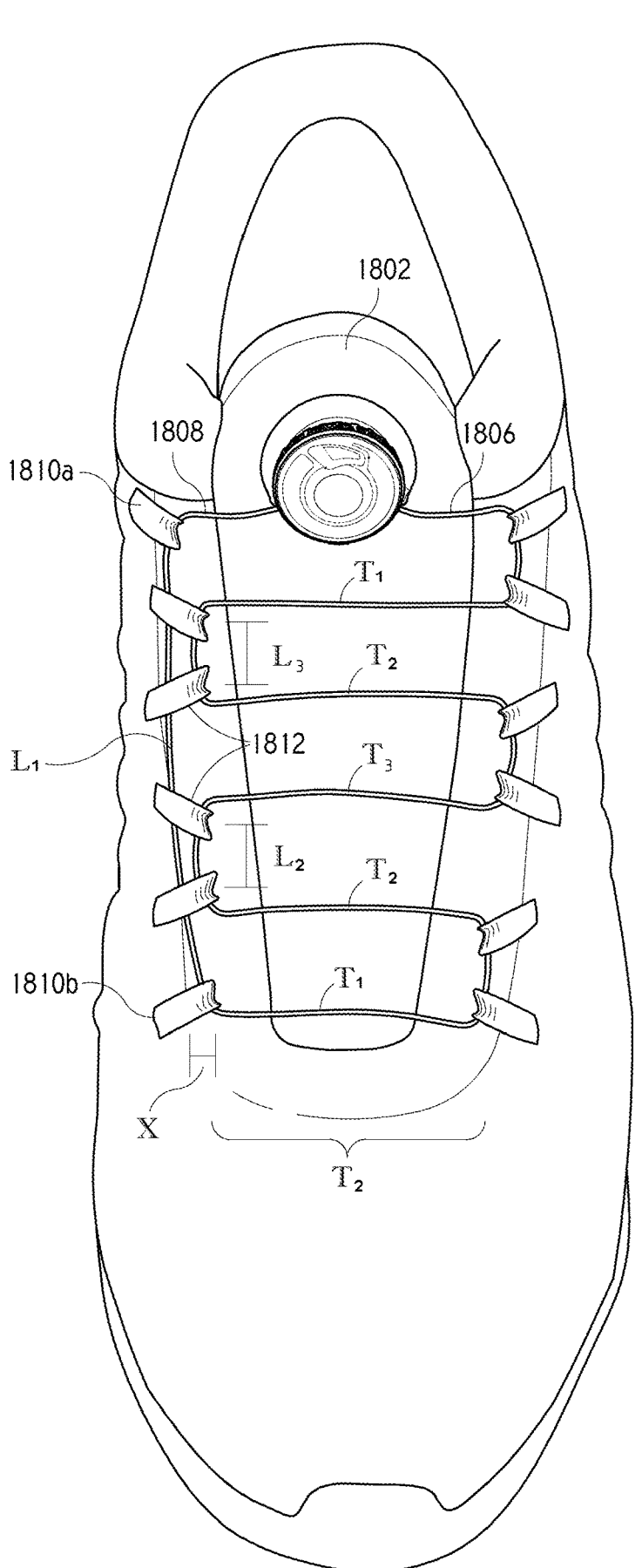
FIGS. 18-23 illustrate embodiments of lace paths of a shoe wherein a portion of the lace is routed immediately to a distal end of the lace path.

FIGS. 18-23 illustrate embodiments wherein a portion of the lace is routed immediately to a distal end of the lace path. For example, FIG. 18 illustrates a shoe wherein a first lace portion 1806 is immediately routed from the tensioning mechanism 1802 to a proximal end of the lace path. The first lace portion 1806 then traverses, via a plurality of lace guides, across an opening of the shoe (e.g., tongue portion) toward the distal end of the lace path. A second lace portion 1808 is immediately routed from the tensioning mechanism 1808 to the distal end of the lace path. The second lace portion 1808 then traverses, via the plurality of lace guides, across the opening of the shoe toward the proximal end of the lace path. The two lace portions converge in the mid-portion of the lace path to form a single unitary lace path as shown.

The effect of the lace configuration illustrated in FIG. 18 is that a primary tensioning $T_1$ occurs at the proximal and distal ends of the lace path and a secondary tensioning $T_2$ occurs immediately adjacent and inward of the proximal and distal ends. A tertiary tensioning $T_3$ occurs at the mid-point of the lace path where the first and second lace portions, 1806 and 1808, converge. The lace path may include more or fewer lace crossing as desired, which may result in quaternary, quinary, etc., tensioning along the lace path.

FIG. 18 illustrates that the second lace portion 1808 is routed to the distal end of the lace path via a pair of webbing guides, 1810a and 1810b, that together form or define an elongated guide. As described herein, the elongated guide that is formed by the webbing guides, 1810a and 1810b, is laterally offset from or outward of the inner guides 1812 that route the lace along the lace path. The elongated guide formed by the webbing guides, 1810a and 1810b, is also laterally offset or outward from a tensioning zone $T_z$ that is defined by the inner guides 1812 and that corresponds to a lateral width or portion of the shoe that is pulled together via tensioning of the lace. The elongated guide formed by the webbing guides, 1810a and 1810b, may be latterly offset from the tensioning zone $T_z$ by an amount X, which may be ⅟32 of an inch or greater, and more commonly about ¼ or ½ inch.

A length $L_1$ of the elongated guide, or more appropriately a length of the second lace portion 1808 that traverses or is routed along the elongated guide, is greater than the length of at least one inner lace guide 1812. In the illustrated embodiment, the length $L_1$ of the elongated guide is greater than a combination of multiple inner lace guides 1812—i.e., a length $L_2$ of a first inner lace guide pair and a length $L_3$ of a second inner lace guide pair. The elongated guide and inner guides are arranged so that the multiple inner lace guides 1812 are disposed within or between the opposing ends of the elongated lace guide. In some instances, the second lace portion 1808 that traverses or is routed via the elongated guide is also disposed through a portion of one or more inner guides 1812 as shown.

Figure 19:
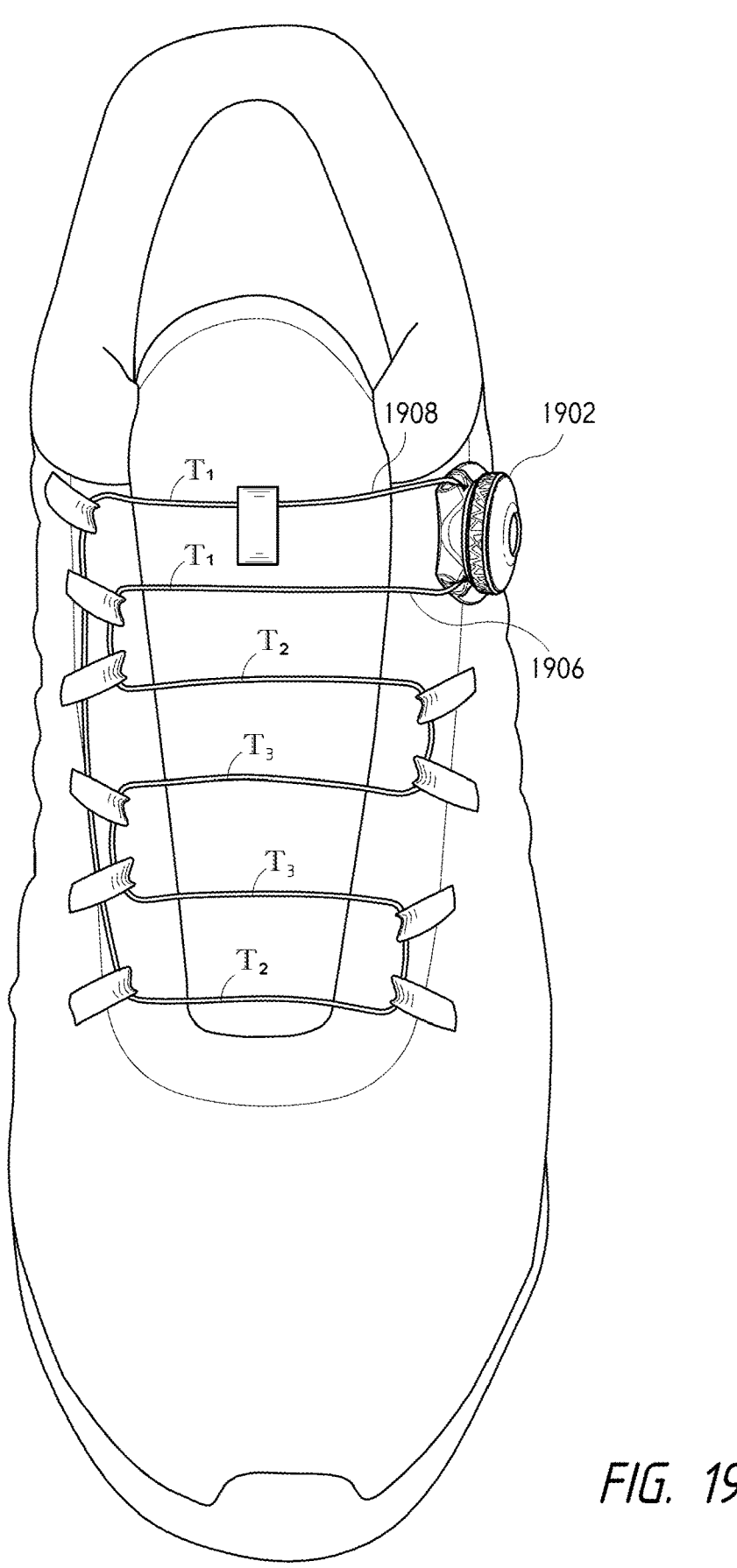

FIGS. 19-23 illustrate similar embodiments to FIG. 18 and thus, the disclosure of FIG. 18 is equally applicable to FIGS. 19-23. FIG. 19 illustrates a similar embodiment with the tensioning mechanism 1902 positioned on a side of the shoe near the eyestay or tightening edge of the shoe's tongue. A first lace portion 1908 extends from the tightening mechanism and across an opening of the shoe at the proximal end of the lace path. The first lace portion 1908 is then routed to the distal end of the lace path and is routed therefrom toward the proximal end via a plurality of guides. A second lace portion 1906 also extends from the tightening mechanism and across the shoe's opening at the proximal end of the lace path. The second lace portion 1906 is routed from the proximal end toward the distal end of the lace path via the lace guides.

The tensioning of the lace path is similar to that of FIG. 18, except that the initial crossing of the first lace portion 1908 at the proximal end of the lace path results in a primary tensioning $T_1$ of the proximal end of the lace path. The secondary and tertiary tensioning, $T_2$ and $T_3$, of the lace path is then relatively evenly mirrored longitudinally along the lace path as shown. The lace configuration of FIG. 19 may be beneficial where a tighter fit of the shoe near the shoe's collar is desired, but where it is also desired to maintain a relatively high tension of the shoe near the toe-box and/or a relatively even tensioning of the shoe along the lace path.

Figure 20:
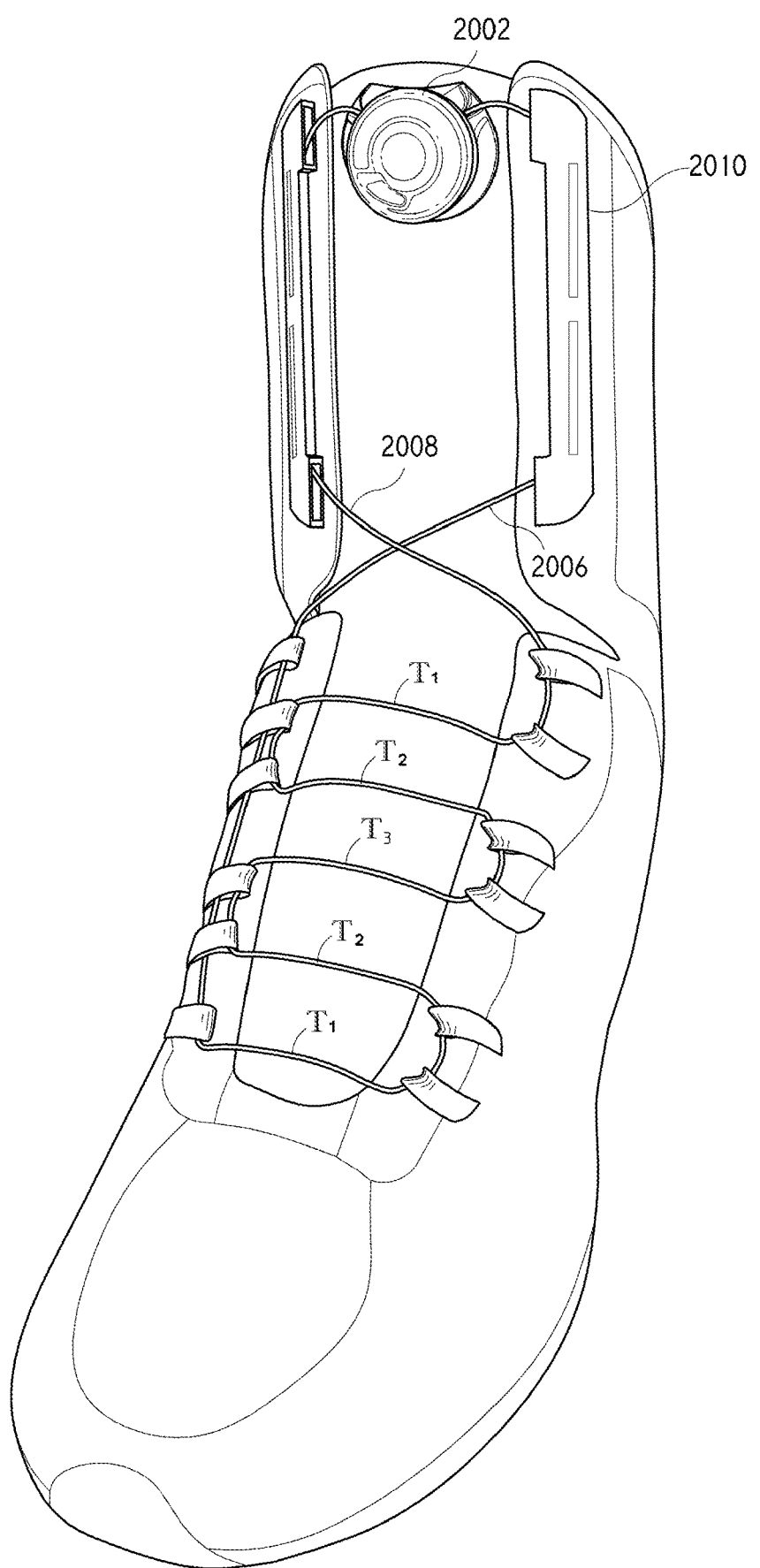

FIG. 20 illustrates an embodiment similar to FIG. 18, except that the lace is routed about a high-top shoe, boot, or other elongated footwear. A first lace portion 2006 is routed from the tightening mechanism 2002 to the distal end of the lace path and routed therefrom toward the proximal end of the lace path via a plurality of lace guides. A second lace portion 2008 is routed from the tightening mechanism to the proximal end of the lace path and routed therefrom toward the distal end of the lace path. The resulting primary, secondary, and tertiary tensioning of the lace path (i.e., $T_1$, $T_2$, $T_3$) is mirrored longitudinally along the lace path as described in FIG. 18.

The lace portions, 2006 & 2008, are routed along the upper portion of the shoe and to the lace path via elongated guides 2010 that are configured so that the lace traverse along the shoe roughly parallel to the eyestay or tightening edge of the shoe's opening (i.e., the shoe's tongue). Because the lace traverses along the shoe in this manner, the lace tension does not effect closure or tightening of the shoe and frictional loss is minimized. To prevent longitudinal buckling or collapse of the upper portion of the shoe, the elongated guides 2010 may be made of relatively rigid or stiff materials.

The shoe will experience some closure or tightening where the first lace portion 2006 and second lace portion 2008 cross one another. However, tightening at this location will be less than that experienced within the lower lace path since the lace traverses the opening diagonally rather than orthogonal to the opening.

Figure 21A:
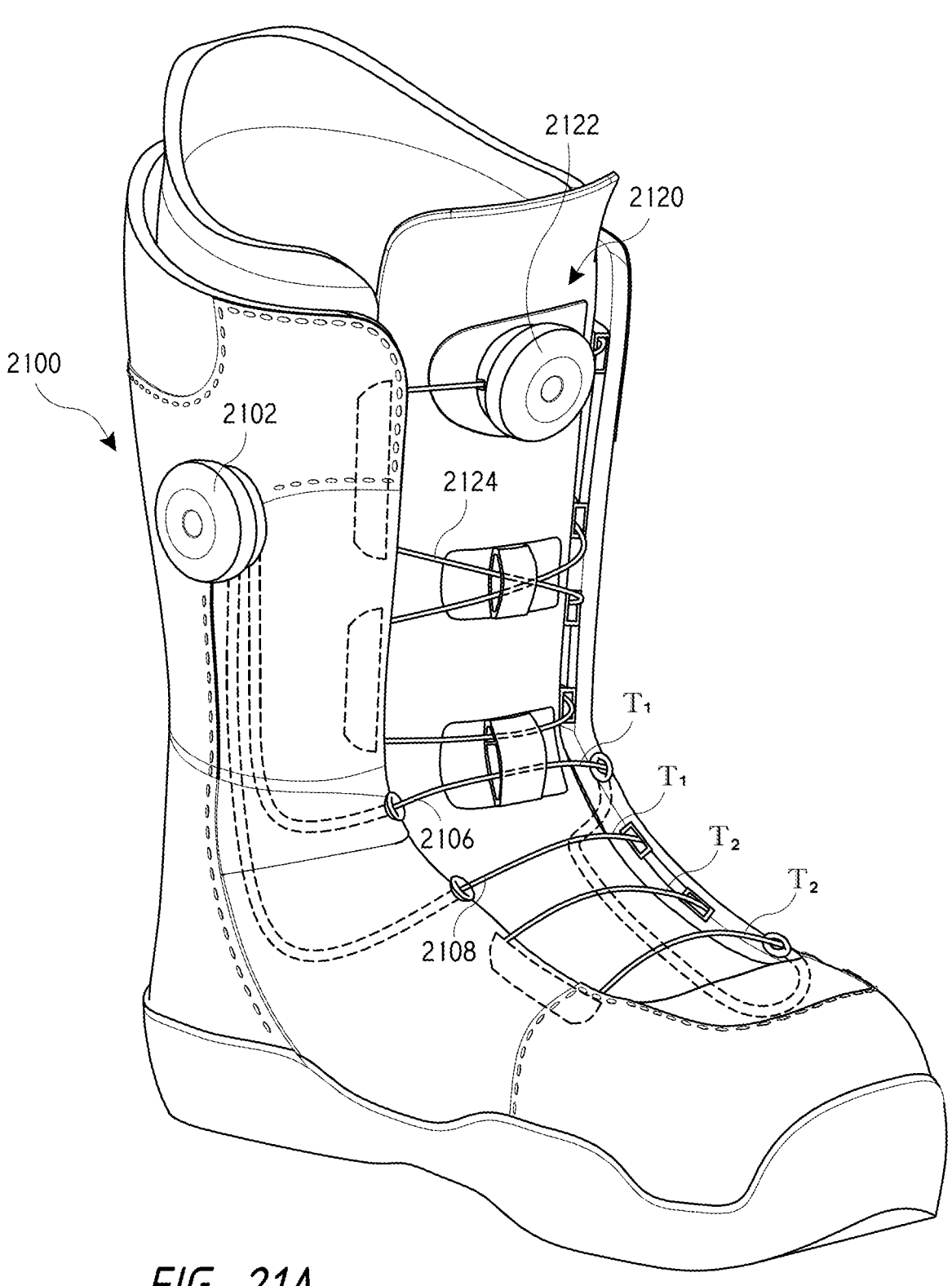
Figure 21B:
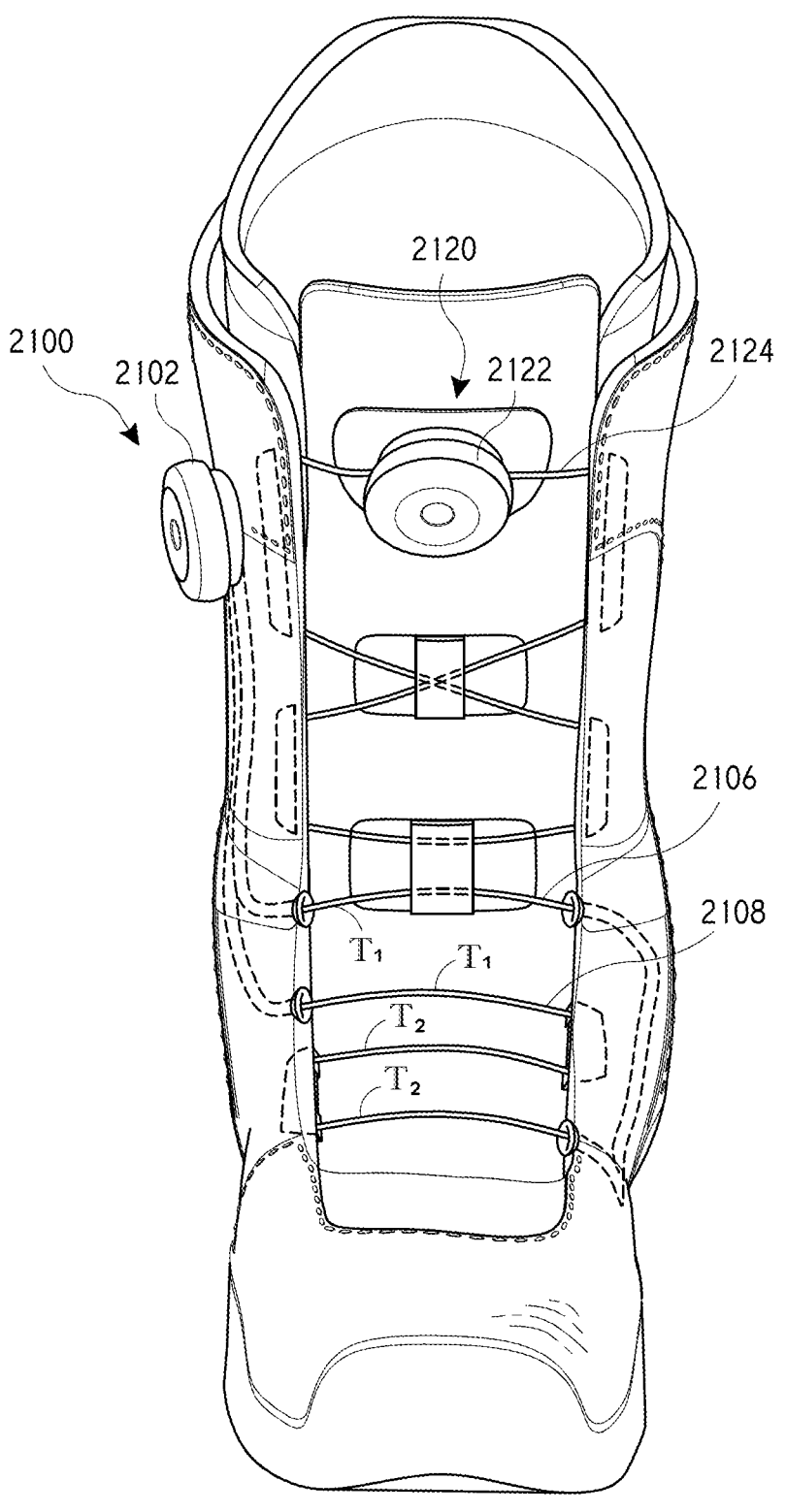

FIGS. 21A-B illustrate a boot or high-top shoe that includes a pair of tensioning systems. Specifically, the boot includes a first tensioning system 2120 that is positioned on an upper portion of the boot and that is arranged and coupled with the boot so that operation of a tensioning mechanism 2122 effects closure and/or tightening of the upper portion of the boot. The tensioning mechanism 2122 is operationally coupled with a tension member 2124 that is routed about the upper portion of the boot via a plurality of guides. The tension member 2124 may be routed about the upper portion to form a symmetrical lace path along the upper portion of the boot as shown. Operation of the tensioning mechanism 2122 tensions the tension member 2124, which closes and tightens the upper portion of the boot.

The boot also includes a second tensioning system 2100 that is operable to close and tighten a lower portion of the boot. Specifically, the second tensioning system 2100 includes a tensioning mechanism 2102 that is operationally coupled with a first lace portion 2106 and a second lace portion 2108. The first lace portion 2106 is routed from the tensioning mechanism 2102 via tubing to a proximal end of a lace path about the lower portion of the boot. The first lace portion 2106 extends across an opening of the lower portion of the boot and is routed therefrom, via tubing, to a distal end of the lace path. The second lace portion 2108 is routed from the tensioning mechanism 2102 via tubing to a mid-portion of the lace path. The second lace portion 2108 is routed across the mid-portion of the lace path twice, via tubing or lace guides, before connecting with the first lace portion 2106. The effect of the lace configuration of FIGS. 21A-B is that a primary tensioning $T_1$ occurs in the proximal end of the lower portion's lace path and a secondary tensioning $T_2$ occurs in the distal end of the lower portion's lace path.

In some instances, the second lace portion 2108 may be routed from the tensioning mechanism 2102 to the distal end of the lace path so that the primary tensioning $T_1$ occurs at both the proximal and distal ends of the lace path. In some embodiments the tensioning systems, 2100 and 2120, may be reversed in relation to the boot so that the upper portion of the boot includes a non-symmetrical lace path as illustrated and the lower portion of the boot includes a symmetrical lace path. In other embodiments, both the upper and lower portions of the boot may include non-symmetrical lace paths as illustrated. In addition, the tensioning mechanism 2102 may be mounted on the boot remotely from the lower lace path as illustrated, or may be mounted on the boot so as to be adjacent the lower lace path as desired.

Figure 22A:
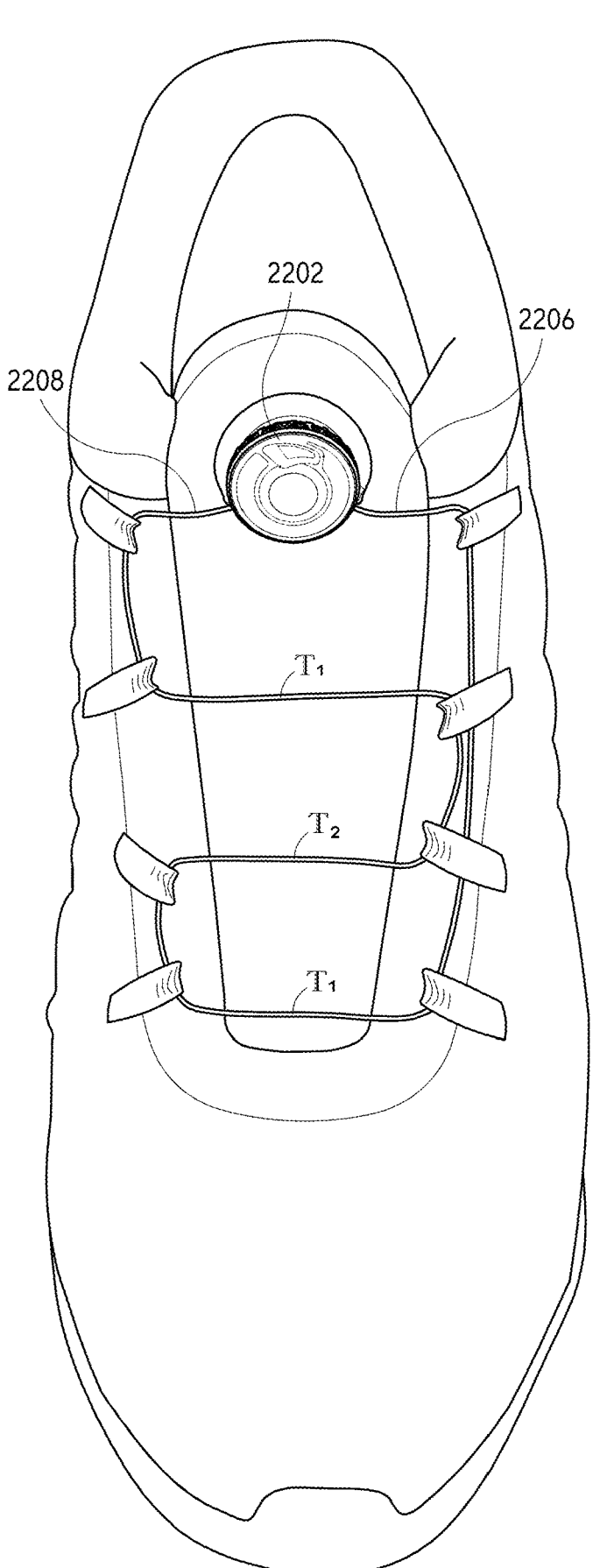

FIG. 22A illustrates an embodiment that is similar to FIG. 18 except that the shoe includes fewer lace crossings across the shoe's opening and the elongated lace guide is positioned on an opposite side of the shoe's opening. Specifically, the first lace portion 2206 is immediately routed from the tensioning mechanism to the distal end of the lace path and traverses across the distal end a single time before joining the second lace portion 2208, which is routed from the tensioning mechanism 2202 to the proximal end of the lace path. The lace configuration of FIG. 22A results in a primary tensioning $T_1$ of the proximal and distal end of the lace path and a secondary tensioning $T_2$ of the mid-portion of the lace path.

Figure 22B:
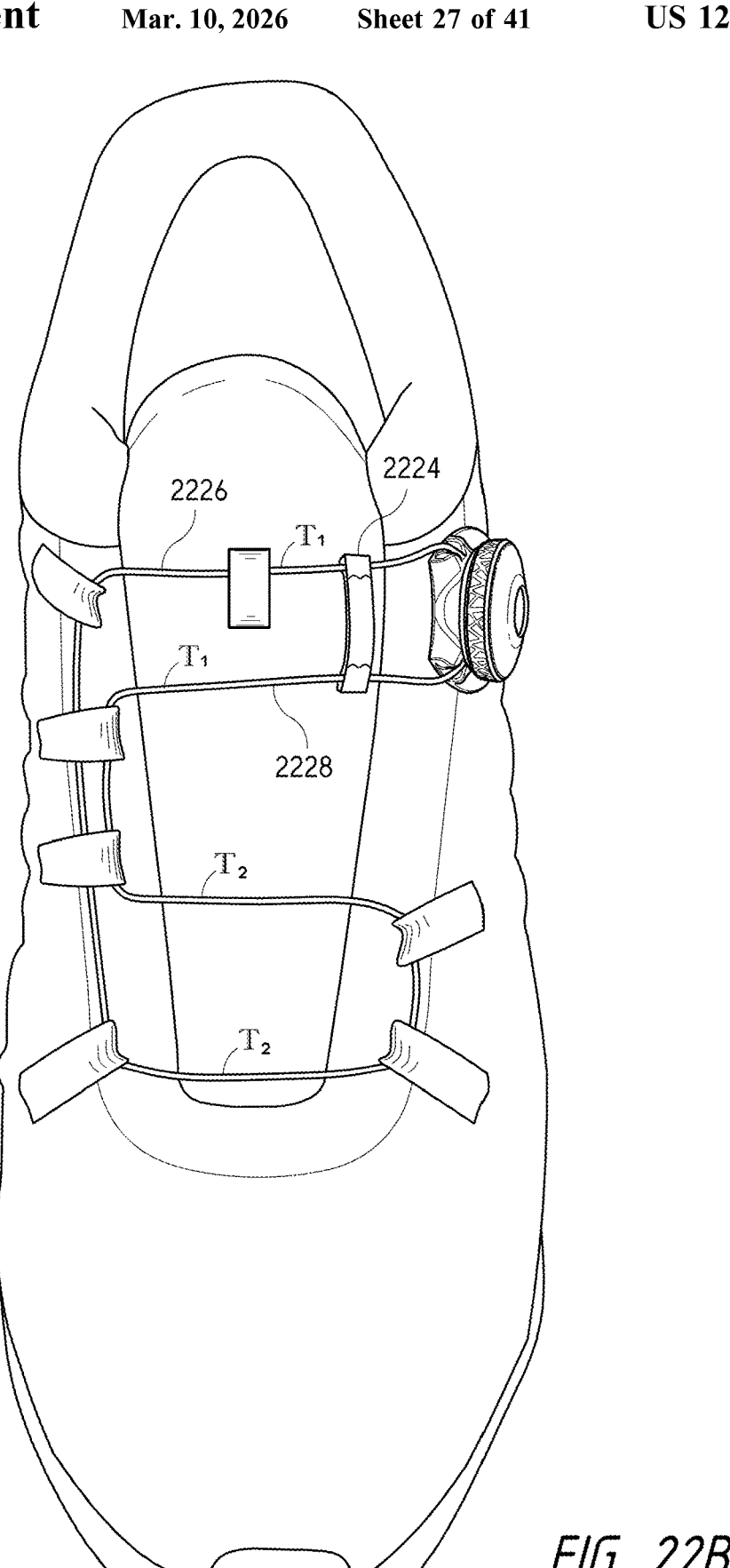

FIG. 22B illustrates an embodiment that is similar to FIG. 19 except that the shoe includes fewer lace crossings across the shoe's opening. Specifically, the first lace portion 2226 is routed initially across the proximal end of the lace path and then immediately to the distal end while the second lace portion 2228 is routed across the shoe's opening between the proximal and distal ends. The result is a primary tensioning $T_1$ of the proximal portion of the lace path and a secondary tensioning $T_2$ of the distal portion of the lace path. FIG. 22B also illustrates the shoe including a component 2224 that is attached to the first lace portion 2226 and second lace portion 2228 near the tensioning mechanism and that may be used to eliminate or minimize issue due to non-uniform lace ejection from the tensioning mechanism as described herein.

Figure 23:
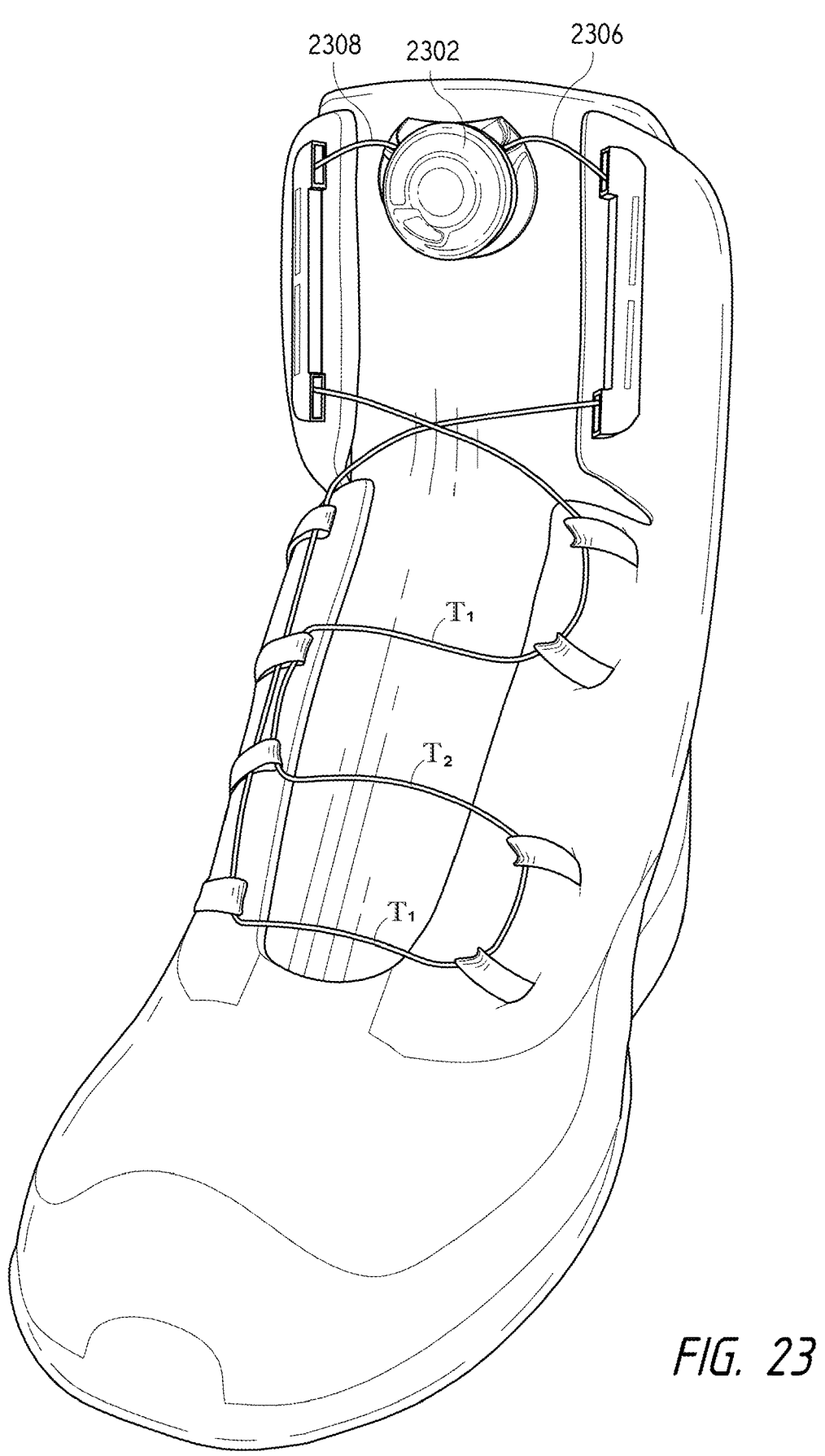

FIG. 23 illustrates a boot configuration with fewer lace crossings. A first lace portion 2306 is routed from the tensioning mechanism 2302 to the distal end of the lace path and a second lace portion 2308 is routed from the tensioning mechanism 2302 to the proximal end of the lace path. The result is a primary tensioning $T_1$ of the proximal end distal ends of the lace path and a secondary tensioning $T_2$ of the mid-portion of the lace path.

Figure 24:
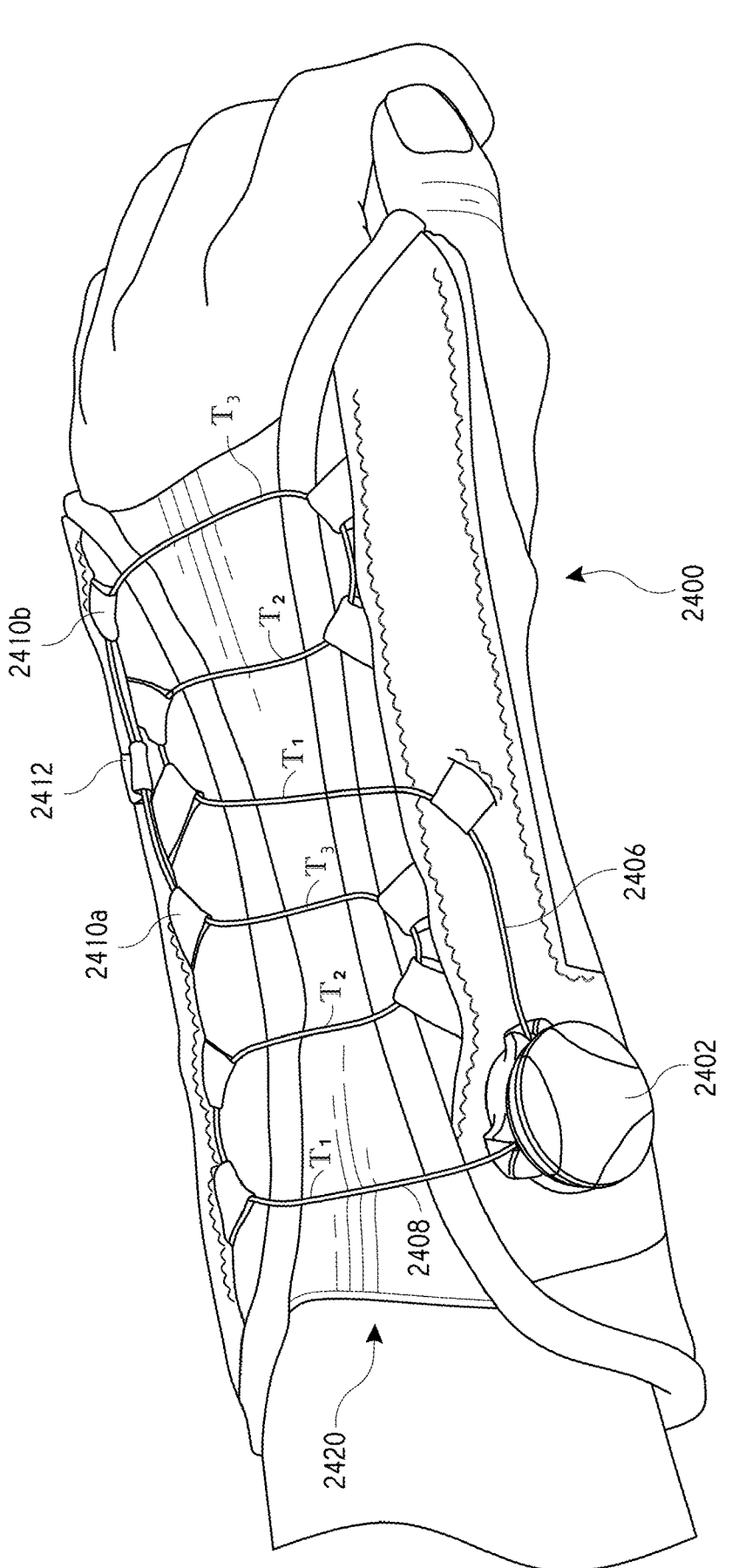
FIGS. 24-26B illustrate embodiments of medical devices that include non-symmetrical lace paths.

FIGS. 24-26B illustrate various medical devices that include non-symmetrical lace paths similar to those described herein. FIG. 24 illustrates a brace 2400 that is configured to fit and tighten about a user's wrist. The brace 2400 has an opening 2420 that may be opened or closed to allow the user to don and doff the brace 2400. A lace is positioned and routed along a lace path about the opening 2420 via guide members, which may include solitary guides 2412, or pairs of guide members, 2410a & 2410b, or a combination thereof as illustrated. The guide members may be made of flexible or rigid materials, such as webbing, straps, plastic materials, and the like.

A tensioning mechanism 2402 is attached to the brace 2400 and operationally coupled with a first portion of the lace 2406 and a second portion of the lace 2408. The first lace portion 2406 is routed longitudinally along the brace 2400 from the tensioning mechanism 2402 to a mid-point or portion of the lace path. The first lace portion 2406 is routed from the mid-point toward a distal end of the lace path. The second lace portion 2408 is routed from the tensioning mechanism 2402 laterally across the opening 2420 at the proximal end of the lace path. The second lace portion 2408 is routed therefrom toward the mid-point of the lace path. The first and second lace portions, 2406 and 2408, intersect or converge between the mid-point and distal end of the lace path where the lace is routed via a lace guide having an elongated lace path as described herein.

The lace configuration of FIG. 24 results in a primary tensioning $T_1$ of the proximal end and mid-portion of the lace path. A secondary tensioning $T_2$ is induced in a lace crossing distally of the proximal end and the mid-portion, and a tertiary tensioning $T_3$ is induced in the distal end and adjacent the mid-portion of the lace path as illustrated. It should be recognized that the lace path of the brace 2400 may be arranged so that the first lace portion 2406 is routed immediately to the distal end as described in various embodiments herein, in which the primary tensioning $T_1$ would be induced in the proximal and distal ends and the secondary and tertiary tensioning being induced inward of the proximal and distal ends as described and illustrated herein.

Figure 25:
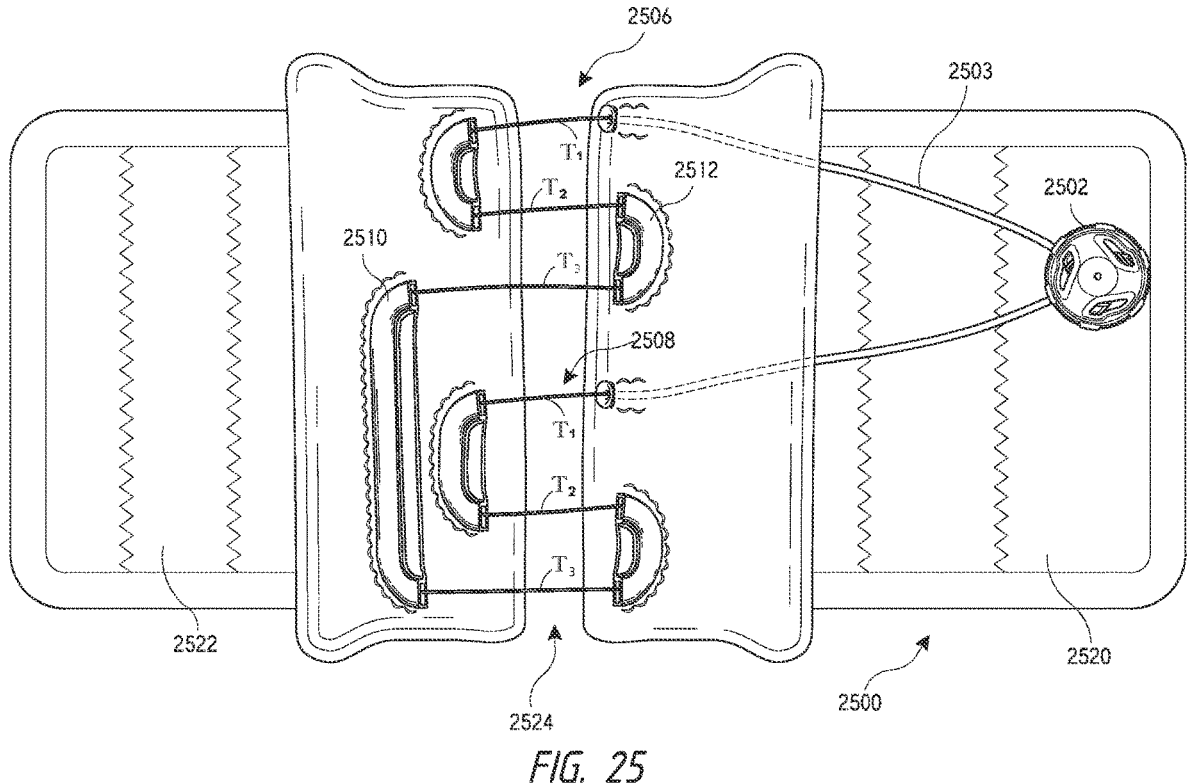

FIG. 25 illustrates a back brace 2500 that may be fit about a user's waist and tensioned to support and/or provide a therapeutic effect. The back brace 2500 includes opposing ends, 2520 and 2522, that may be positioned around the user's waist and coupled together. Coupling the opposing ends, 2520 and 2522, together provides a gross closure of the back brace 2500 about the user's waist. The back brace 2500 also includes an opening or closure zone 2524 having opposing sides that may be pulled together or apart to adjust the tightness of the back brace 2500 about the user's waist. A lace is routed along a path about the opening 2524 of the back brace 2500. A tensioning mechanism 2502 is attached to the back brace 2500 and operationally coupled with a first portion 2506 of the lace and a second portion 2508 of the lace. Operation of the tensioning mechanism 2502 tensions or loosens the first and second portions of the lace, 2506 & 2508, to effect tightening or loosening of the back brace 2500 about the user's waist.

As illustrated, the first lace portion 2506 is routed via tubing 2503 from the tensioning mechanism 2502 to a proximal end of the lace path. The first lace portion 2506 is routed from the proximal end toward a mid-portion of the lace path via one or more guide 2512. The second lace portion 2508 is routed from the tensioning mechanism 2508 to the mid-portion of the lace path and then to the distal end of the lace path via one or more guides 2512. The first lace portion 2506 and second lace portion 2508 intersect at or within an elongated guide 2510 that is positioned on an opposite side of the opening from the tensioning mechanism 2502.

As described herein, the elongated guide 2510 has a length that is longer than one or more of the guides 2512. The elongated guide 2510 is also positioned laterally outward from the one or more guides 2512. The elongated guide 2510 and the one or more guides 2512 are arranged so that opposing ends of the one or more guides 2512 are disposed between the opposing ends of the elongated guide 2510 as illustrated.

The lace configuration of back brace 2500 results in a primary tensioning $T_1$ of the proximal end and mid-portion of the back brace 2500. A secondary tensioning $T_2$ is induced in a lace crossing immediately distal to the proximal end and mid-portion and a tertiary tensioning $T_3$ is induced proximally of the mid-portion and at the distal end of the back brace 2500. Any of the other lace path configurations described and illustrated herein may be employed on back brace 2500 to achieve a different and desired tensioning.

Figure 26A:
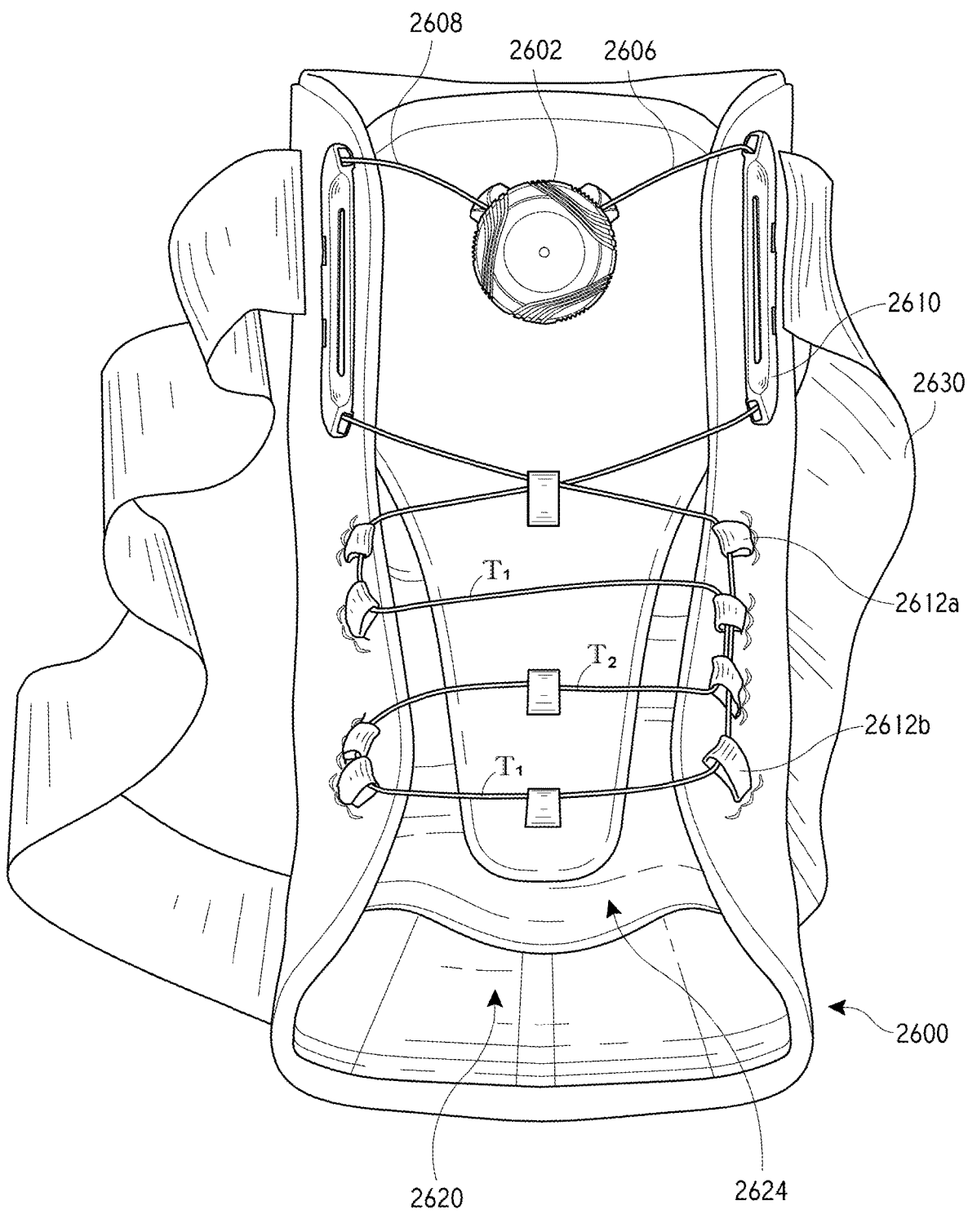
Figure 26B:
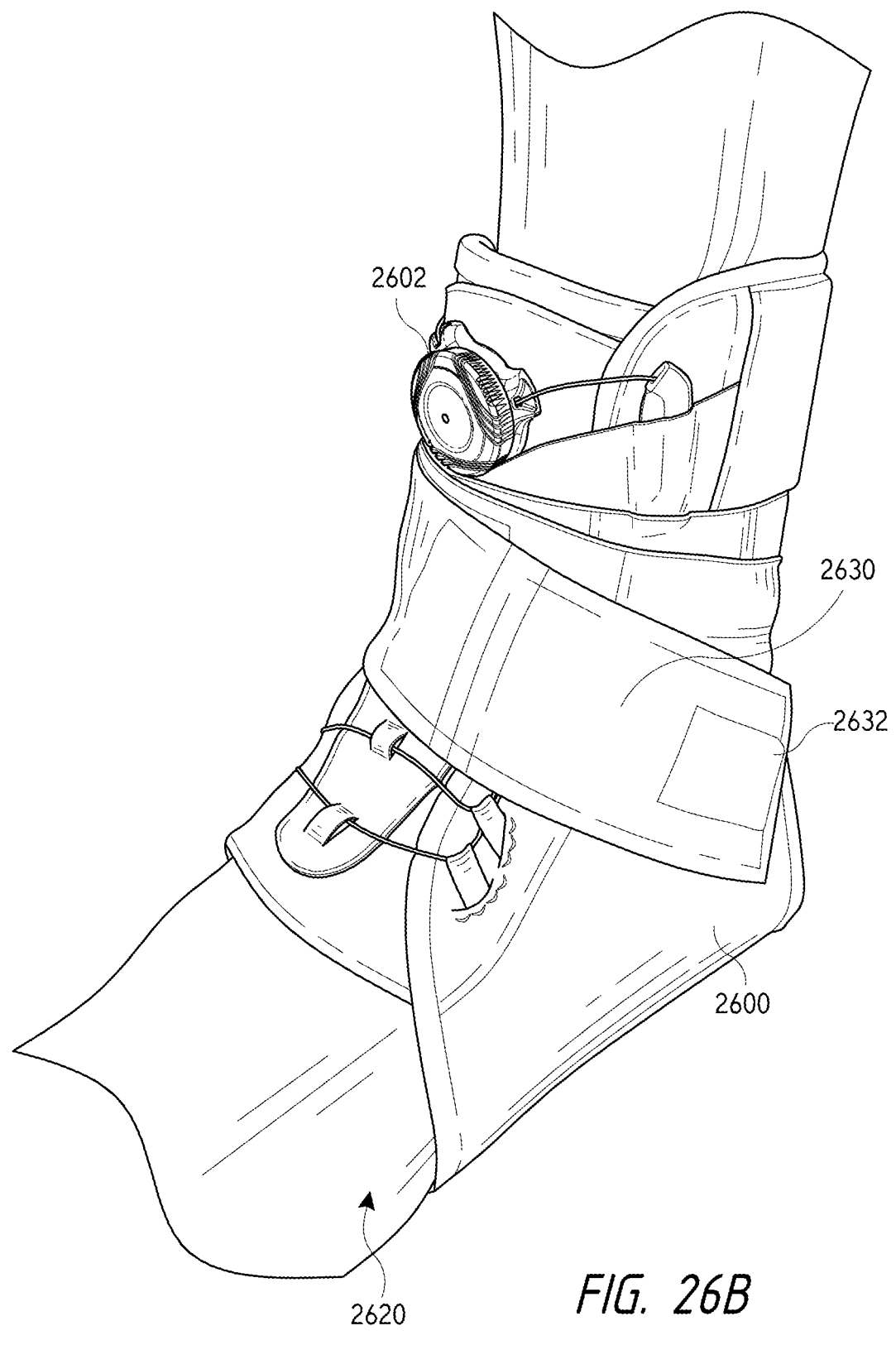

FIGS. 26A-B illustrate an ankle brace 2600 that may be fit about a user's ankle and tensioned to support and/or provide a therapeutic benefit. The ankle brace 2600 includes an inner channel or space 2620 within which a user's can insert their foot. The ankle brace 2600 also includes an opening or closure zone 2624 having opposing sides that may be moved together or apart to tighten or loosen the ankle brace 2600 about a user's foot. The ankle brace 2600 further includes straps 2630 that may be wrapped atop the brace to initially close and tighten the ankle brace 2600 about the user's foot. The straps 2630 may include a coupling member 2632 that may be used to hold and/or maintain the straps 2630 in a closed configuration.

A lace is routed along a path between opposing sides of the opening or closure zone 2624. A tensioning mechanism 2602 is attached to the ankle brace 2600 and operationally coupled with a first portion 2606 of the lace and a second portion 2608 of the lace as described herein. The first lace portion 2606 is routed from the tensioning mechanism 2602 to a proximal end of the lace path. The second lace portion 2608 is routed from the tensioning mechanism 2602 to a distal end of the lace path. The first and second lace portions, 2606 and 2608, intersect or conjoin at a mid-portion of the lace path. The lace configuration of the ankle brace 2600 results in a primary tensioning $T_1$ of the proximal and distal ends of the lace path and a secondary tensioning $T_2$ of the mid-portion of the lace path as illustrated. The tensioning mechanism 2602 may be operated after the ankle brace 2600 is fit about the ankle to adjust a fit and/or tension of the ankle brace 2600 about the user's ankle and foot.

Figure 27:
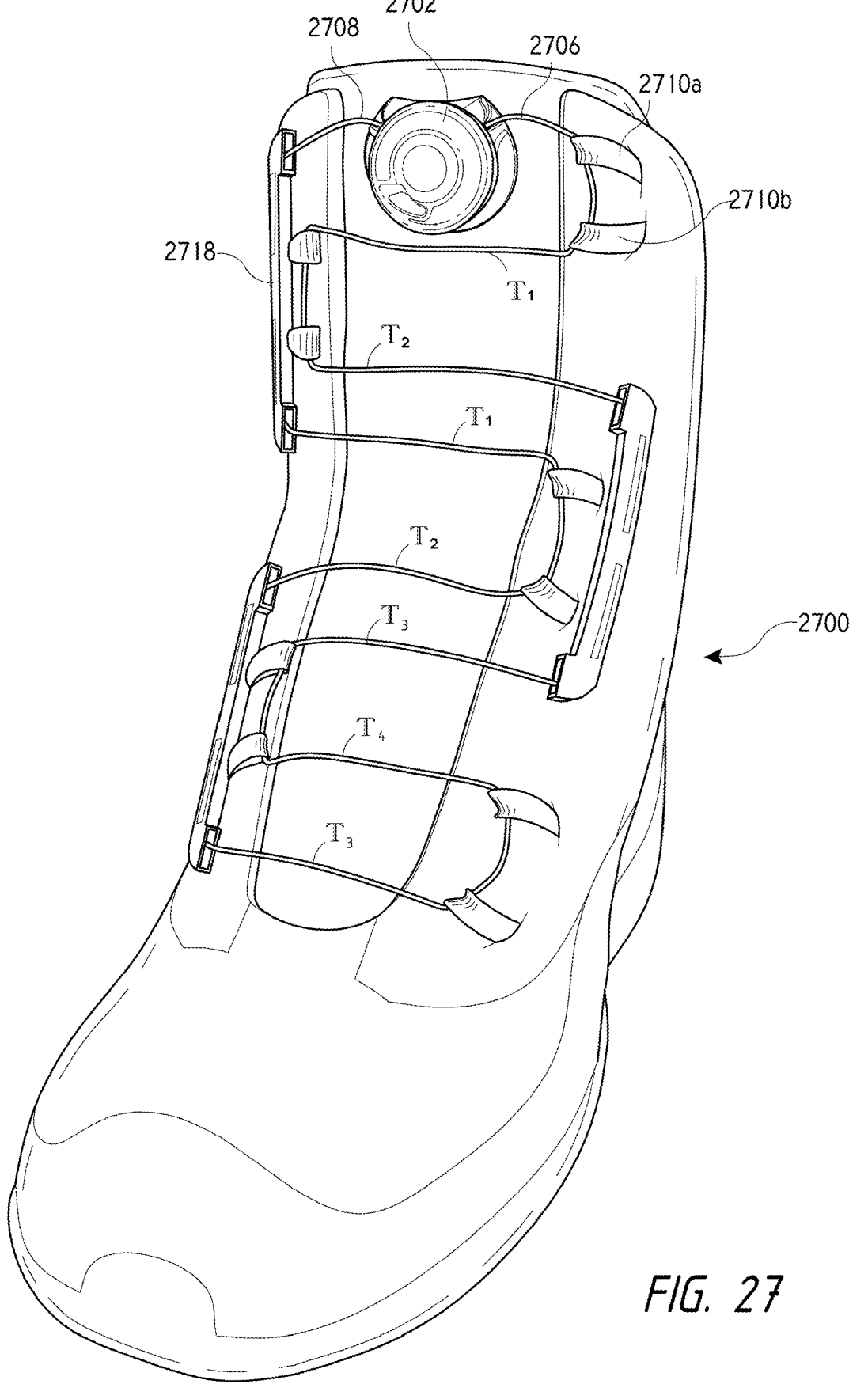
FIGS. 27-30 illustrate embodiments of alternative lace path configurations for a shoe or boot.

FIGS. 27-30 illustrate other embodiments of alternative lace path configurations. FIG. 27 illustrate a boot or high-top shoe 2700 that includes a tensioning mechanism 2702 and lace as previously described. A difference from the previously described embodiments is that both a first portion of the lace 2706 and a second portion of the lace 2708 are routed parallel to an opening or closure zone of the boot 2700 via an elongate guide. Specifically, the first lace portion 2706 is routed from the from the tensioning mechanism 2702 to a proximal end of the lace path where the first lace portion 2706 traverses twice across the opening. The first lace portion 2706 is then routed immediately to a mid-portion of the lace path via an elongate guide 2712 where the first lace portion 2706 traverses the opening again. The second lace portion 2708 is routed from the tensioning mechanism 2702 through an elongate guide to proximate the mid-portion where the second lace portion 2708 traverses twice across the opening. The second lace portion 2708 is then routed to the distal end of the lace path before traversing the opening again. The first and second lace portions, 2706 and 2708, meet near the distal end of the lace path.

As illustrated, the lace path of FIG. 27 results in the boot 2700 having elongated guides on opposite sides of the opening or closure zone. The resulting tension is a primary tension $T_1$ of both the first and second lace portions, 2706 and 2708, near the proximal end of the lace path, a secondary tension $T_2$ of both laces near the top end and mid-portion of the lace path, and a tertiary tension $T_3$ of the mid-portion and distal end of the lace path. A quaternary tension $T_4$ also occurs near the distal end of the lace path where the first and second lace portions meet.

Figure 28:
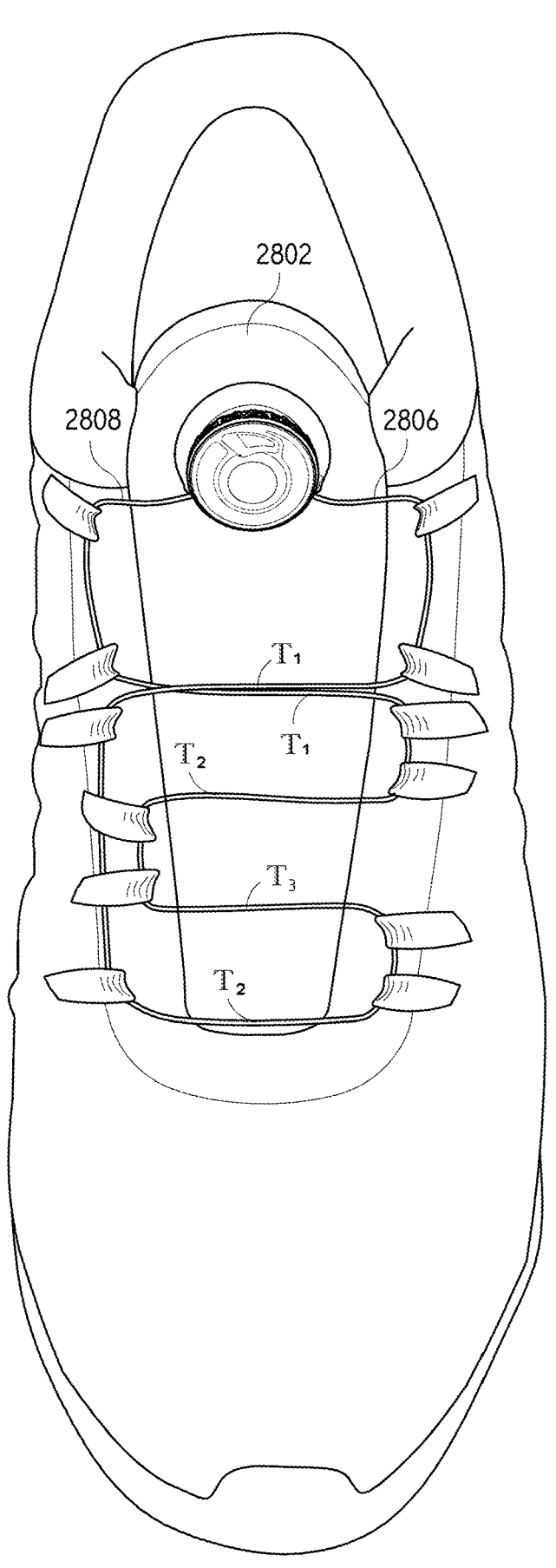
Figure 29:
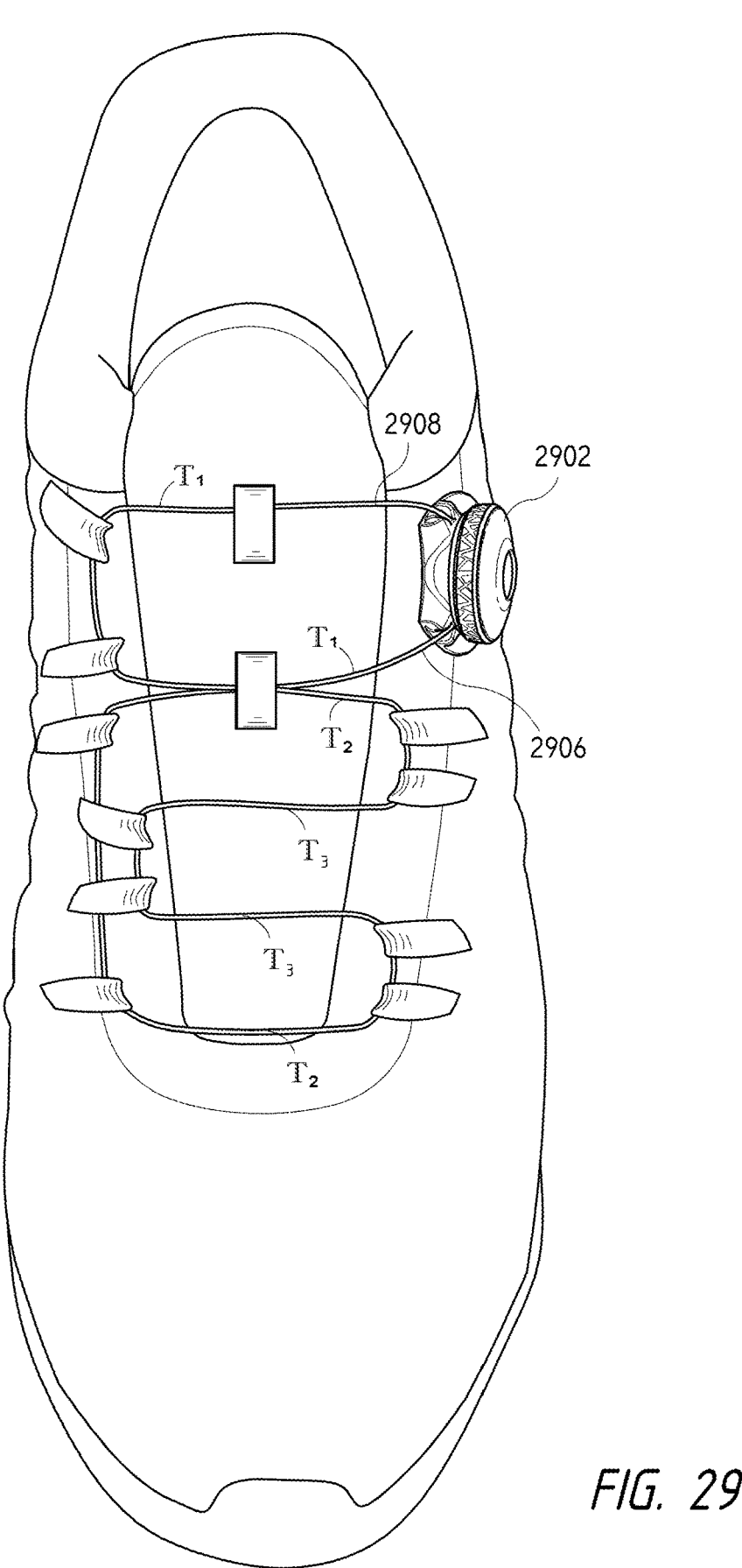

FIG. 28 illustrates a first lace portion 2806 that is routed from the tensioning mechanism 2802 and across the opening of the shoe at the proximal end of the lace path. The first lace portion 2806 is then routed to the distal end of the lace path and across the opening. A second lace portion 2808 is routed from the tensioning mechanism to the proximal end of the lace path where the second lace portion traverses the opening several times as it is routed toward the distal end of the lace path. The lace configuration results in a primary tensioning $T_1$ of the proximal end of the lace path and a relatively even tensioning of the lace path therefrom longitudinally along lace path as illustrated. FIG. 29 illustrates a similar lace configuration as FIG. 28 of the first and second lace portions, 2906 and 2908, except that the tensioning mechanism 2902 is positioned on a side of the shoe.

Figure 30:
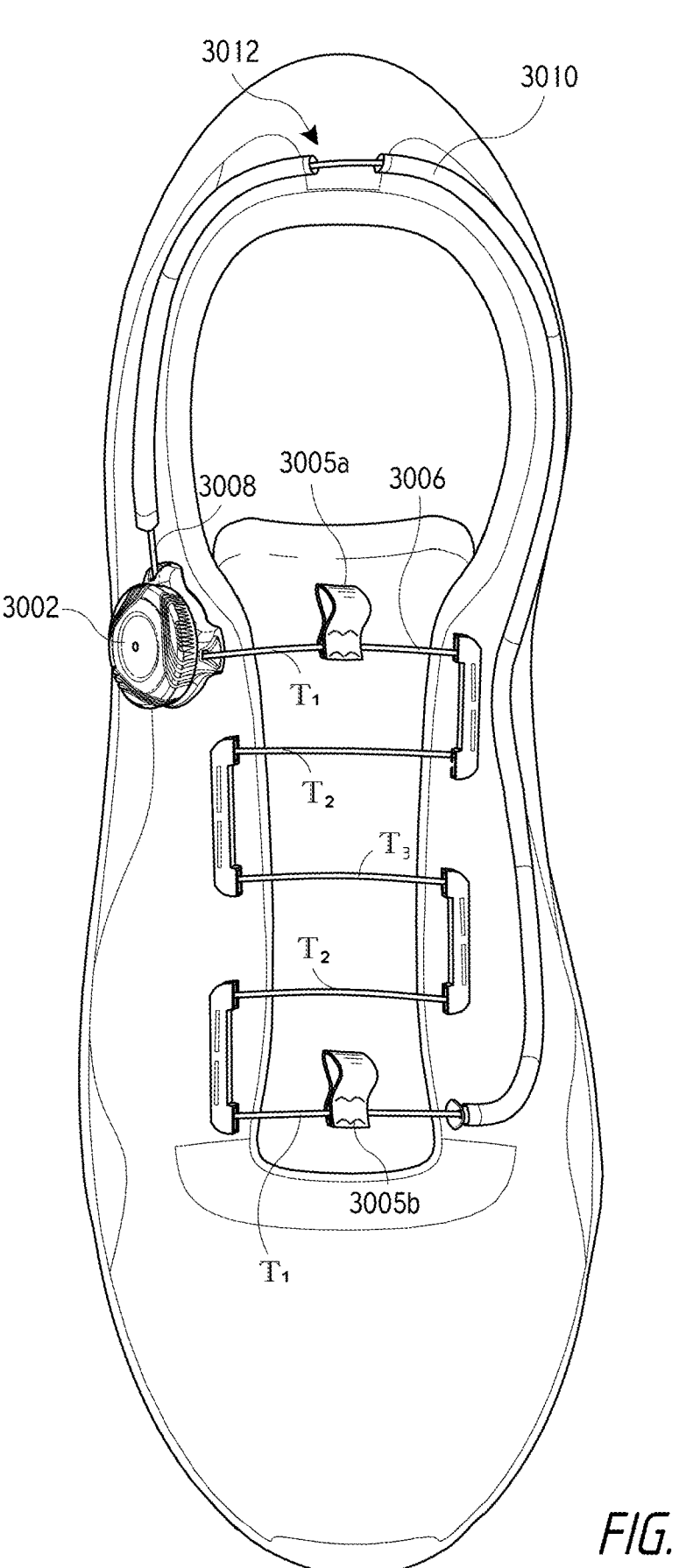

FIG. 30 illustrates an embodiment in which the tensioning mechanism 3002 is positioned on a side of the shoe with the first lace portion 3006 being routed to the proximal end of the lace path and traversing distally along the lace path toward the lace path's distal end. The second lace portion 3008 is routed around the shoe's heel, or collar, via tubing 3010. The second lace portion 3008 is routed to the distal end of the lace path and traverse proximally therefrom toward the lace path's proximal end. The result of the lace configuration of FIG. 30 is a primary tensioning $T_1$ of the proximal and distal end of the lace path, a secondary tensioning $T_2$ immediately inward of the proximal and distal ends, and a tertiary tensioning $T_3$ of the mid-portion of the lace path.

In some embodiments, the tubing 3010 may include a recess, window, or open portion 3012 that allows the tubing sections at that portion to move relative to one another. For example, the tubing 3010 may include separate tubing sections that are not connected at the open portion 3012, or with one tubing section slidably disposed in another tubing section. In this manner, as the second lace portion 3008 is tensioned, the separate tubing sections may move relative to one another and thereby constrict or compress about the shoe's collar or heel.

In some embodiments, a pair of pull tabs, 3005*a* and 3005*b*, may be coupled with the first lace portion 3006 and the second lace portion 3008, respectively. The pair of pull tabs, 3005*a* and 3005*b*, may be pulled simultaneously to cause a more uniform ejection of the lace from the tensioning mechanism. In this manner, the pair of pull tabs, 3005*a* and 3005*b*, may function similar to the component 3410 illustrated in FIG. 34.

Figure 31:
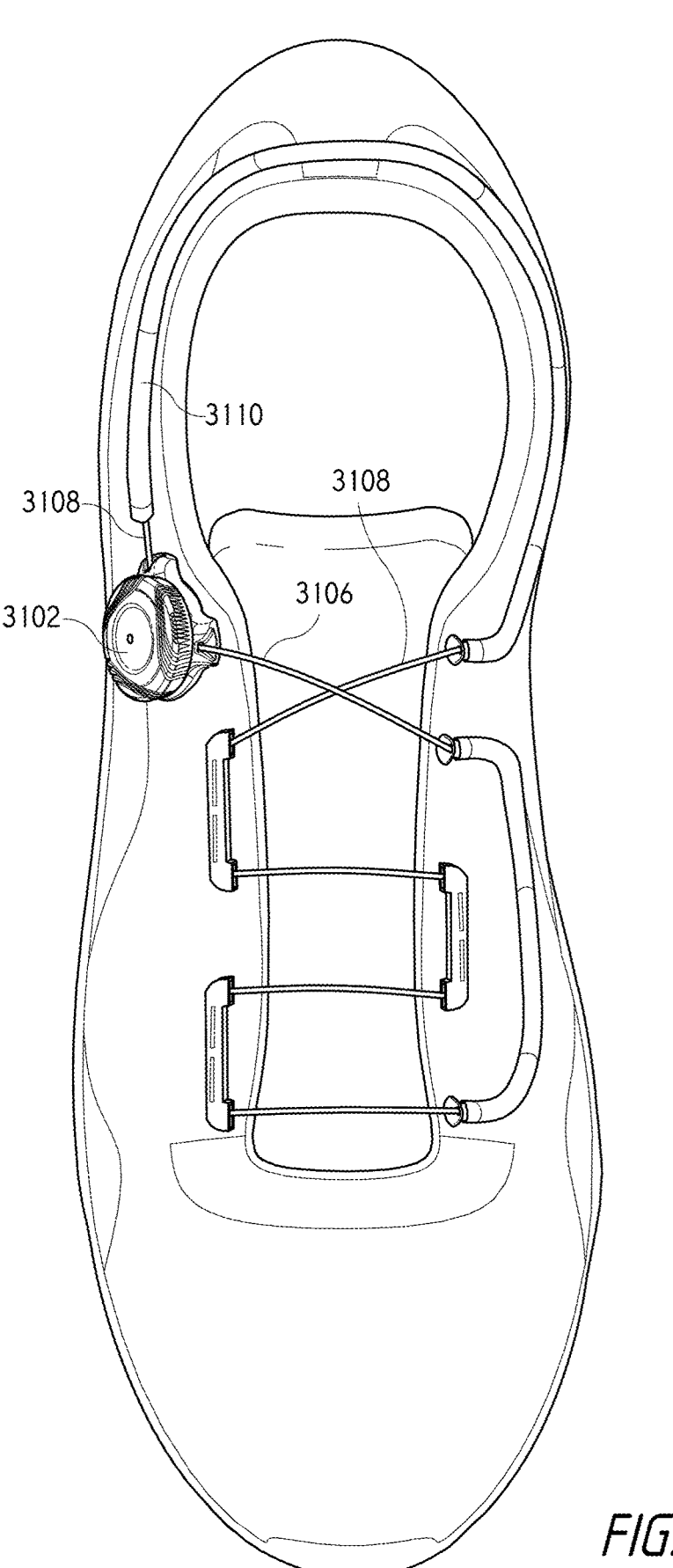
FIG. 31 illustrates an embodiment in which one portion of the lace is routed around the shoe's heel or collar.

FIG. 31 illustrates another embodiment in which one portion of the lace is routed around the shoe's heel or collar. Specifically, the second lace portion 3108 is routed from the tensioning mechanism via tubing 3110 around the shoe's heel. Unlike the embodiment of FIG. 30, the second lace portion 3108 is routed to the proximal end of the lace path while the first lace portion 3106 is routed from the tensioning mechanism to the distal end of the lace path. The tensioning of the embodiment of FIG. 31 will be similar to that of FIG. 30 except that a slight increase in tensioning at the proximal end of the lace path may be achieved due to crossing of the first and second lace portions, 3106 and 3108, at the proximal end.

Figure 32:
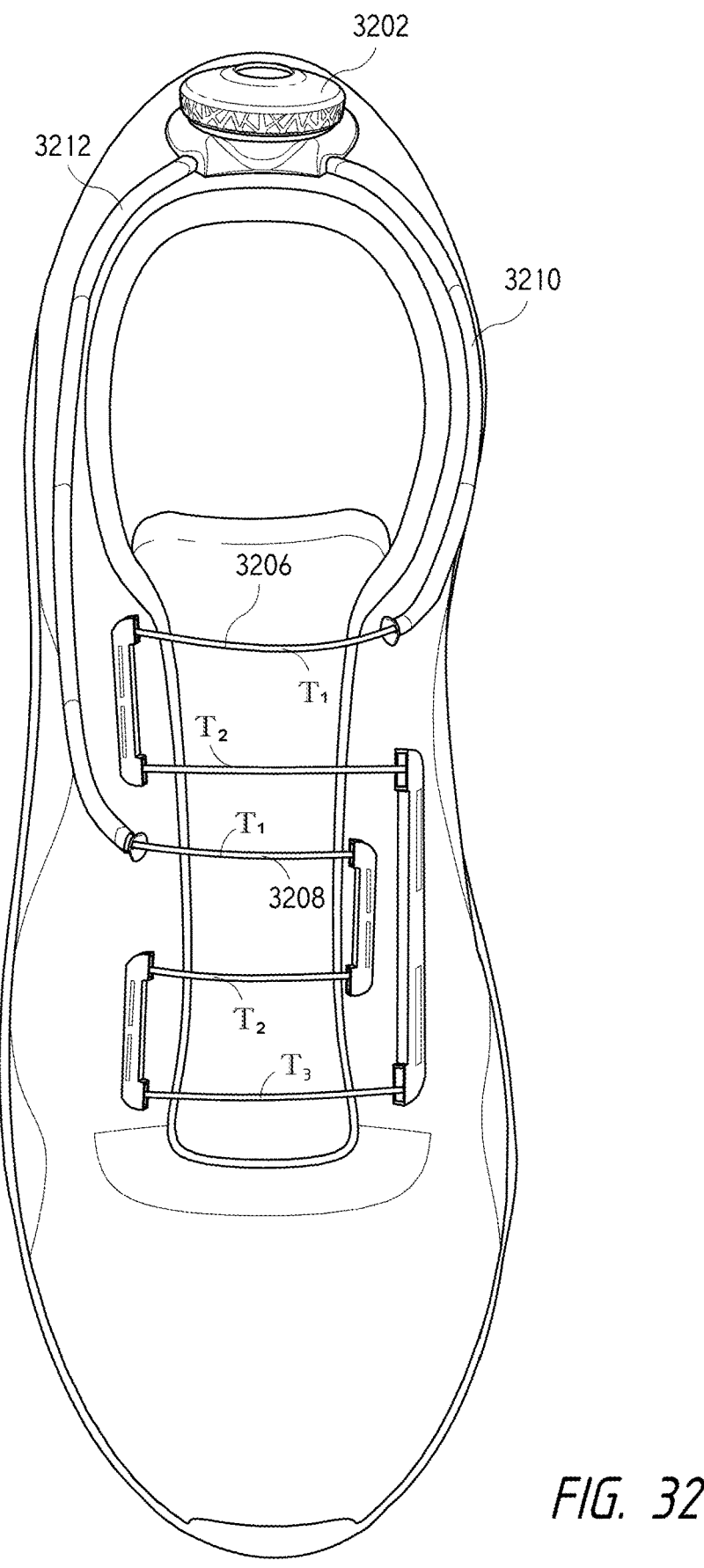
FIGS. 32-33 illustrate embodiments of shoes with the tensioning mechanism being positioned on the shoe's heel.

FIG. 32 illustrates the tensioning mechanism 3202 being positioned on the shoe's heel. The first lace portion 3206 is routed, via tubing 3210, from the tensioning mechanism 3202 to the proximal end of the lace path while the second lace portion 3208 is routed, via tubing 3212, from the tensioning mechanism 3202 to the mid-portion of the lace path. The lace configuration of FIG. 32 results in a primary tensioning $T_1$ of the proximal end and mid-portion of the lace path and a secondary tensioning $T_2$ along a lace crossing immediately distally of said portions. A tertiary tensioning $T_3$ occurs at the distal end of the lace path where the two lace portions meet or converge.

Figure 33:
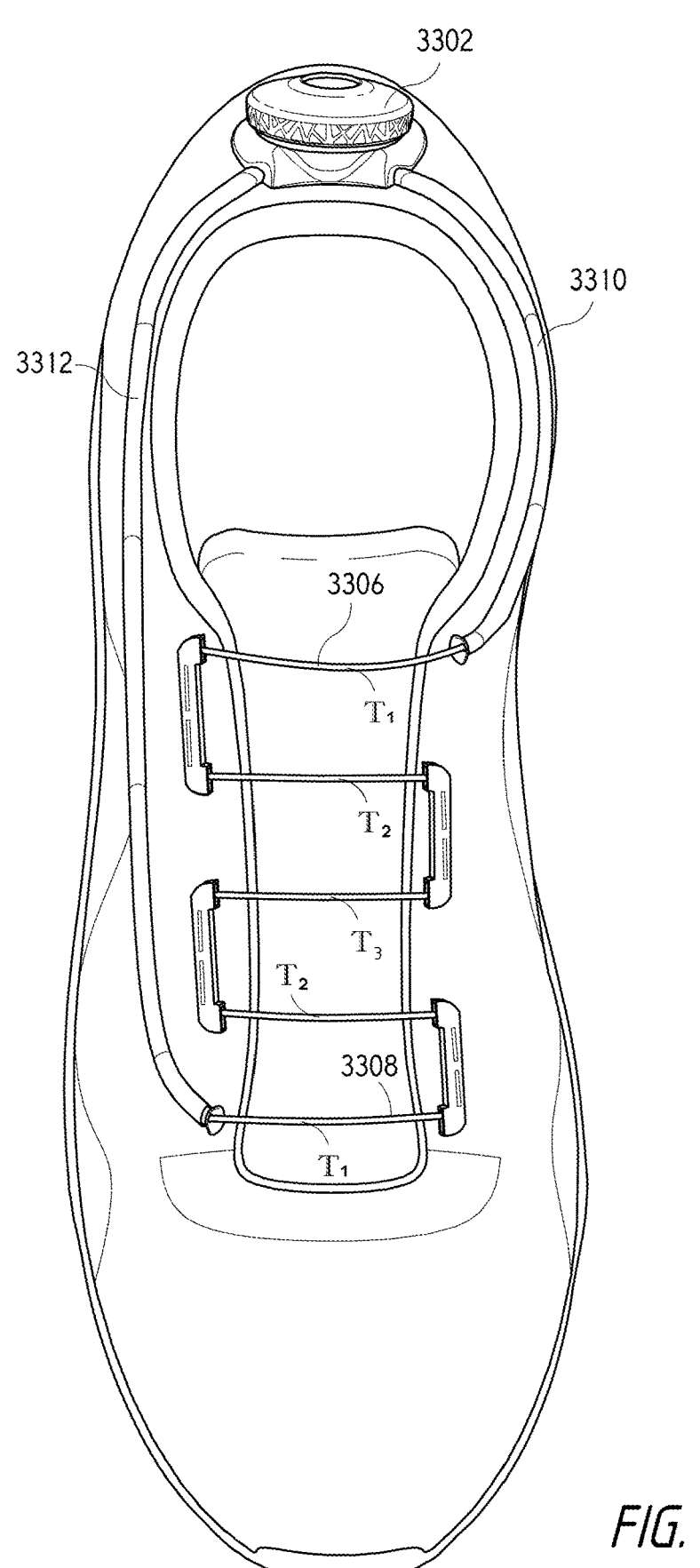

FIG. 33 illustrates another embodiment in which the tensioning mechanism 3302 is positioned on the shoe's heel and in which the first lace portion 3306 is routed, via tubing 3310, from the tensioning mechanism 3302 to the proximal end of the lace path. The second lace portion 3308 is routed, via tubing 3312, from the tensioning mechanism 3302 to the distal end of the lace path. The lace configuration of FIG. 33 results in a primary tensioning $T_1$ of the proximal and distal ends of the lace path, a secondary tensioning $T_2$ inward of the proximal and distal ends of the lace path, and a tertiary tensioning $T_3$ of the mid-portion of the lace path where the two lace portions meet or converge.

Figure 34:
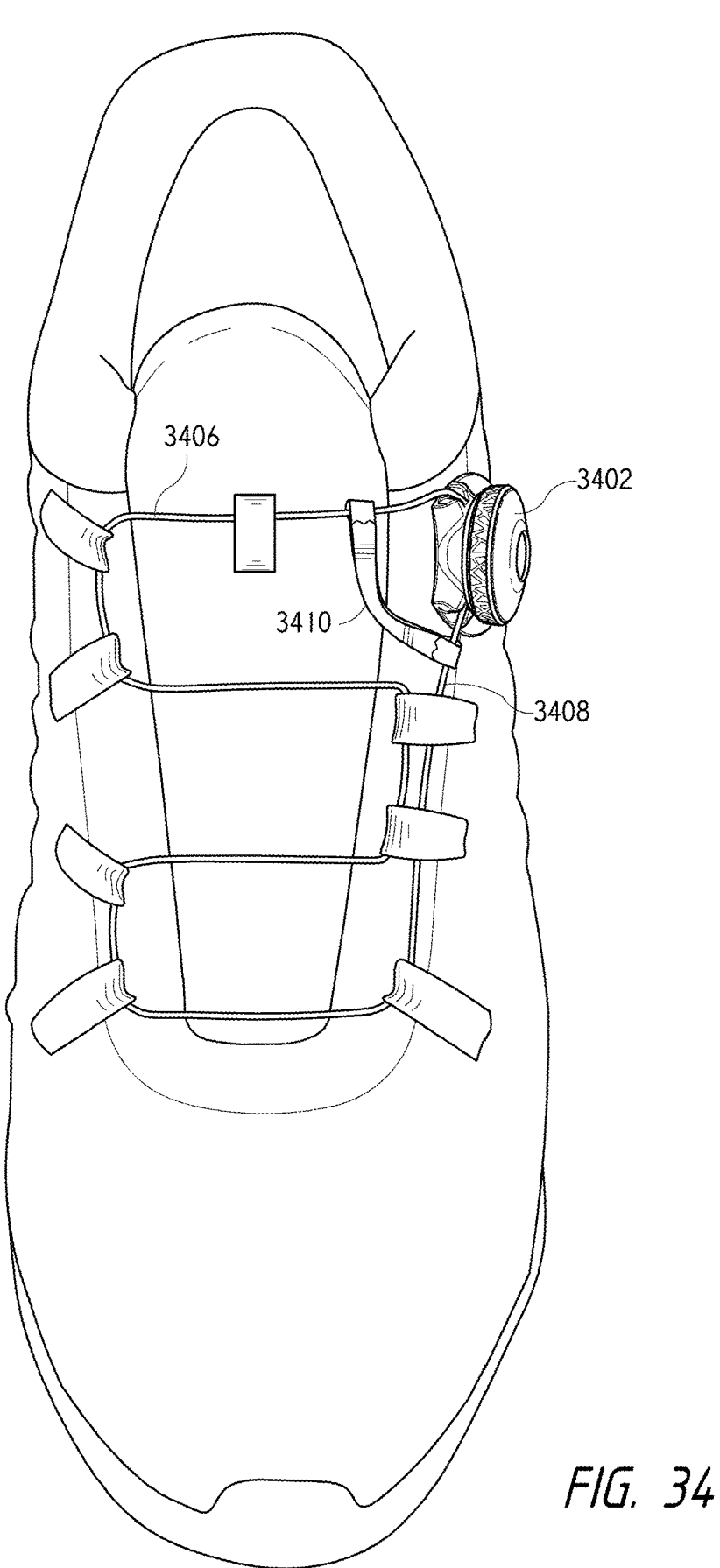
FIG. 34 illustrates an embodiment of a component that may be used to eliminate or minimize issues due to non-uniform lace ejection from the tensioning mechanism.

FIG. 34 illustrates an embodiment of a component 3410 that may be used to eliminate or minimize issues due to non-uniform lace ejection from the tensioning mechanism 3402. As previously described, opening of the shoe's tongue can result in a greater length of a first lace portion 3406 being ejected from the tensioning mechanism 3402 than a second lace portion 3408 due to the first lace portion 3406 being disposed across the tongue and the tongue being opened in a pivot like manner. As described, any non-ejected lace of the second lace portion 3408 remains disposed within the interior of the tightening mechanism and may tangle or bind within the tightening mechanism's interior, or cause other minor lace tensioning issues.

The component 3410 relieves these issues since it is directly attached to the first and second lace portions, 3406 and 3408, and may be pulled to evenly eject both portions of the lace from the tensioning mechanism's interior. Pulling the component 3410 causes both lace portions, 3406 and 3408, to be ejected evenly from the tensioning mechanism 3402, which ensures that none of the lace remains within the interior to cause binding, tangling or other issues.

Figure 35:
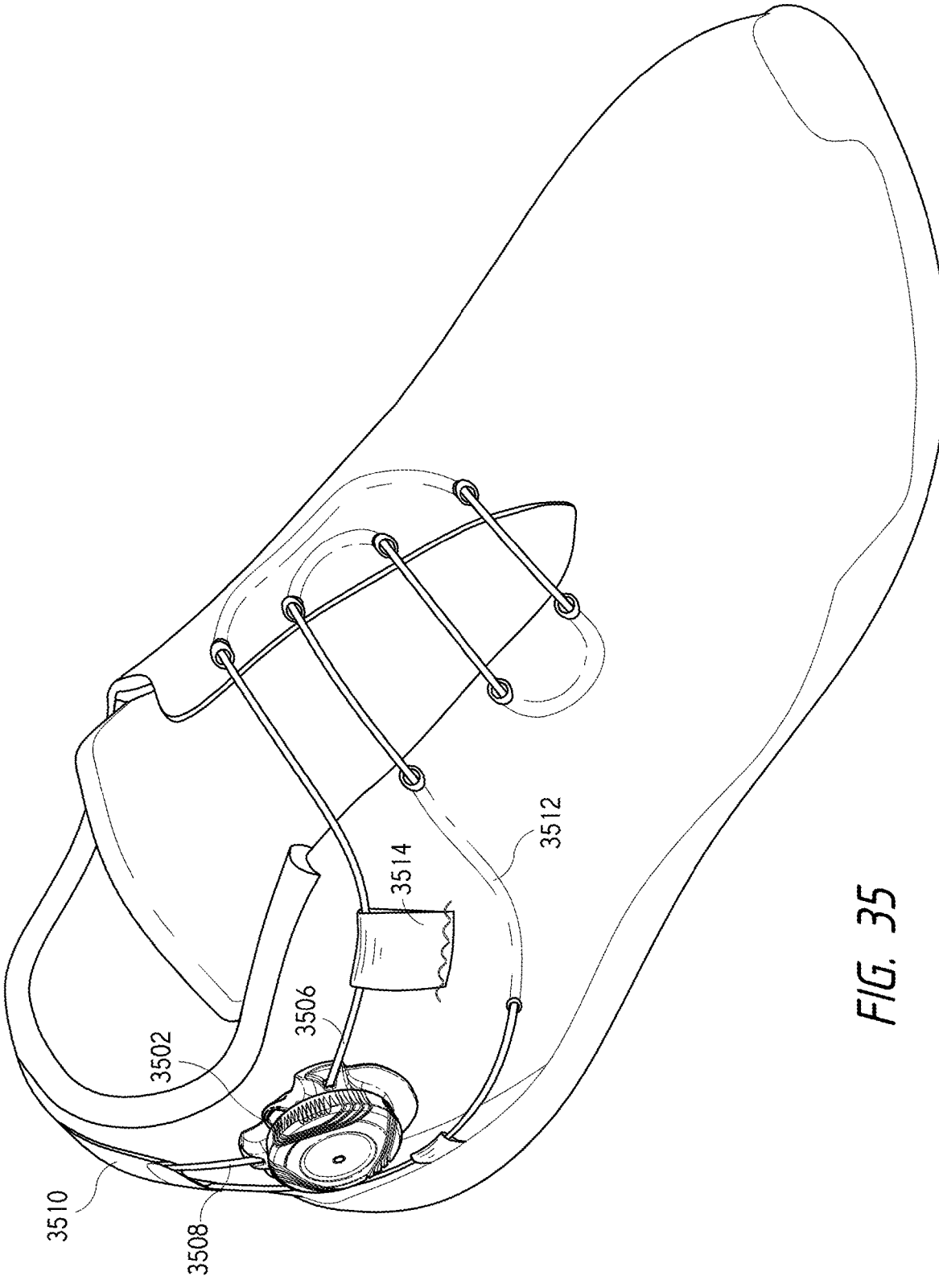
FIG. 35 illustrates a tensioning mechanism coupled with a side of the shoe between the tongue and heel.

FIG. 35 illustrates the tensioning mechanism 3502 being coupled with a side of the shoe between the tongue and heel. A first lace portion 3506 is routed from the tensioning mechanism 3502 to the proximal end of the lace path while a second lace portion 3508 is routed from the tensioning mechanism rearward toward the heel. The second lace portion 3508 is positioned within a guide 3510, which may be a rear strap, and is routed therefrom along the shoe's sole toward a mid-portion of the lace path. The first and/or second lace portions, 3506 and 3508, may be routed along the shoe via tubing 3512, webbing guides 3514, or other guides. In some instances, the tubing 3512 may be formed by coupling adjacent layers of the upper together to form a path, lumen, or channel. The adjacent layers of the upper may be coupled via adhesive bonding, stitching, heat welding, RF welding, or any other coupling technique.

A method of coupling a lacing system with an article or footwear is provided below. The method includes coupling a tensioning mechanism with the article and coupling a plurality of guide members with the article so as to define a lace path having a bottom end and a top end. A first portion of lace and a second portion of lace are coupled with the tensioning mechanism so that operation of the tensioning mechanism simultaneously tensions both the first portion and the second portion of the lace. The lace is routed along the lace path via the plurality of guide members so that the first portion is routed directly from the tensioning mechanism to the top end of the lace path and is routed therefrom toward the bottom end of the lace path, and so that the second portion is routed directly from the tensioning mechanism to a position adjacent the bottom end of the lace path such that tensioning of the first portion and the second portion of the lace via the tensioning mechanism immediately tensions the top end and the position adjacent the bottom end of the lace path. As illustrated in the various embodiments herein, the lace may be a single unitary component with the first and second lace portions converging at some point along the lace path, such on the side of the lace path.

In some embodiments, the position that is adjacent the bottom end of the lace path is a position that is equidistant from the top end and the bottom end of the lace path. In such embodiments, the second portion of the lace is routed from the position adjacent the bottom end of the lace path toward the bottom end of the lace path. In other embodiments, the second portion of lace is routed directly from the tensioning mechanism to the bottom end of the lace path and is routed therefrom toward the top end of the lace path such that tensioning of the first portion and the second portion of the lace via the tensioning mechanism immediately tensions the top end and the bottom end of the lace path. In some embodiments, the first lace portion or second lace portion is routed around a heel or collar of the shoe. In some embodiments, the tensioning mechanism is positioned on the heel of the shoe.

Although the embodiments described herein have been illustrated employing manual reel based devices, it should be realized that various other tensioning mechanisms or devices may be used. For example, a pull cord device and/or motorized device may be employed to tension the lace as desired. In a specific embodiment, a motorized lace tensioning device may be concealed within or adjacent the sole of the shoe and the lace may be routed to the motorized lace tensioning device under one or more layers of the upper.

While several embodiments and arrangements of various components are described herein, it should be understood that the various components and/or combination of components described in the various embodiments may be modified, rearranged, changed, adjusted, and the like. For example, the arrangement of components in any of the described embodiments may be adjusted or rearranged and/or the various described components may be employed in any of the embodiments in which they are not currently described or employed. As such, it should be realized that the various embodiments are not limited to the specific arrangement and/or component structures described herein.

In addition, it is to be understood that any workable combination of the features and elements disclosed herein is also considered to be disclosed. Additionally, any time a feature is not discussed with regard in an embodiment in this disclosure, a person of skill in the art is hereby put on notice that some embodiments of the invention may implicitly and specifically exclude such features, thereby providing support for negative claim limitations.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A lacing system for tightening a brace comprising:
a tensioning mechanism;
a plurality of guide members that are coupled with the brace along a lace path about an opening of the brace, the plurality of guide members including:
a first guide member that is attached to a first side of the opening;
a second guide member that is attached to the first side of the opening; and
a single lace that is operationally coupled with the tensioning mechanism and routed along the lace path via the plurality of guide members, the single lace comprising a first portion and a second portion, wherein the single lace is routed along the lace path such that:
the first portion is routed directly from the tensioning mechanism to a top end of the lace path and is routed therefrom toward a bottom end of the lace path, wherein the first portion is routed toward the bottom end of the lace path via the first guide member;
the second portion is routed directly from the tensioning mechanism to a position adjacent a midpoint of the lace path and is routed therefrom across the opening one or more times to the bottom end of the lace path such that tensioning of the first portion and the second portion of the lace via the tensioning mechanism immediately tensions the top end and the position adjacent the midpoint of the lace path, wherein the second portion is routed from the tensioning mechanism to the position adjacent the midpoint of the lace path via the second guide member, the second portion being routed parallel to the first portion on the first side of the brace and the second portion being routed so that the second portion does not frictionally engage with the first guide member; and
the first portion and the second portion are routed directly from the tensioning mechanism oriented orthogonally relative to each other.

2. The lacing system of claim 1, wherein the plurality of guide members includes at least one guide with an elongated channel or a wide gap between opposing ends of the at least one guide.

3. The lacing system of claim 2, wherein the plurality of guide members further includes a second guide having a longitudinal length, or gap between opposing ends, that is shorter than the guide with the elongated channel or wide gap, and wherein the guide with the elongated channel or wide gap is positioned laterally outward from the second guide in respect to the lace path so that opposing ends of the second guide are disposed between the opposing ends of the guide with the elongated channel.

4. The lacing system of claim 2, wherein the brace is a wrist brace.

5. The lacing system of claim 1, wherein the second portion is routed directly from the tensioning mechanism to the midpoint of the lace path, and wherein the second portion of the lace is routed from the midpoint of the lace path toward the bottom end of the lace path.

6. The lacing system of claim 1, wherein the first portion of lace and the second portion of lace are each operationally coupled with the tensioning mechanism so that operation of the tensioning mechanism simultaneously tensions both the first portion and the second portion.

7. A lacing system for tightening a brace, the brace having an opening that enables a user to don and doff the brace, the brace also having a lace path that extends along the opening, the lace path having a bottom end, a top end, and a mid-portion, the lacing system comprising:

a tensioning mechanism;

a plurality of guide members that are coupled with the brace; and a lace that is operationally coupled with the tensioning mechanism and routed about the opening along the lace path via the plurality of guide members, the lace comprising a first portion and a second portion that are each operationally coupled with the tensioning mechanism so that operation of the tensioning mechanism simultaneously tensions both the first portion and the second portion, wherein the lace is routed along the lace path such that:

the first portion is routed directly from the tensioning mechanism to the top end of the lace path and is routed therefrom across the opening toward the mid-portion of the lace path; and the second portion is routed directly from the tensioning mechanism and along the same side of the brace as the tensioning mechanism to adjacent the mid-portion of the lace path and is routed therefrom across the opening of the brace one or more times toward the bottom end of the lace path such that tensioning of the first portion and the second portion of the lace immediately tensions the top end and the mid-portion of the lace path and thereby immediately tightens corresponding portions of the brace;

wherein the lace is a unitary member with the first portion connected to the second portion between the mid-portion and the bottom end of the lace path; and wherein when under tension, the lace does not cross itself or touch another portion of the lace along an entire length of the lace path.

8. The lacing system of claim 7, wherein the brace includes a first main body and a second main body that is separate from the first main body, wherein the first main body and the second main body are configured to wrap around a body member and are coupleable together to provide a gross closure of the brace about the body member.

9. The lacing system of claim 8, wherein the tensioning mechanism is attached to the first main body.

10. The lacing system of claim 7, wherein the plurality of guide members includes at least one guide with an elongated channel.

11. The lacing system of claim 10, wherein the plurality of guide members further includes a second guide having a longitudinal length that is shorter than the guide with the elongated channel, and wherein the guide with the elongated channel is positioned laterally outward from the second guide in respect to the lace path so that opposing ends of the second guide are disposed between opposing ends of the guide with the elongated channel.

12. The lacing system of claim 7, wherein the first portion is routed directly from the tensioning mechanism to the top end of the lace path and/or the second portion is routed directly from the tensioning mechanism to adjacent the mid-portion of the lace path via tubing.

13. The lacing system of claim 7, wherein the tensioning mechanism comprises a rotary based device that is manually operable or a motorized device.

14. The lacing system of claim 7, wherein the brace is a wrist brace.

15. A lacing system for tightening a brace, the brace having a first side and a second side that are separated by an opening, the lacing system comprising:

a tensioning mechanism;

a single lace that is operationally coupled with the tensioning mechanism and routed along a lace path about the opening of the brace, the single lace comprising a first portion and a second portion;

a first guide member that is attached to the first side of the brace, the first guide member having a channel that is aligned longitudinally along the lace path and that is configured to route the first portion of the lace along the lace path; and a second guide member that is attached to the first side of the brace, the second guide member having a channel that is aligned longitudinally along the lace path and that is configured to route the second portion of the lace along the lace path, wherein:

the first portion is routed directly from the tensioning mechanism to a top end of the lace path and is routed therefrom across the opening toward a mid-portion of the lace path;

the second portion is routed directly from the tensioning mechanism to adjacent the mid-portion of the lace path and is routed therefrom across the opening of the brace one or more times toward a bottom end of the lace path;

a length of the channel of the second guide member is longer than a length of the channel of the first guide member;

the second guide member is positioned along the lace path and in respect to the first guide member such that opposing ends of the channel of the first guide member are disposed between opposing ends of the channel of the second guide member; and the tensioning mechanism is positioned on an opposite side of the brace than the second guide member.

16. The lacing system of claim 15, wherein the second guide member is positioned latterly outward or offset from the first guide member with respect to the lace path.

17. The lacing system of claim 15, wherein the second portion of lace is positioned through the channel of the first guide member.

18. The lacing system of claim 15, wherein the brace is a wrist brace.

19. The lacing system of claim 15, wherein the brace is a back brace.

* * * * *